US006800653B2

(12) United States Patent
Regueiro-Ren et al.

(10) Patent No.: US 6,800,653 B2
(45) Date of Patent: Oct. 5, 2004

(54) EPOTHILONE DERIVATIVES

(75) Inventors: Alicia Regueiro-Ren, Middletown, CT (US); Robert M. Borzilleri, New Hope, PA (US); Gregory D. Vite, Titusville, NJ (US); Soong-Hoon Kim, Titusville, NJ (US)

(73) Assignee: Bristol-Myers Squibb Compnay, Princeton, NJ (US)

( * ) Notice: Subject to any disclaimer, the term of this patent is extended or adjusted under 35 U.S.C. 154(b) by 0 days.

(21) Appl. No.: 10/144,879

(22) Filed: May 14, 2002

(65) Prior Publication Data

US 2003/0087888 A1 May 8, 2003

Related U.S. Application Data

(60) Provisional application No. 60/295,499, filed on Jun. 1, 2001.

(51) Int. Cl.$^7$ ................ A61K 31/425; C07D 277/30
(52) U.S. Cl. .......................... 514/365; 548/204
(58) Field of Search .......................... 514/365; 548/204

(56) References Cited

U.S. PATENT DOCUMENTS

| | | | |
|---|---|---|---|
| 6,194,181 B1 | 2/2001 | Hofmann et al. | |
| 6,204,388 B1 | 3/2001 | Danishefsky et al. | |
| 6,211,412 B1 | 4/2001 | Georg et al. | |
| 6,242,469 B1 | 6/2001 | Danishefsky et al. | |
| 6,291,684 B1 * | 9/2001 | Borzilleri et al. | 548/961 |
| 6,300,355 B1 * | 10/2001 | Danishefsky et al. | 514/374 |
| 6,316,630 B1 | 11/2001 | Danishefsky et al. | |
| 6,369,234 B1 | 4/2002 | Danishefsky et al. | |
| 6,380,394 B1 | 4/2002 | Nicolaou et al. | |
| 6,384,230 B1 | 5/2002 | Mulzer et al. | |
| 6,387,927 B1 | 5/2002 | Altmann et al. | |
| 6,399,638 B1 | 6/2002 | Vite et al. | |
| 6,531,497 B1 * | 3/2003 | Nicolaou et al. | 514/370 |
| 6,583,290 B1 * | 6/2003 | Julien et al. | 548/203 |
| 6,589,968 B2 * | 7/2003 | Arslanian et al. | 514/365 |

FOREIGN PATENT DOCUMENTS

| | | |
|---|---|---|
| DE | 4138042.8 | 5/1993 |
| DE | 19542986.9 | 5/1997 |
| DE | 19639456.2 | 5/1997 |
| DE | 19636343.8 | 3/1998 |
| DE | 19645361.5 | 4/1998 |
| DE | 19645362.3 | 4/1998 |
| DE | 19647580.5 | 5/1998 |
| DE | 19701758 | 7/1998 |
| DE | 19707505.3 | 9/1998 |
| DE | 19713970 | 10/1998 |
| DE | 19720312 | 11/1998 |
| DE | 19821954 | 11/1998 |
| DE | 19726627 | 12/1998 |
| EP | 879 605 | 11/1998 |
| WO | 93/10121 | 5/1993 |
| WO | 97/19086 | 5/1997 |
| WO | 98/08849 | 3/1998 |
| WO | 98/22461 | 5/1998 |
| WO | 98/24427 | 6/1998 |
| WO | 98/25929 | 6/1998 |
| WO | 98/38192 | 9/1998 |
| WO | 98/47891 | 10/1998 |
| WO | 99/01124 | 1/1999 |
| WO | 99/02514 | 1/1999 |
| WO | 99/03848 | 1/1999 |
| WO | 99/07692 | 2/1999 |
| WO | 99/27890 | 6/1999 |
| WO | 99/39694 | 8/1999 |
| WO | 99/42602 | 8/1999 |
| WO | 99/43320 | 9/1999 |
| WO | 99/43653 | 9/1999 |
| WO | 99/54319 | 10/1999 |
| WO | 99/67252 | 12/1999 |
| WO | 00/00485 | 1/2000 |
| WO | 00/31247 | 6/2000 |
| WO | 00/37473 | 6/2000 |
| WO | 00/49021 | 8/2000 |
| WO | 00/66589 | 11/2000 |

OTHER PUBLICATIONS

Balog, A., et al., "Total Synthesis of (–)–Epothilone A", *Angew. Chem. Int. Ed. Engl.*, vol. 35, No. 23/24, 2801–2803 (1996).

Bertini, F., et al., "Alkenes from Epoxides by Reductive Elimination with Magnesium Bromide–Magnesium Amalgam", *Chem. Commun.*, 144 (1970).

Bollag, D.M., et al., "Epothilones, A New Class of Microtubule–stabilizing Agents with a Taxol–like Mechanism of Action", *Cancer Res.* 55, No. 11, 2325–2333 (1995).

Fujisawa, T., et al., "Deoxygenation of Epoxides to Olefins with FeCl$_3$–n–BuLi System", *Chem. Lett.*, 883–886 (1974).

Fujiwara, Y., et al., "Reductive Coupling of Carbonyl Compounds to Olefins by Tungsten Hexachloride–Lithium Aluminum Hydride and Some Tungsten and Molybdenum Carbonyls", *J. Org. Chem.*, vol. 43, No. 12, 2477–2479 (1978).

Gladysz, J. A., et al., "Deoxygenation of Epoxides by Metal Atom Cocondensation", *J. Org. Chem.*, vol. 41, No. 22, 3647–3648 (1976).

Hofle, G., et al., "Epothilone A and B—Novel 16–Membered Macrolides with Cytotoxic Activity: Isolation, Crystal Structure, and Conformation in Solution", *Angew. Chem. Int. Ed. Engl.*, vol. 35, No. 13/14, 1567–1569 (1996).

Hofle, G., et al., "N–Oxidation of Epothilone A–C and O–Acyl Rearrangement to C–19 and C–21 –Substituted Epothilones", *Angew. Chem. Int. Ed.*, vol. 38, No. 13/14, 1971–1974 (1999).

Inokuchi, T., et al., "Opening of Epoxides to Olefins or Halohydrins with Vanadium(II)–Tetrahydrofuran or Vanadium(III)–Tetrahydrofuran Complexes", *Synlett*, No. 6, 510–512 (1992).

(List continued on next page.)

*Primary Examiner*—Deborah C. Lambkin
(74) *Attorney, Agent, or Firm*—Anastasia P. Winslow

(57) ABSTRACT

The present invention relates to 12,13-position modified epothilone derivatives, methods of preparation of the derivatives, and intermediates therefor.

20 Claims, No Drawings

OTHER PUBLICATIONS

Kowalski, R. J., et al., "Activities of the Microtubule–stabilizing Agents Epothilones A and B with Purified Tubulin and in Cells Resistant to Paclitaxel (Taxol®)" *J. Biol. Chem.*, vol. 272, No. 4, 2534–2541 (1997).

Kupchan, S. M., et al., "Reductive Elimination of Epoxides to Olefins with Zinc–Copper Couple", *J. Org. Chem.*, vol. 36, No. 9, 1187–1190 (1971).

Martin, M. G., et al., "Epoxides as Alkene Protecting Groups. A Mild and Efficient Deoxygenation", *Tetrahedron Letters*, vol. 25, No. 3, 251–254 (1984).

McMurry, J. E., et al., "Reduction of Epoxides to Olefins with Low Valent Titanium", *J. Org. Chem.*, vol. 40, No. 17, 2555–2556 (1975).

McMurry, J. E., et al., "Some Deoxygenation Reactions with Low–Valent Titanium ($TiCl_3$/$LiAlH_4$)", *J. Org. Chem.*, vol. 43, No. 17, 3249–3254 (1978).

Meng, D., et al., "Remote Effects in Macrolide Formation Through Ring–Forming Olefin Metathesis: An Application to the Synthesis of Fully Active Epothilone Congeners", *J. Am. Chem. Soc.*, vol. 119, No. 11, 2733–2734 (1997).

Nicolaou, K. C., et al., "An Approach to Epothilones Based on Olefin Metathesis", *Angew. Chem. Int. Ed. Engl.*, vol. 35, No. 20, 2399–2401 (1996).

Nicolaou, K. C., et al., "Total Synthesis of Epothilone A: The Macrolactonization Approach", *Angew. Chem. Int. Ed. Engl.*, vol. 36, No. 5, 525–527 (1997).

Nicolaou, K. C., et al., "Designed Epothilones: Combinatorial Synthesis, Tubulin Assembly Properties, and Cytotoxic Action against Taxol–Resistant Tumor Cells", *Angew. Chem. Int. Ed. Engl.*, vol. 36, No. 19, 2097–2103 (1997).

Nicolaou, K.C., et al., "The Olefin Metathesis Approach to Epothilone A and Its Analogues", *J. Am. Chem. Soc.*, vol. 119, No. 34, 7960–7973 (1997).

Nicolaou, K. C., et al., "Total Syntheses of Epothilones A and B via a Macrolactonization–Based Strategy", *J. Am. Chem. Soc.*, vol. 119, No. 34, 7974–7991 (1997).

Nicolaou, K. C., et al., "Synthesis of Epothilones A and B in Solid and Solution Phase", *Nature*, vol. 387, 268–272 (1997).

Nicolaou, K. C., et al., "Synthesis of Epothilones A and B in Solid and Solution Phase" (Correction to *Nature* 387, 268–272 (1997), *Nature*, 390, 100 (1997).

Raucher, S., et al., "Total Synthesis of (+)–Dihydrocostunolide via Tandem Cope–Claisen Rearrangement", *J. Org. Chem.*, vol. 51, No. 26, 5503–5505 (1986).

Sato, M, et al., "Reduction of Organic Compounds with Low–Valent Niobium ($NbCl_5$/$NaAlH_4$)", *Chem. Letters*, 157–160 (1982).

Schinzer, D., et al., "Total Synthesis of (−)–Epothilone A", *Angew. Chem. Int. Ed. Engl.*, vol. 36, No. 5, 523–524 (1997).

Schobert, R., et al., "Reduction and Isomerization of Oxiranes and α–Diazoketones by Various Early Transition Metallocenes", *Synlett*, vol. 8, 465–466 (1990).

Sharpless, K. B., et al., "Lower Valent Tungsten Halides. A New Class of Reagents for Deoxygenation of Organic Molecules", *J. Amer. Chem. Soc.*, vol. 94, No. 18, 6538–6540 (1972).

Su, D.–S., et al., "Total Synthesis of (−)–Epothilone B: An Extension of the Suzuki Coupling Method and Insights into Structure–Activity Relationships of the Epothilones", *Angew. Chem. Int Ed. Engl.*, vol. 36, No. 7, 757–759 (1997).

Su, D.–S., et al., "Structure–Activity Relationships of the Epothilones and the First In Vivo Comparison with Paclitaxel", *Angew. Chem. Int. Ed. Engl.*, vol. 36, No. 19, 2093–2096 (1997).

Victory, S. F., et al., "Relative Stereochemistry and Solution Conformation of the Novel Paclitaxel–Like Antimitotic Agent Epothilone A", *Bioorg. Med. Chem. Letts.*, vol. 6., No. 7, 893–898 (1996).

Winkler, J. D., et al., "A Model For The Taxol (Paclitaxel)/ Epothilone Pharmacophore", *Boorg. Med. Chem. Letts.*, vol. 6, No. 24, 2963–2966 (1996).

Yang, Z., et al., "Total Synthesis of Epothilone A: The Olefin Metathesis Approach", *Angew. Chem. Int. Ed. Engl.*, vol. 36, No. 1/2, 166–168 (1997).

Bollag, D., et al., "Epothilone, A New Structural Class of Microtubule Stabilizer", Abstract, *Proc. Am. Assoc. Cancer Res.*, vol. 36, 86 Meet. 454 (1995).

Bollag, D., "Epothilones: Novel Microtubule–Stabilising Agents", *Expert Opin. Invest. Drugs*, vol. 6, No. 7, 867–873 (1997).

Bertinato, P., et al., "Studies Toward a Synthesis of Epothilone A: Stereocontrolled Assembly of the Acyl Region and Models for Macrocylization", J. Org. Chem., vol. 61, No. 23, 8000–8001 (1996).

*Chemical & Engineering News*, "Epothilone Epiphany: Total Syntheses", vol. 74, No. 52, 24–26 (1996).

*Chemical & Engineering News*, "First Total Synthesis of Epothilone B", vol. 75, No. 13, 23 (1997).

*Chemical & Engineering News*, "Solid–Phase Epothilone Synthesis Used to Create Analog Library", vol. 75, No. 20, 33 (1997).

Claus, E., et al., "Synthesis of the C1–C9 Segment of Epothilons", *Tetrahedron Lett.*, vol. 38, No. 8, 1359–1362 (1997).

De Brabander, J., et al., "Towards a Synthesis of Epothilone A: Rapid Assembly of the C1–C6 and C7–C12 Fragments", *Synlett*, vol. 7, 824–826 (1997).

Gabriel, T. and Wessjohann, L., "The Chromium–Reformatsky Reaction: Asymmetric Synthesis of the Aldol Fragment of the Cytotoxic Epothilons from 3–(2–Bromoacyl)–2–Oxazolidinones", *Tetrahedron Lett.*, vol. 38, No. 8, 1363–1366 (1997).

Gerth, K., et al., "Epothilons A and B: Antifungal and Cytotoxic Compunds from *Sorangiusm cellulosum* (Myxobacteria) Production, Physico–chemical and Biological Properties", *J. Antibiotics*, vol. 49, No. 6, 560–563 (1996).

Marshall, A., "Total Synthesis of Epothilone", *Nature Biotechnology*, vol. 15, No. 3, 205 (1997).

Meng, D., et al., "Studies Toward a Synthesis of Epothilone A: Use of Hydropyran Templates for the Managment of Acyclic Stereochemical Relationships", *J. Org. Chem.*, vol. 61, No. 23, 7998–7999 (1996).

Meng, D., et al., "Total Syntheses of Epothilones A and B", *J. Am. Chem. Soc.*, vol. 119, No. 42, 10073–10092 (1997).

Mensching, S. and Kalesse, M., "Generation of Thiazoles by Column Dehydrogenation of Thiazolidines with $MnO_2$", *J. Prakt. Chem.*, vol. 339, No. 1, 96–97 (1997).

Mulzer, J. and Mantoulidis, A., "Synthesis of the C(1)–C–(9) Segment of the Cytotoxic Macrolides Epothilon A and B", *Tetrahedron Lett.*, vol. 37, No. 51, 9179–9182 (1996).

Nicolaou, K, et al., "Chemistry, Biology and Medicine of Selected Tubulin Polymerizing Agents", *Pure Appl. Chem.*, vol. 71, No. 6, 989–997 (1999).

Nicolaou, K., et al., "Total Synthesis of Epothilone E and Related Side–chain Modified Analogues Via a Stille Coupling Based Strategy", *Bioorg. Med. Chem.,* vol. 7, No. 5, 665–697 (1999).

Schinzer, D., et al., "Studies Towards the Total Synthesis of Epothilones: Asymmetric Synthesis of the Key Fragments", *Chem. Eur. J.,* vol. 2, No. 22, 1477–1482 (1996).

Taylor, R. and Haley, J., "Towards the Synthesis of Epothilone A: Enantioselective Preparation of the Thiazole Sidechain and Macrocyclic Ring Closure", *Tetrahedron Lett.,* vol. 38, No. 12, 2061–2064 (1997).

Schinzer, D., et al., "Syntheses of (–)–Epothilone A", *Chem. Eur. J.,* vol. 5, No. 9, 2483–2491 (1999).

Schinzer, D., et al., "Syntheses of (–)–Epothilone B", *Chem. Eur. J.,* vol. 5, No. 9, 2492–2500 (1999).

Nicolaou, K. C., "Synthesis and Biological Properties of C12,13–Cyclopropylepothilone A and Related Epothilones", *Chemistry & Biology,* vol. 5, No. 7, 365–372 (1998).

Altmann, K.H., et al., "Epothilones and Related Structures—A New Class of Microtubule Inhibitors With Patent In Vivo Antitumor Activity," Biochim. Biophys Acta, 1470 (2000).

Nicolaou et al., "Total Synthesis of Epothilone E and Analogs with Modified Side Chains Through The Stille Coupling Reaction", Angew. Chem. Int. Ed. 37, 84–87 (1998).

Nicolaou et al., "Total Synthesis of Oxazole– and Cyclopropane–Containing Epothilone B Analogues by the Macrolactonization Approach", Chemistry, European Journal, vol. 3, No. 12, 1971–1986 (1997).

Nicolaou et al., "Chemical Biology of Epothilones", Angew. Chem. Int. Ed., 37, 2014–2045 (1988).

* cited by examiner

EPOTHILONE DERIVATIVES

CROSS-REFERENCE TO RELATED APPLICATION

This application claims priority from provisional application Ser. No. 60/295,499, filed Jun. 1, 2001 which is incorporated herein by reference in its entirety.

FIELD OF THE INVENTION

The invention relates to the fields of organic synthesis, medicinal chemistry, cancer chemotherapeutic agents and cancer chemotherapy. Specifically, the invention relates to microtubule-stabilizing antitumor compounds of the epothilone class.

BACKGROUND OF THE INVENTION

Epothilones are macrolide compounds which find utility in the pharmaceutical field. For example, Epothilones A and B having the structures:

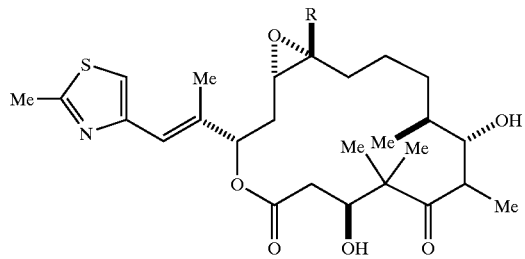

Epothilone A    R=H
Epothilone B    R=Me have been found to exert microtubule-stabilizing effects similar to TAXOL™ and hence cytotoxic activity against rapidly proliferating cells, such as, tumor cells or other hyperproliferative cellular disease; see Hofle et al., *Angew. Chem. Int. Ed. Engl.*, 1996, 35:1567–1569.

SUMMARY OF THE INVENTION

The present invention relates to compounds of formula I and formula II:

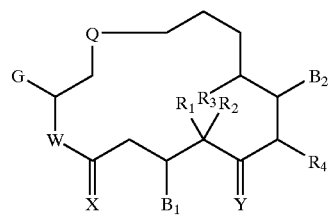

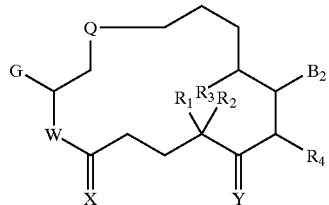

Q is selected from the group consisting of

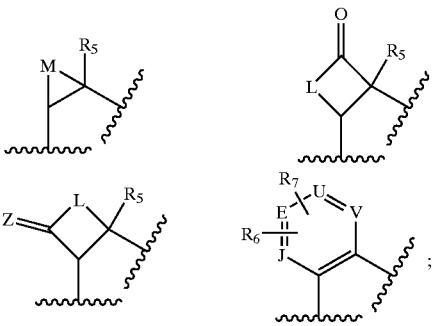

G is selected from the group consisting of alkyl, substituted alkyl, aryl, substituted aryl, heterocyclo,

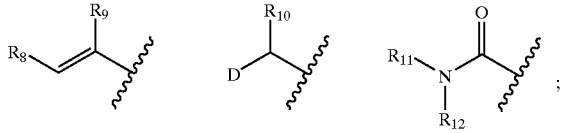

L is O, S, SO, $SO_2$ or $NR_{13}$ or $CR_{14}R_{15}$;
W is O or $NR_{16}$;
X is O, S, $CHR_{17}$ or H, $R_{18}$;
Z is O; S; H, $R_{19}$ or $R_{20}$, $R_{21}$;
Y is selected from the group consisting of O; H, H; H, $OR_{22}$; $OR_{23}$, $OR_{23}$; $NOR_{24}$; H, $NOR_{25}$; H, $NR_{26}R_{27}$; $NHNR_{28}R_{29}$; H, $NHNR_{30}R_{31}$; or $CHR_{32}$; where $OR_{23}$, $OR_{23}$ can be a cyclic ketal;
$B_1$ and $B_2$ are selected from the group consisting of H, $OR_{33}$, $OCOR_{34}$, $OCONR_{35}R_{36}$, $NR_{37}R_{38}$ or $NR_{39}CONR_{40}R_{41}$;
D is selected from the group consisting of $NR_{42}R_{43}$ or heterocyclo;
M is selected from the group consisting of S, C=O, S=O, $SO_2$, $NR_{44}$, or $CR_{45}R_{46}$;
J, E, U, and V are selected from carbon, oxygen, nitrogen or sulfur; or V may be absent;
$R_1$, $R_2$, $R_3$, and $R_4$, are selected from H, lower alkyl;
$R_5$, $R_8$, $R_9$, $R_{10}$ and $R_{11}$ are selected from the group consisting of H, alkyl, substituted alkyl, aryl, substituted aryl, cycloalkyl, heterocyclo or substituted heterocyclo;
$R_6$ and $R_7$ are selected from the group consisting of H, alkyl, substituted alkyl, halogen, nitro, cyano, $OR_{47}$, $NR_{48}R_{49}$, $R_{50}C=O$;
$R_{17}$, $R_{18}$, $R_{22}$ and $R_{23}$ are selected from the group consisting of H, alkyl, and substituted alkyl;
$R_{20}$, $R_{21}$, $R_{24}$, $R_{25}$, $R_{26}$, $R_{28}$, $R_{30}$, $R_{32}$, $R_{33}$, $R_{34}$, $R_{35}$, $R_{36}$, $R_{37}$, $R_{39}$, $R_{40}$, $R_{41}$, $R_{42}$, $R_{47}$, $R_{48}$, $R_{50}$, $R_{52}$, $R_{53}$, $R_{54}$, $R_{56}$, $R_{57}$, $R_{58}$, $R_{59}$, $R_{61}$, $R_{62}$, $R_{64}$, and $R_{65}$ are selected from the group of H, alkyl, substituted alkyl, aryl, substituted aryl; heterocyclo or substituted heterocyclo;

$R_{63}$ is H, alkyl having 2 to 20 carbon atoms, substituted alkyl, aryl, substituted aryl; heterocyclo or substituted heterocyclo;

or $R_{62}$ and $R_{63}$, together with the nitrogen atom to which they are attached, form a heterocycle or substituted heterocycle;

$R_{51}$ is heterocyclo or substituted heterocyclo;

$R_{12}$, $R_{13}$, $R_{16}$, $R_{27}$, $R_{29}$, $R_{31}$, $R_{38}$, $R_{43}$, $R_{49}$, $R_{55}$ and $R_{60}$ are selected from the group consisting of H, alkyl, substituted alkyl, substituted aryl, cycloalkyl, heterocyclo, $R_{51}C=O$, $R_{52}OC=O$, $R_{53}SO_2$, hydroxy, O-alkyl or O-substituted alkyl; when X is O then $R_{16}$ is not $R_{51}C=O$, $R_{52}OC=O$, and $R_{53}SO_2$; and wherein $R_{44}$ is further amino and $R_{61}R_{64}NC=O$;

$R_{44}$ is $R_{51}C=O$, $R_{62}R_{63}NSO_2$, or $(C=O)-(C=O)-R_{65}$;

$R_{14}$ and $R_{15}$ are selected from the group consisting of H, halogen, alkyl, or substituted alkyl;

$R_{19}$ is selected from the group consisting of H, alkyl, substituted alkyl, O-alkyl, O-substituted alkyl, $NR_{54}R_{55}$, $R_{56}C=O$; when L is O, S, or $NR_{13}$ then $R_{19}$ is not O-alkyl, O-substituted alkyl, $NR_{54}R_{55}$.

$R_{45}$ and $R_{46}$ are selected from the group consisting of H, halogen, alkyl, substituted alkyl, aryl, substituted aryl, cycloalkyl, heterocyclo, $R_{56}C=O$, $R_{57}OC=O$, $R_{58}NHC=O$, hydroxy, O-alkyl or O-substituted alkyl, $NR_{59}R_{60}$;

and any salts, solvates or hydrates thereof, with the proviso that
when Q is

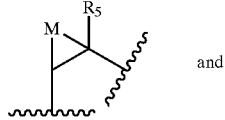

and

M is $CR_{45}R_{46}$ then W is only $NR_{16}$.

DETAILED DESCRIPTION OF PREFERRED EMBODIMENTS

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 2 to 20 carbon atoms, more preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, phenyl, substituted phenyl, heterocyclo, trifluoromethyl, trifluoromethoxy, hydroxy, alkoxy, cycloalkyoxy, heterocylooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g. $SO_2NH_2$), substituted sulfonamido, nitro, cyano, carboxy, carbamyl (e.g. $CONH_2$), substituted carbamyl (e.g. CONH alkyl, CONH aryl, CONH aralkyl or cases where there are two substituents on the nitrogen selected from alkyl, aryl or aralkyl), alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Where noted above where the substituent is further substituted it will be with halogen, alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl group bonded directly through an alkyl group, such as benzyl.

The term "substituted aryl" refers to an aryl group substituted by, for example, one to four substituents such as alkyl; substituted alkyl, halo, trifluoromethoxy, trifluoromethyl, hydroxy, alkoxy, cycloalkyloxy, heterocylooxy, alkanoyl, alkanoyloxy, amino, alkylamino, aralkylamino, cycloalkylamino, heterocycloamino, dialkylamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by halo, hydroxy, alkyl, alkoxy, aryl, substituted aryl, substituted alkyl or aralkyl.

The term "cycloalkyl" refers to optionally substituted, saturated cyclic hydrocarbon ring systems, preferably containing 1 to 3 rings and 3 to 7 carbons per ring which may be further fused with an unsaturated $C_3$–$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heteroaryl", "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl groups as described above or one or more groups described above as alkyl substituents. Also included are smaller heterocyclos, such as, epoxides and aziridines.

The term "heteroatoms" shall include oxygen, sulfur and nitrogen.

The compounds of formula I and II may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be obtained, for example, by exchanging the carboxylic acid protons, if they contain a carboxylic acid, in compounds of formula I and formula II with the desired ion in a medium in which the salt precipitates or in an aqueous medium followed by evaporation. Other salts can be formed as known to those skilled in the art.

The compounds for formula I and formula II form salts with a variety of organic and inorganic acids. Such salts include those formed with hydrogen chloride, hydrogen bromide, methanesulfonic acid, hydroxyethanesulfonic acid, sulfuric acid, acetic acid, trifluoroacetic acid, maleic acid, benzenesulfonic acid, toluenesulfonic acid and various others (e.g., nitrates, phosphates, borates, tartrates, citrates, succinates, benzoates, ascorbates, salicylates and the like). Such salts are formed by reacting a compound of formula I and formula II in an equivalent amount of the acid in a medium in which the salt precipitates or in an aqueous medium followed by evaporation.

In addition, zwitterions ("inner salts") are formed.

Compounds of formula I and formula II may also have prodrug forms. Any compound that will be converted in vivo to provide the bioactive agent (i.e., the compound of formula I and formula II) is a prodrug within the scope and spirit of the invention.

For example compounds of formula I and formula II may form a carboxylate ester moiety. The carboxylate esters are conveniently formed by esterifying any of the carboxylic acid functionalities found on the disclosed ring structure(s).

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 42, p. 309–396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, p. 113–191 (1991);

c) H. Bundgaard, *Advanced Drug Delivery Reviews*, 8, 1–38 (1992);

d) H. Bundgaard, et al., *Journal of Pharmaceutical Sciences*, 77, 285 (1988); and e) N. Kakeya, et al., *Chem Phar Bull*, 32, 692 (1984).

It should further be understood that solvates (e.g., hydrates) of the compounds of formula I and II are also within the scope of the present invention. Methods of solvation are generally known in the art.

Use and Utility

Compounds of formula I and formula II are microtubule-stabilizing agents. They are thus useful in the treatment of a variety of cancers, including (but not limited to) the following;

carcinoma, including that of the bladder, breast, colon, kidney, liver, lung, ovary, pancreas, stomach, cervix, thyroid and skin; including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma;

hematopoietic tumors of myeloid lineage, including acute and chronic myelogenous leukemias and promyelocytic leukemia;

tumors of mesenchymal origin, including fibrosarcoma and rhabdomyoscarcoma;

other tumors, including melanoma, seminoma, tetratocarcinoma, neuroblastoma and glioma;

tumors of the central and peripheral nervous system, including astrocytoma, neuroblastoma, glioma, and schwannomas;

tumors of mesenchymal origin, including fibrosarcoma, rhabdomyoscaroma, and osteosarcoma; and other tumors, including melanoma, xenoderma pigmentosum, keratoactanthoma, seminoma, thyroid follicular cancer and teratocarcinoma.

Compounds of formula I and formula II may also inhibit tumor angiogenesis, thereby affecting the growth of tumors. Such anti-angiogenesis properties of compounds of formula I and formula II may also be useful in the treatment of certain forms of blindness related to retinal vascularization, arthritis, especially inflammatory arthritis, multiple sclerosis, restinosis and psoriasis.

Compounds of formula I and formula II may induce or inhibit apoptosis, a physiological cell death process critical for normal development and homeostasis. Alterations of apoptotic pathways contribute to the pathogenesis of a variety of human diseases. Compounds of formula I and formula II, as modulators of apoptosis, will be useful in the treatment of a variety of human diseases with aberrations in apoptosis including cancer (particularly, but not limited to follicular lymphomas, carcinomas with p53 mutations, hormone dependent tumors of the breast, prostrate and ovary, and precancerous lesions such as familial adenomatous polyposis), viral infections (including but not limited to herpesvirus, poxvirus, Epstein-Barr virus, Sindbis virus and adenovirus), autoimmune diseases (including but not limited to systemic lupus erythematosus, immune mediated glomerulonephritis, rheumatoid arthritis, psoriasis, inflammatory bowel diseases and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), AIDS, myelodysplastic syndromes, aplastic anemia, ischemic injury associated myocardial infarctions, stroke and reperfusion injury, arrhythmia, atherosclerosis, toxin-induced or alcohol induced liver diseases, hematological diseases (including but not limited to chronic anemia and aplastic anemia), degenerative diseases of the musculoskeletal system (including but not limited to osteoporosis and arthritis), aspirin-sensitive rhinosinusitis, cystic fibrosis, multiple sclerosis, kidney diseases, and cancer pain.

The compounds of this invention are also useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I and II can be used sequentially with known anticancer or cytotoxic agents and treatment, including radiation when a combination formulation is inappropriate. Especially useful are cytotoxic drug combinations wherein the second drug chosen acts in a different phase of the cell cycle, e.g. S phase, than the present compounds of formula I and formula II which exert their effects at the $G_2$-M phase.

The present compounds may exist as multiple optical, geometric, and stereoisomers. Included within the present invention are all such isomers and mixtures thereof in the racemic form.

The compounds of this invention can be formulated with a pharmaceutical vehicle or diluent for oral, intravenous or subcutaneous administration. The pharmaceutical composition can be formulated in a classical manner using solid or liquid vehicles, diluents and additives appropriate to the desired mode of administration. Orally, the compounds can be administered in the form of tablets, capsules, granules, powders and the like. The compounds are administered in a dosage range of about 0.05 to 200 mg/kg/day, preferably less than 100 mg/kg/day, in a single dose or in 2 to 4 divided doses.

Methods of Preparation

Compounds of formula I and formula II are prepared by the following schemes.

SCHEME 1

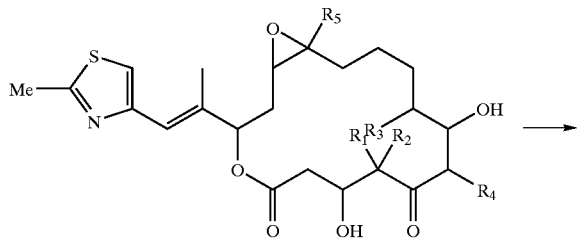

1A

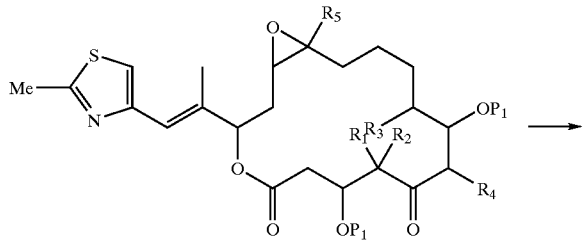

1B

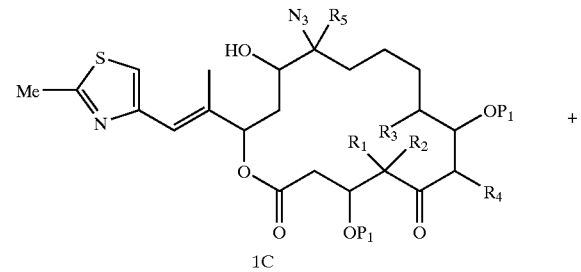

1C

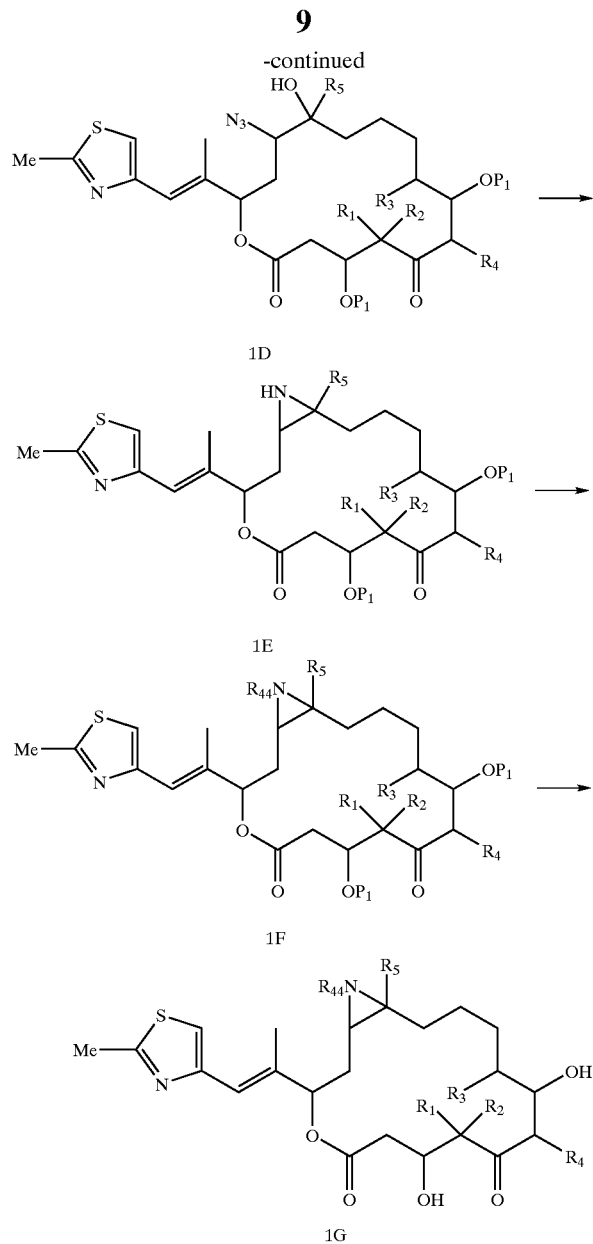

Compounds of formula I where X is O, W is O, and Q is an aziridine group (I.e., M is $NR_{44}$) can be prepared as outlined in Scheme 1. Compounds of formula 1A can be obtained from a fermentation process (see Angew. Chem. Int. Ed. Engl., 1996, 35, No. 13/14). A compound of formula 1B, where $P_1$ is an oxygen protecting group such as triethylsilyl, can be prepared from a compound of formula 1A by known methods (See for example: Corey, E. J.; Venkateswarlu, A., J. Am. Chem. Soc., (1972) 94, 6190). Compounds of formula 1C and 1D are prepared by treatment with an azide, such as sodium azide, in polar solvents such as DMF. A compound of formula 1E can be prepared from compounds of formulas 1C and 1D by the Staudinger reaction (See for example: Ittah, Y., et al., J. Org. Chem., (1978) 43, 4271). A compound of formula 1F where $R_{44}$ is not H can be prepared from a compound of formula 1E using methods known in the art. Deprotection of a compound of formula 1F using, for example when $P_1$ is a triethylsilyl group, hydrogen fluoride in acetonitrile or tetra-n-butylammonium fluoride in THF provides a compound of formula I (1G) where X is O, W is O, Q is an aziridine group (M is $NR_{44}$), and $R_1$, $R_2$, $R_3$, $R_4$ and $R_5$ are defined as described above.

Scheme 2

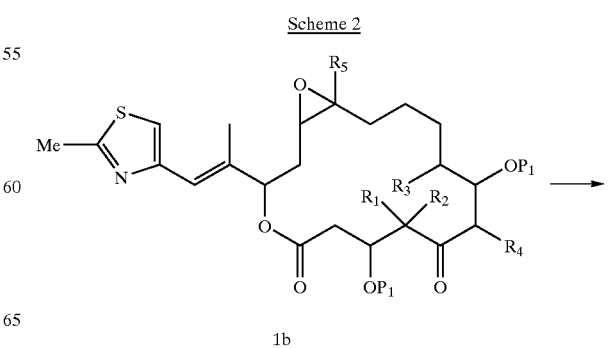

1b

-continued

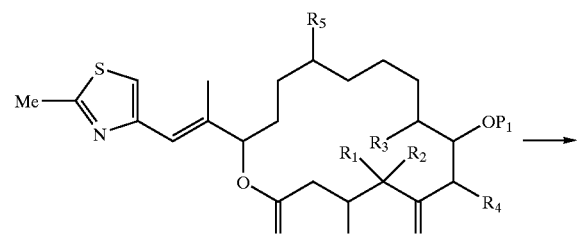

2A

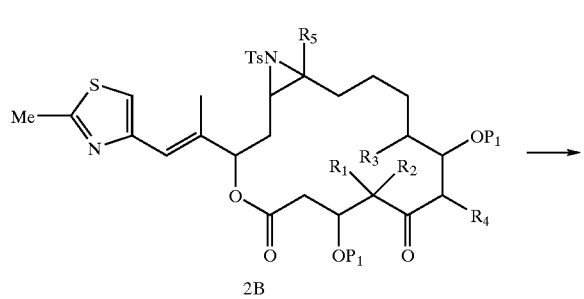

2B

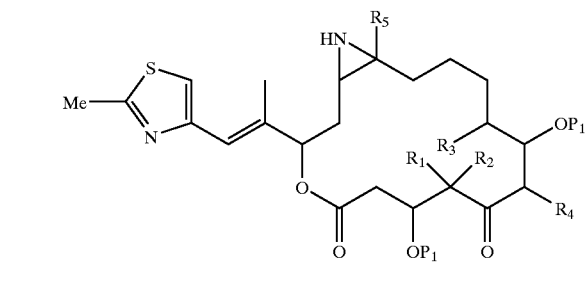

1E

Alternatively, a compound of formula 1E can be prepared as shown in Scheme 2. A compound of formula 2A, where $P_1$ is an oxygen protecting group such as triethylsilyl, can be prepared from a compound of formula 1B by reaction of tungsten (VI) chloride and n-butyllithium (See for example: Sharpless, K. B., et al., *J. Am. Chem. Soc.,* (1972) 94, 6538) in THF. A compound of formula 2B can be prepared from a compound of formula 2A by addition of a N-toluenesulfonamido group according to the method of Evans (i.e., Evans, D. A., et al., *J. Org. Chem.,* (1991) 56, 6744). Deprotection of a compound of formula 2B using samarium iodide in THF/1,3-dimethyl-3,4,5,6-tetrahydro-2 (1H)-pyrimidinone provides a compound of formula 1E (See for example: Vedejs, E., et al., *J. Org. Chem.,* (1994) 59, 1602). Furthermore, a compound of formula 1B can be prepared from a compound of formula 2A by oxidation (See for example: Balog, A., et al., *Angew. Chem. Int. Ed. Engl.,* (1996) 35, 2801).

Scheme 3

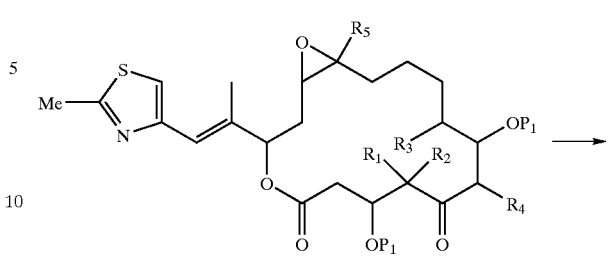

1B

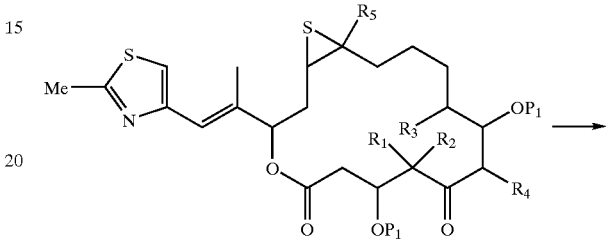

4A

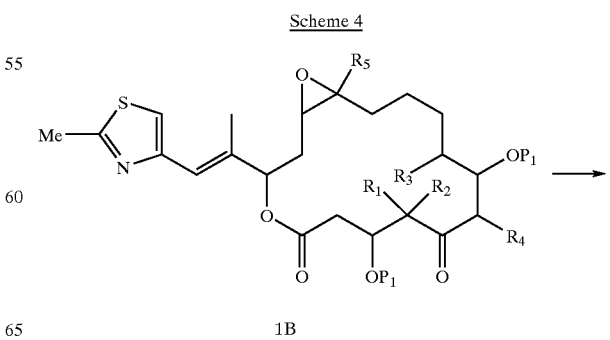

4B

Compounds of formula I where X is O, W is O, and Q is a thiirane (i.e., M is S) can be prepared as outlined in Scheme 3. A compound of formula 4A can be prepared from a compound of formula 1B using potassium thiocyanate in alcoholic solution (See for example: Culvenor, C. C. J., et al., *J. Chem. Soc.,* (1946) 1050). Deprotection of a compound of formula 4A using, for example when $P_1$ is a triethylsilyl group, hydrogen fluoride in acetonitrile or tetra-n-butylammonium fluoride in THF provides a compound of formula I (4B) where X is O, W is O, Q is a thiirane group (i.e., M is S), and $R_1$, $R_2$, $R_3$, $R_4$ and $R_5$ are defined as described above. Mild oxidation of a compound of formula 4A using stoichiometric or excess 3-chloroperoxybenzoic acid provides compounds of formula I where M is a S=O or $SO_2$ group, respectively.

Scheme 4

1B

-continued

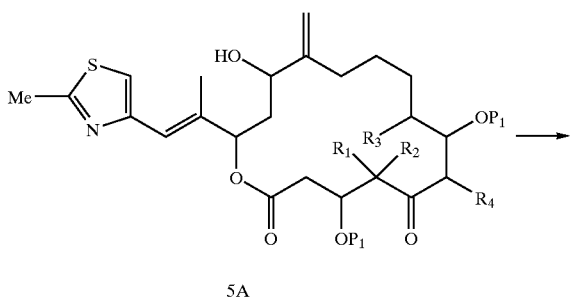

5A

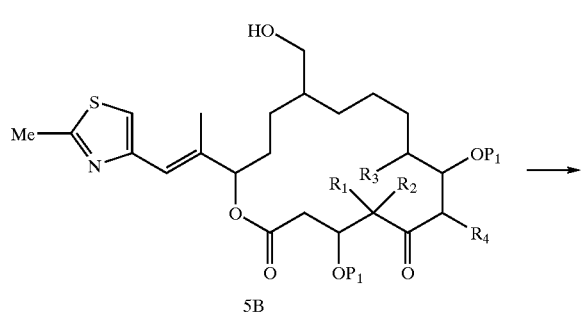

5B

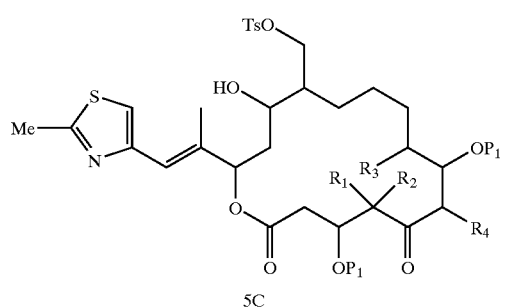

5C

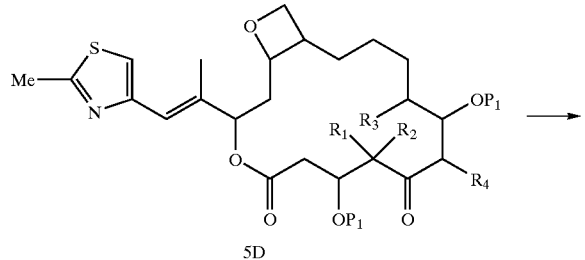

5D

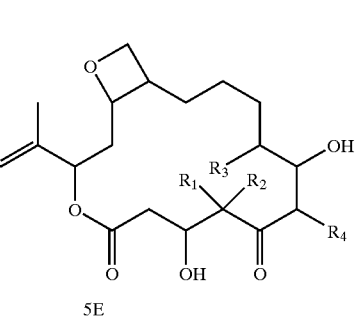

5E

Compounds of formula I where X is O, W is O, and Q is an oxetane can be prepared as outlined in Scheme 4. A compound of formula 5A can be prepared from a compound of formula 1B, where $R_5$ is a methyl group, by using lithium 2,2,6,6-tetramethylpiperidide and diethylaluminum chloride in benzene (See for example: Paquette, L. A., et al., *J. Org. Chem.*, (1990) 55, 1589). A compound of formula 5B can be prepared from a compound of formula 5A by hydroboration and oxidation (See for example: Uzarewicz, A., et al., *Rocz. Chem.*, (1977) 51, 723). A compound of formula 5C can be prepared from a compound of formula 5B by treatment with p-toluenesulfonylchloride (TsCl) in pyridine. A compound of formula 5D can be prepared from a compound of formula 5C by an intramolecular Williamson reaction according to the method of Moulines (i.e., Moulines, B. J., Leclercq, D., Picard, P., *Synthesis*, (1981) 550). Deprotection of a compound of formula 5D using, for example when $P_1$ is a triethylsilyl group, hydrogen fluoride in acetonitrile or tetra-n-butylammonium fluoride in THF provides a compound of formula I (5E) where X is O, W is O, Q is an oxetane group, and $R_1$, $R_2$, $R_3$, $R_4$ and $R_5$ are defined as described above.

Scheme 5

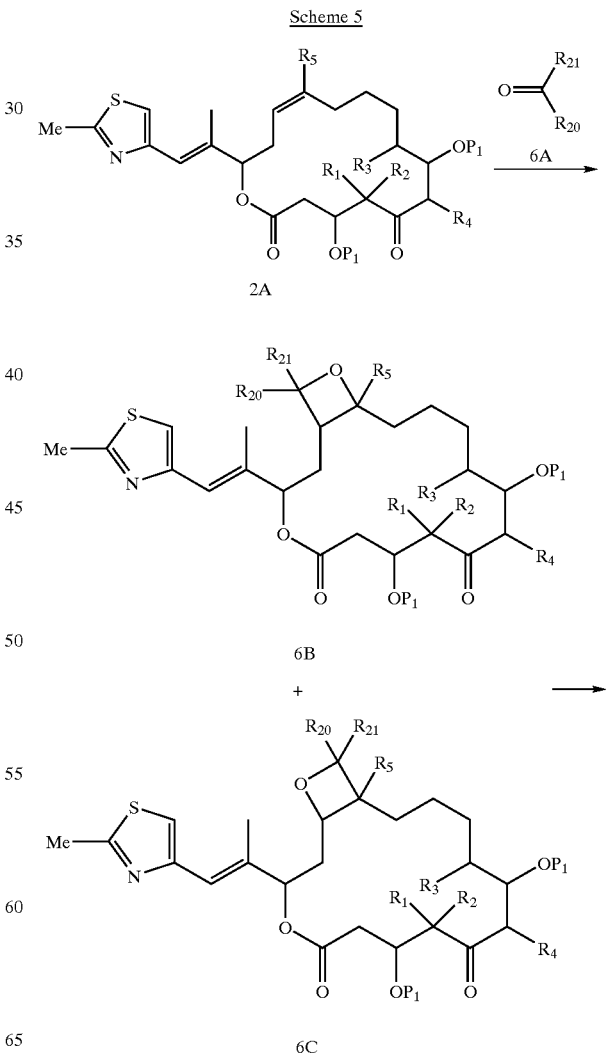

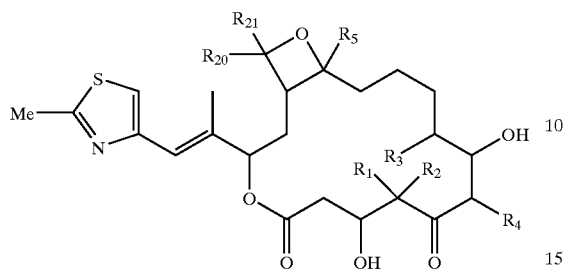

6D

+

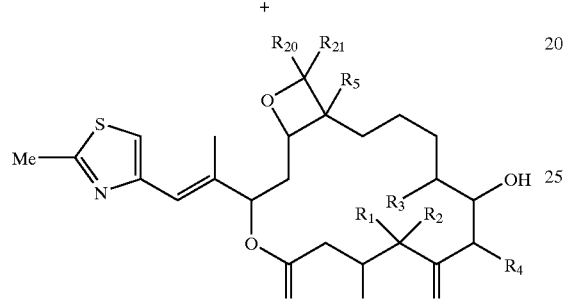

6E

Alternatively, compounds of formula I where Q is an oxetane can be prepared as outlined in Scheme 5. Compounds of formula 6B and 6C can be prepared from a compound of formula 2A by Paterno-Buchi reaction of a carbonyl compound of formula 6A (See for example: Arnold, D. R., et al., *Org. Photochem. Synth.* (1971) 1, 51). Deprotection of compounds of formula 6B and 6C using, for example when $P_1$ is a triethylsilyl group, hydrogen fluoride in acetonitrile or tetra-n-butylammonium fluoride in THF provides a compound of formula I (6D and 6E) where X is O, W is O, Q is an oxetane group, and $R_1$, $R_2$, $R_3$, $R_4$ and $R_5$ are defined as described above.

Scheme 6

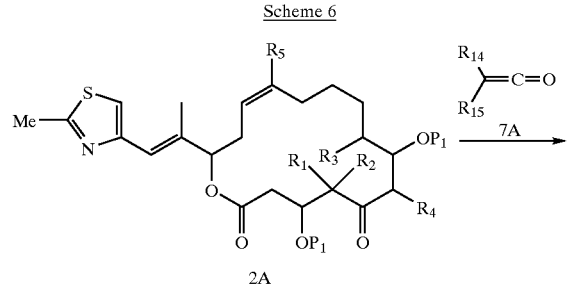

2A

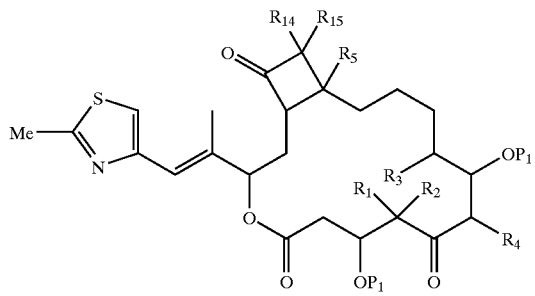

7B

+

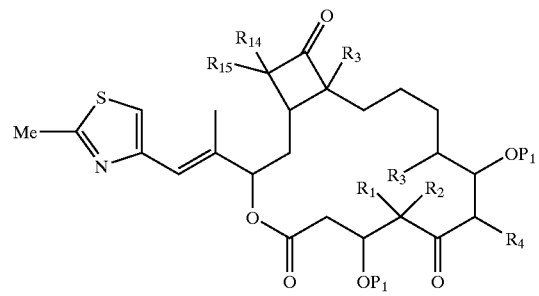

7C

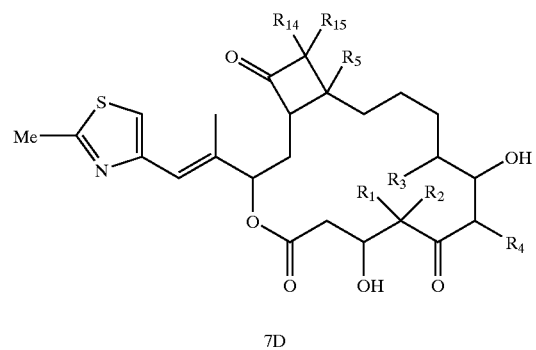

7D

+

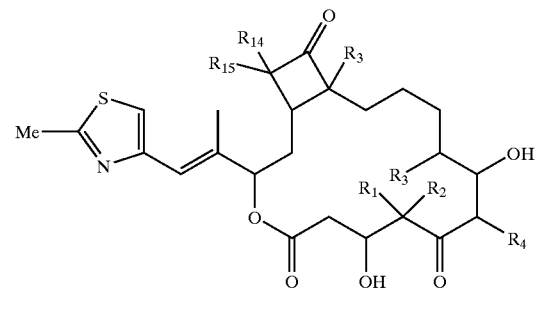

7E

Compounds of formula I where X is O, W is O, and Q is a cyclobutane (i.e., L is $CR_{14}R_{15}$) can be prepared as outlined in Scheme 6. Compounds of formula 7B and 7C can be prepared from a compound of formula 2A by [2+2] cycloaddition of a substituted ketene compound of formula 7A (See for example: Krapcho, A. P. *J. Org. Chem.*, (1966) 31, 2030). Deprotection of compounds of formula 7B and 7C using, for example when $P_1$ is a triethylsilyl group, hydrogen fluoride in acetonitrile or tetra-n-butylammonium fluoride in THF provides a compound of formula I (7D and 7E) where X is O, W is O, Q is an cyclobutane group, and $R_1$, $R_2$, $R_3$, $R_4$ and $R_5$ are defined as described above.

Compounds of formula I where X is O, W is O, and Q is a 5-membered ring heterocycle can be prepared as outlined in Scheme 7. Compounds of formula 8A and 8B can be prepared from a compound of formula 1B, where $R_5$ is a hydrogen, by reaction of magnesium bromide diethyl etherate in dichloromethane. Compounds of formula 8C and 8D can be prepared from compounds of formula 8A and 8B by pyridinium chlorochromate oxidation in dichloromethane (See for example: White, J. D., et al., *J. Org. Chem.*, (1995) 12, 3600). Compounds of formula 8F and 8G can be prepared from compounds of formula 8C and 8D by addition of a substituted thioamide of formula 8E (See for example: Cauvin, P. *Compt. Rend.*, (1973) 276C, 1453). Deprotection of compounds of formula 8F and 8G using, for example when $P_1$ is a triethylsilyl group, hydrogen fluoride in acetonitrile or tetra-n-butylammonium fluoride in THF provides a compound of formula I (8H and 8I) where X is O, W is O, Q is a 5-membered heterocycle, and $R_1$, $R_2$, $R_3$, $R_4$ and $R_5$ are defined as described above.

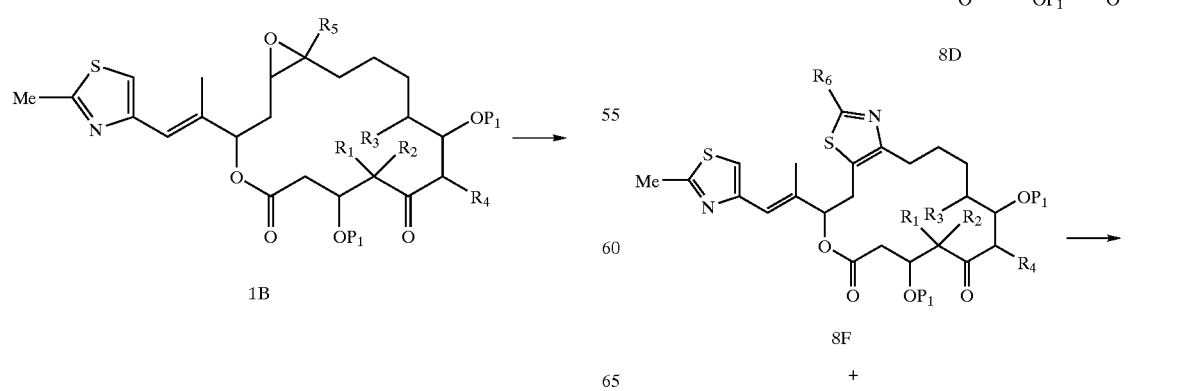

Scheme 7

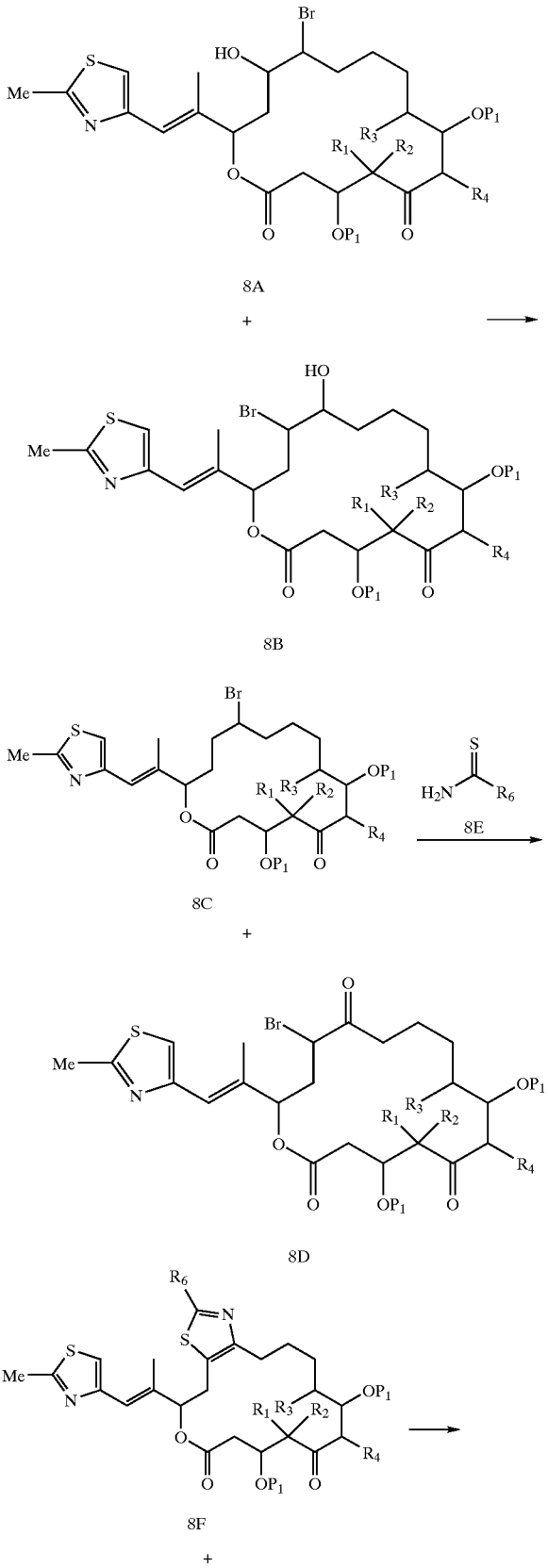

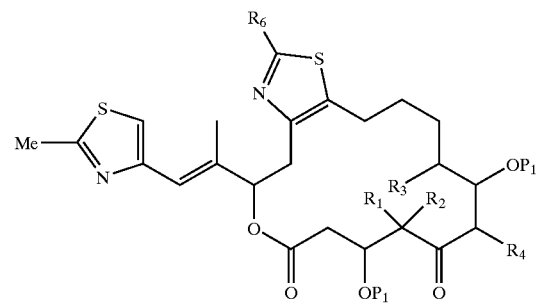
8G
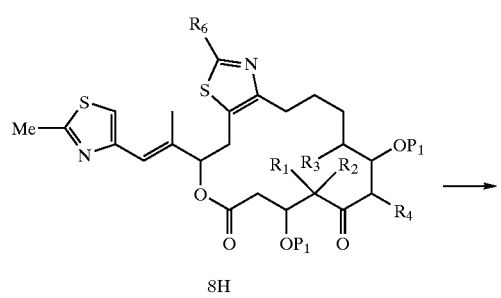
8H
+
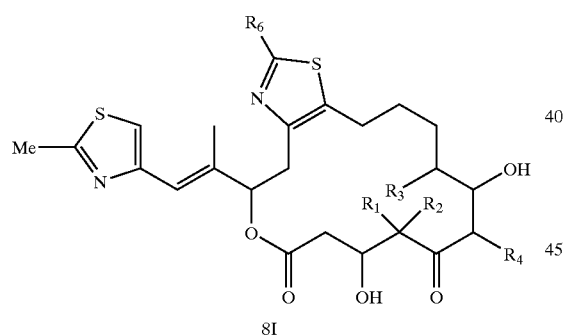
8I
Scheme 8
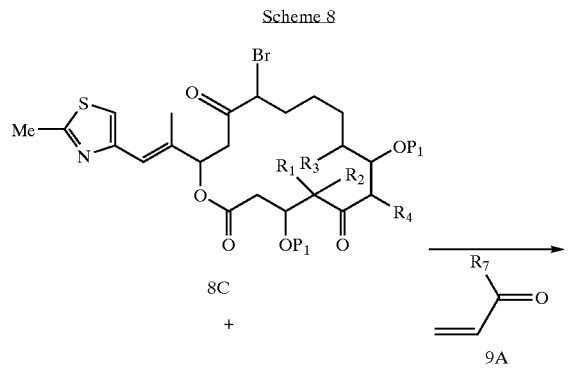
8C
+
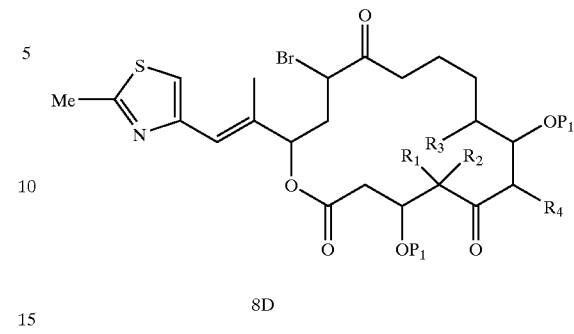
8D
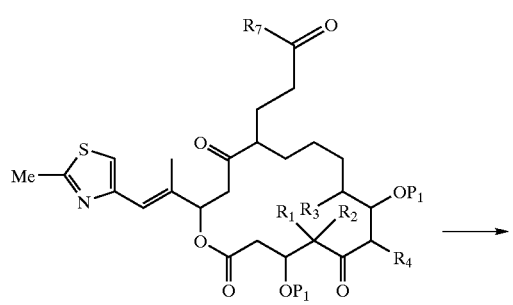
9B
+
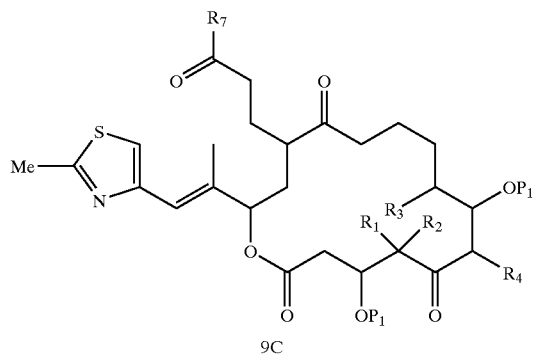
9C
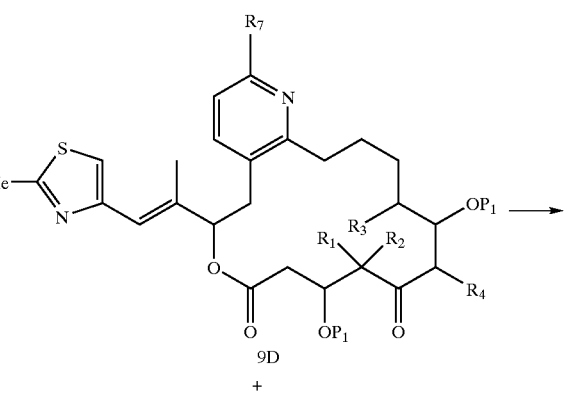
9D
+

-continued

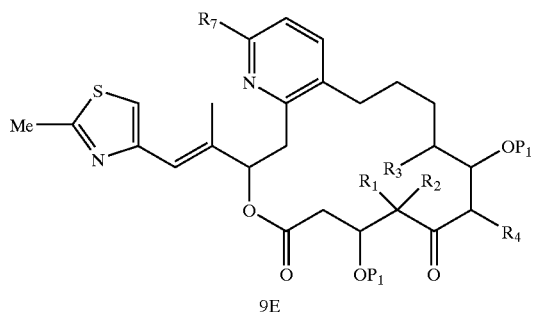

9E

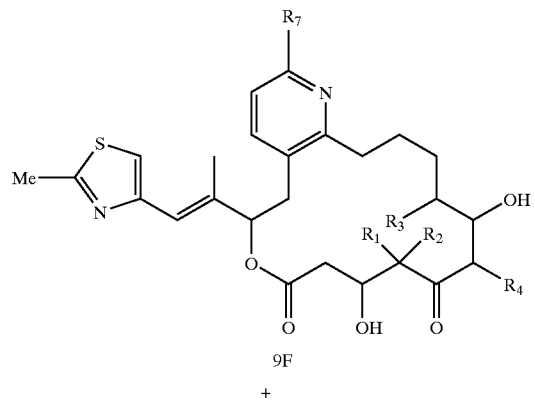

9F

+

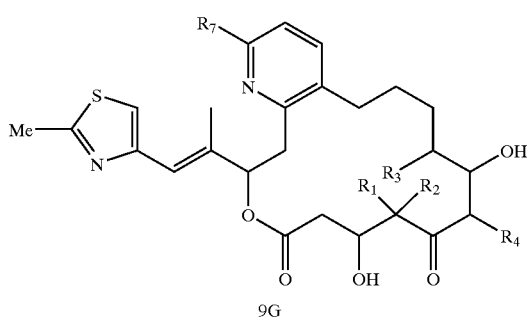

9G

Compounds of formula I where X is O, W is O, and Q is a 6-membered ring heterocycle can be prepared as outlined in Scheme 8. Compounds of formula 9B and 9C can be prepared from compounds of formula 8C and 8D by reaction of diethyl zinc in THF with a Michael acceptor of formula 9A according to the method of Hansen (i.e., Hansen, M. M., et al., *Organometallics,* (1987) 6, 2069). Compounds of formula 9D and 9E can be prepared from compounds of formula 9B and 9C by addition of hydroxyl amine in ethanol (See for example: *Chemistry of Heterocyclic Compounds,* Wiley: New York, 1974; Vol. 14, Parts 1–5). Deprotection of compounds of formula 9D and 9E using, for example when $P_1$ is a triethylsilyl group, hydrogen fluoride in acetonitrile or tetra-n-butylammonium fluoride in THF provides a compound of formula I (9F and 9G) where X is O, W is O, Q is a 6-membered heterocycle, and $R_1$, $R_2$, $R_3$, $R_4$ and $R_5$ are defined as described above.

Scheme 9

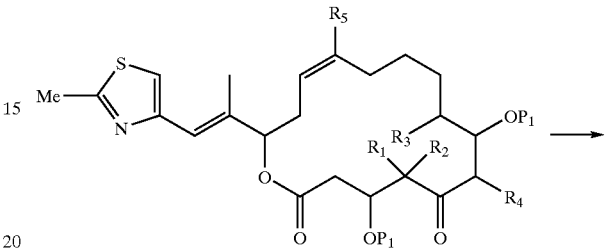

2A

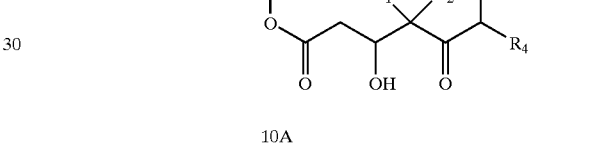

10A

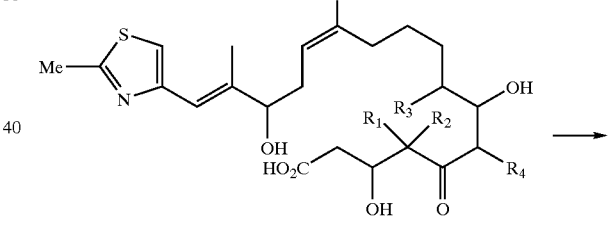

10B

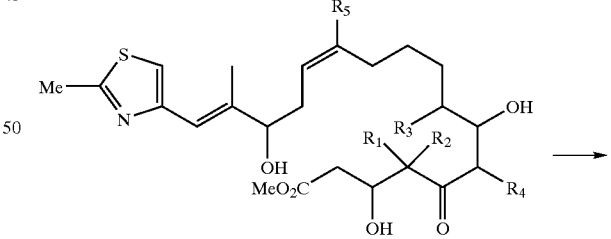

10C

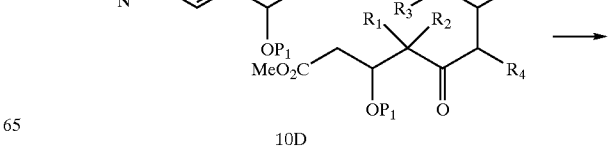

10D

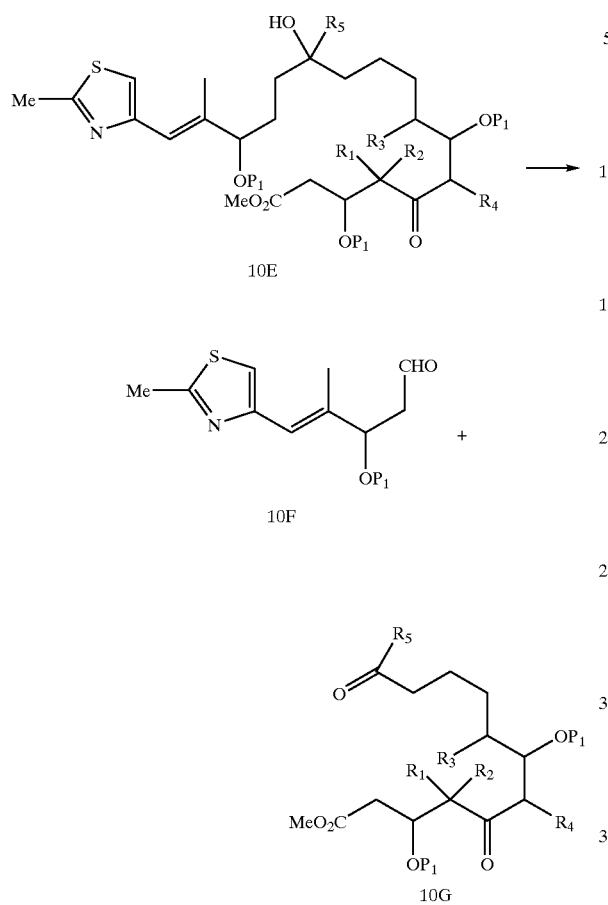

A compound of formula 10G that is used for the preparation of compounds of formula I where X is O, W is O, and G is as defined above can be prepared as outlined in Scheme 9. Deprotection of a compound of formula 2A using, for example when $P_1$ is a triethylsilyl group, hydrogen fluoride in acetonitrile or tetra-n-butylammonium fluoride in THF provides a compound of formula 10A. A compound of formula 10B can be prepared from a compound of formula 10A by pig-liver esterase mediated hydrolysis (See for example: Ohno, M., et al., *Tetrahedron*, (1984) 40, 145). A compound of formula 10C can be prepared from a compound of formula 10B by reaction of (trimethylsilyl) diazomethane in methanol and toluene (See for example: Hashimoto, N., et al., *Chem. Pharm. Bull.*, (1981) 1397). A compound of formula 10D can be prepared from a compound of formula 10C by addition of t-butyldimethylsilyltriflate and 2,6-lutidine in dichloromethane (See for example: Askin, D., et al., *J. Org. Chem.*, (1987) 52, 622). A compound of formula 10E can be prepared from a compound of formula 10D by reaction of AD-mix-α according to the method of Sharpless (i.e., Sharpless, K. B., et al., *J. Org. Chem.*, (1992) 57, 2768). Compounds of formula 10F and 10G can be prepared from a compound of formula 10E by oxidative cleavage using lead tetraacetate in ethyl acetate (See for example: C. A. Bunton in K. B. Wiberg, ed., *Oxidation in Organic Chemistry*, Part A, Academic Press, New York, 1965, p. 367). Alternatively, a compound of formula 10G can be prepared from a compound of formula 10D by ozonolysis.

Compounds of formula I where X is O, W is O, and G is a 1,2-disubstituted olefin can be prepared as outlined in Scheme 10. A compound of formula 11C can be prepared from compound of formula 11A and 11B using standard Wittig olefination known in the art (See for example: Meng, D., et al., *J. Org. Chem.*, (1996) 61, 7999). A compound of formula 11D can be prepared from a compound of formula 11C by addition of an allyl metal reagent such as allylmagnesium bromide (Hoffmann, R. W. *Angew. Chem. Int. Ed., Engl.*, (1982) 21, 555). A compound of formula 11E, where $P_2$ is a triethylsilyl group, can be prepared from a compound of formula 11D by reaction of triethylsilyl chloride in DMF according to the method of Corey (See for example: Corey, E. J.; Venkateswarlu, A., *J. Am. Chem. Soc.*, (1972) 94, 6190). A compound of formula 11F can be prepared from a compound of formula 11E by reaction of AD-mix-α according to the method of Sharpless (i.e., Sharpless, K. B., et al., *J. Org. Chem.*, (1992) 57, 2768). A compound of formula 11G can be prepared from a compound of formula 11F by oxidative cleavage using lead tetraacetate in ethyl acetate (See for example: C. A. Bunton in K. B. Wiberg, ed., *Oxidation in Organic Chemistry*, Part A, Academic Press, New York, 1965, p. 367). A compound of formula 11H can be prepared from a compound of formula 11I by using a reducing agent such as sodium borohydride in methanol. A compound of formula 11I can be prepared from a compound with a formula 11H by reaction of iodine, imidazole and triphenylphosphine in toluene. A compound of formula 11J can be prepared from compound of formula 11I by reaction of triphenylphosphine in refluxing acetonitrile. A compound of formula 11K can be prepared from compounds of formula 11J and 10G using standard Wittig olefination (See for example: Bestmann, K. H., et al., *Chem. Ber.* (1979)112, 1923). A compound of formula 11L can be prepared from a compound of formula 11K by selective deprotection using AcOH in THF. A compound of formula 11M can be prepared from a compound of formula 11L by reaction of LiOH in t-butanol and water. A compound of formula 11P can be prepared from a compound of formula 11M using typical macrolactonization coupling reagents such as 2,4,6-trichlorobenzoyl chloride, triethylamine, and 4-dimethylaminopyridine (See for example: Inanaga, J., et al., *Bull. Chem. Soc. Jpn.*, (1979) 52, 1989). A compound of formula 11Q can be prepared from a compound of formula 11P by reaction of 1,1,1-trifluoroacetone according to the method of Yang (Yang, D., et al., *J. Org. Chem.*, (1995) 60, 3887). A compound of formula I (11R) where X is O, W is O, G is a 1,2-disubstituted olefin, and $R_1$, $R_2$, $R_3$, $R_4$ and $R_5$ are defined as described above can be prepared from compounds of formula 11P and 11Q as described in Schemes 1–9.

Scheme 10
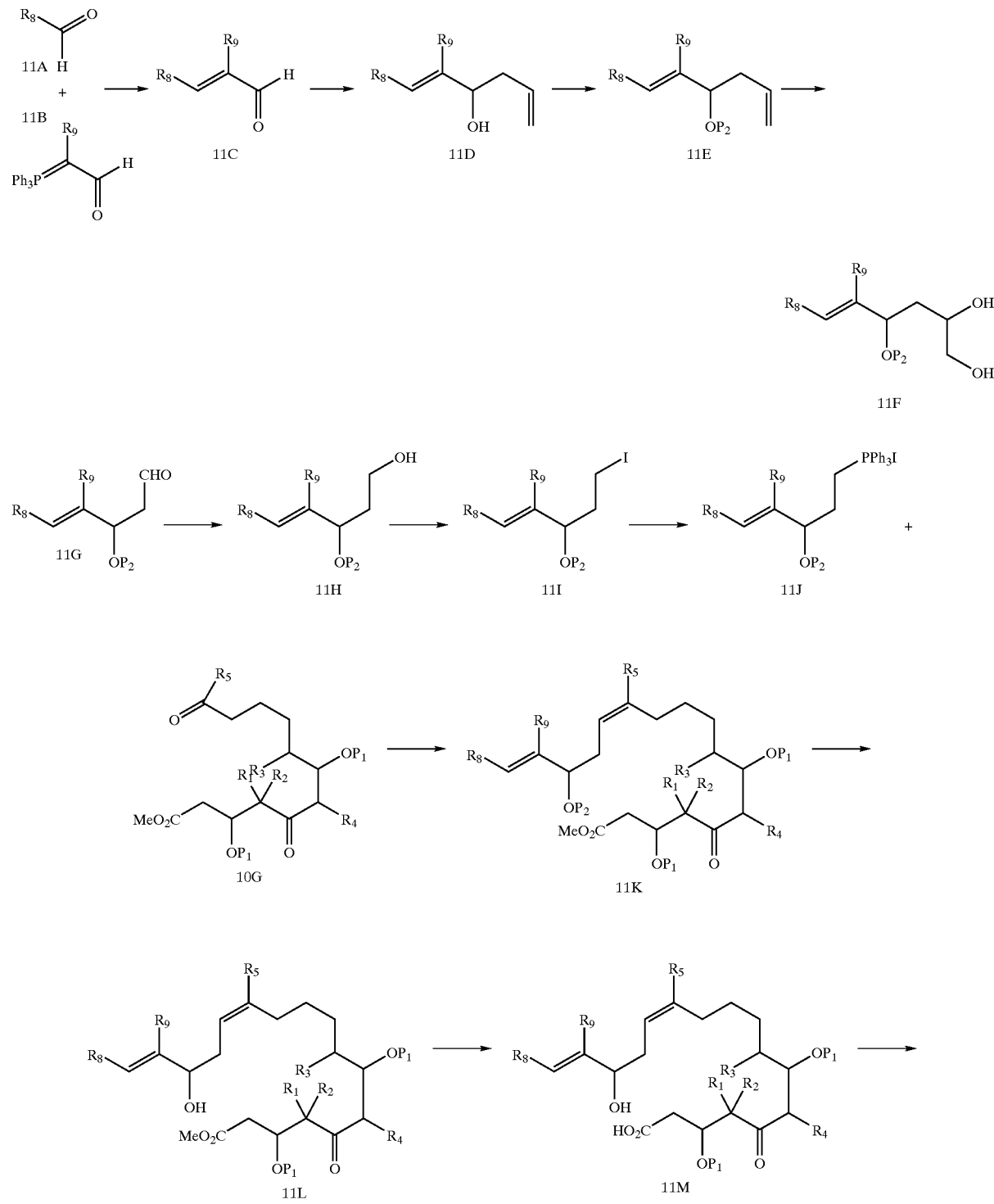

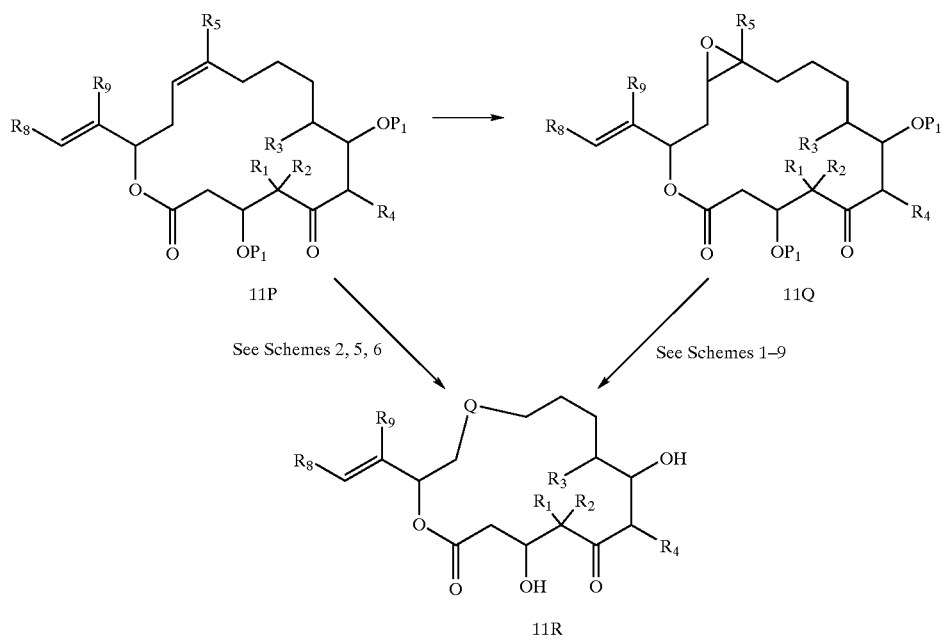

Scheme 11

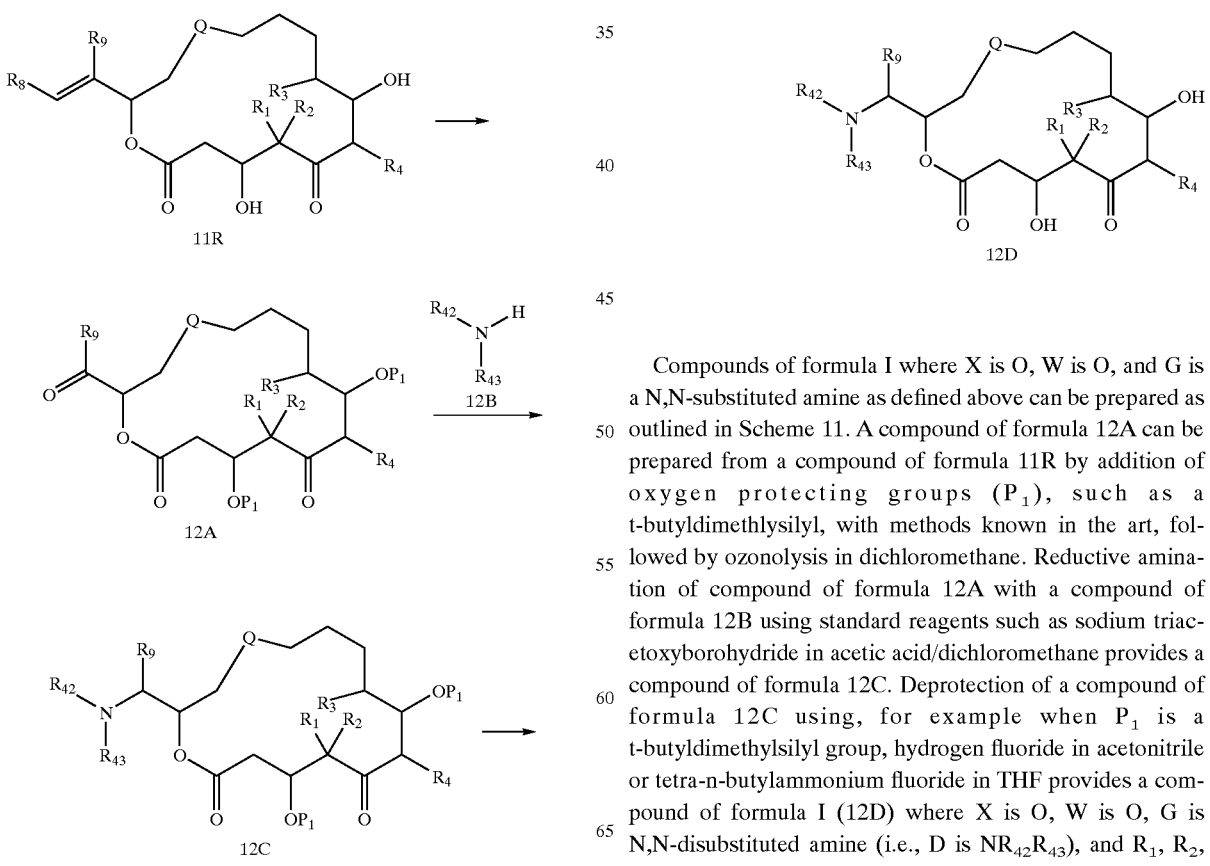

Compounds of formula I where X is O, W is O, and G is a N,N-substituted amine as defined above can be prepared as outlined in Scheme 11. A compound of formula 12A can be prepared from a compound of formula 11R by addition of oxygen protecting groups ($P_1$), such as a t-butyldimethlysilyl, with methods known in the art, followed by ozonolysis in dichloromethane. Reductive amination of compound of formula 12A with a compound of formula 12B using standard reagents such as sodium triacetoxyborohydride in acetic acid/dichloromethane provides a compound of formula 12C. Deprotection of a compound of formula 12C using, for example when $P_1$ is a t-butyldimethylsilyl group, hydrogen fluoride in acetonitrile or tetra-n-butylammonium fluoride in THF provides a compound of formula I (12D) where X is O, W is O, G is N,N-disubstituted amine (i.e., D is $NR_{42}R_{43}$), and $R_1$, $R_2$, $R_3$, $R_4$ and $R_5$ are defined as described above.

Scheme 12

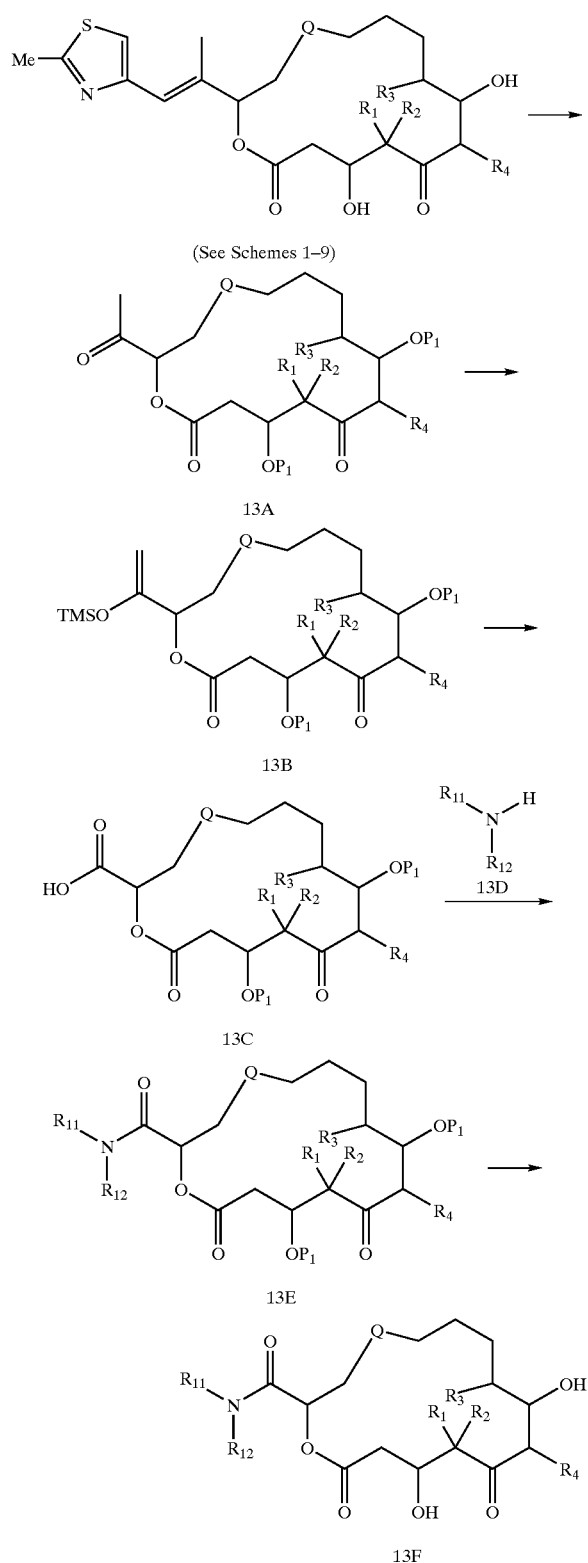

Compounds of formula I where X is O, W is O, and G is a N,N-substituted amide as defined above can be prepared as outlined in Scheme 12. A compound of formula 13A can be prepared from a compound of formula I where G is 1-methyl-2-(2-methyl-4-thiazolyl)ethenyl by protection with triethylsilyl chloride ($P_1$ is triethylsilyl) in DMF using methods known in the art followed by ozonolysis in dichloromethane. A compound of formula 13B can be prepared from a compound of formula 13C by reaction of sodium bis(trimethlysilyl)amide in THF followed by addition of chlorotrimethylsilane to quench the intermediate lithium enolate (See for example: House, H. O., et al., *J. Org. Chem.*, (1971) 36, 2361). A compound of formula 13C can be prepared from a compound of formula 13B by ozonolysis. A compound of formula 13E can be prepared from compounds of formula 13C and 13D by standard amide bond coupling agents (i.e., DCC, BOP, EDC/HOBT, PyBrOP). Deprotection of a compound of formula 13E using, for example when $P_1$ is a triethylsilyl group, hydrogen fluoride in acetonitrile or tetra-n-butylammonium fluoride in THF provides a compound of formula I (13F) where X is O, W is O, G is N,N-disubstituted amide, and $R_1$, $R_2$, $R_3$, $R_4$ and $R_5$ are defined as described above.

Scheme 13

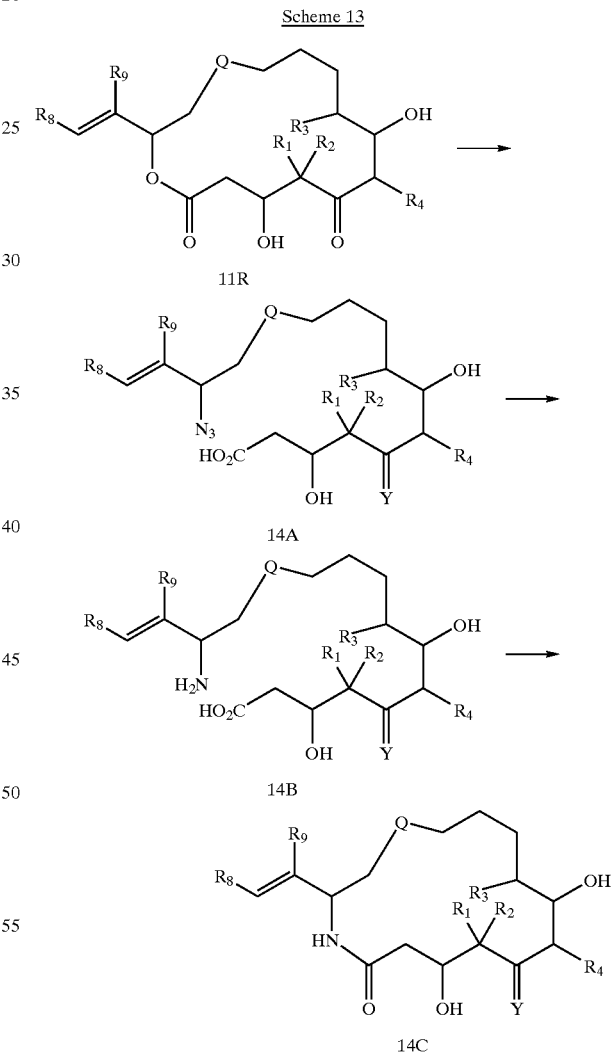

As shown in Scheme 13, compounds of formula I where W is $NR_{16}$ can be prepared from compounds of formula I where W is O. A compound of formula 14A can be prepared from a compound of formula 11R by reaction of sodium azide and tetrakis(triphenylphosphine)palladium in THF/water. Reduction of a compound of formula 14A using Adam's catalyst (PtO$_2$) or a trialkylphosphine in ethanol provides a compound of formula 14B. Intramolecular cyclization of compound of formula 14B using diphenylphosphoryl azide and sodium bicarbonate or 1-hydroxybenzotriazole and 1-(3-dimethylaminopropyl)-3-ethylcarbodiimide in DMF provides a compound of formula I (14C), where W is NR$_{16}$ (R$_{16}$ is H).

Compounds of formula II can be prepared from a compound of formula I, where B1 and B2 are hydroxyl groups, as shown in Scheme 14. A compound of formula 15A can be prepared from compounds of formula I by addition of formyl groups using standard conditions such as formic acid, triethylamine, acetic anhydride in dichloromethane. Elimination of a compound of formula 15A using 1,8-diazabicyclo[5.4.0]undec-7-ene in dichloromethane provides a compound of formula 15B. Deprotection of a compound of formula 15B using ammonia in methanol provides a compound of formula II (15C).

Scheme 14

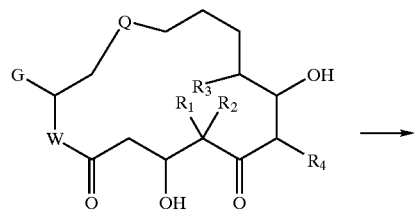

See Schemes 1–13

Scheme 15

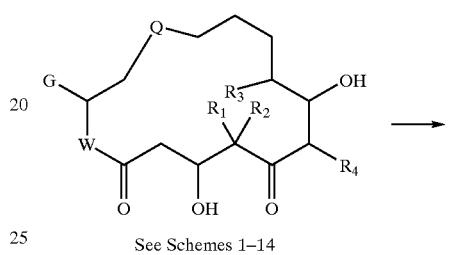

See Schemes 1–14

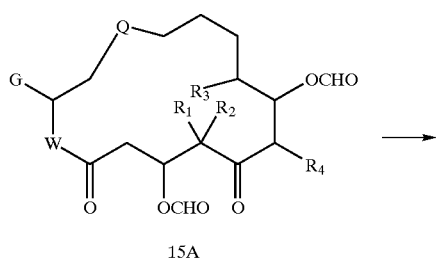

15A

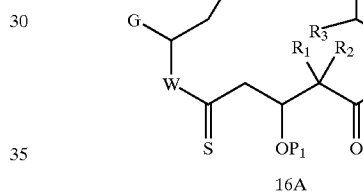

16A

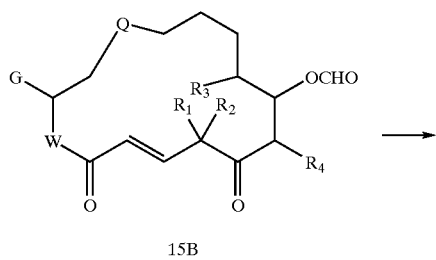

15B

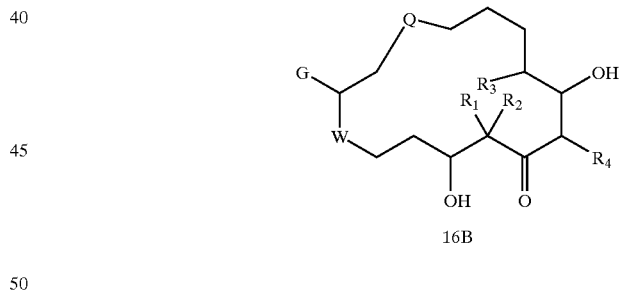

16B

As shown in Scheme 15, compounds of formula I where X is S or dihydrogen can be prepared from compounds of formula I where X is O. A compound of formula 16A, where X is S, can be prepared from a compound of formula I where X is O by reaction of triethylsilyl chloride(P$_1$) with methods known in the art, followed by the reaction of Lawesson's reagent in toluene (See for example: Nicolaou, K. C., et al., *J. Amer. Chem. Soc.*, (1990) 112, 6263). Reduction of a compound of formula I (16A) using triphenyltin hydride and 2,2'-azobisisobutyronitrile in benzene, followed by deprotection using standard methods such as acetic acid in THF (See for example: Nicolaou, K. C., et al., *Chem. Comm.*, (1995) 1583) provides a compound of formula I (16B), where X is dihydrogen.

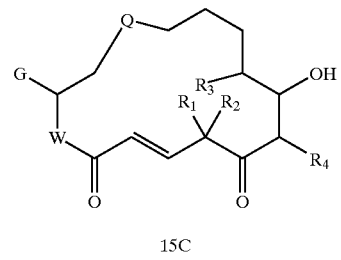

15C

Scheme 16

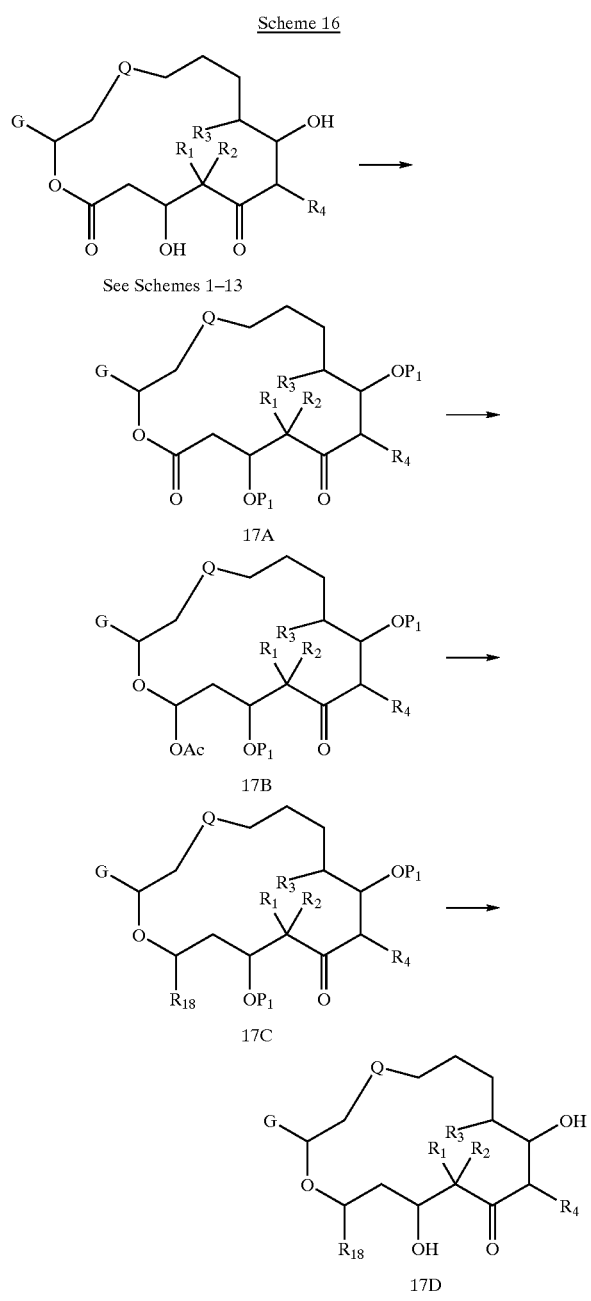

Alternatively, as shown in Scheme 16, compounds of formula I where X is H, $R_{18}$ can be prepared from compounds of formula I where X is O. A compound of formula 17A can be prepared from a compound of formula I by reaction of triethylsilyl chloride in DMF using standard methods known in the art. A compound of formula 17B can be prepared from a compound of formula 17A by reaction of diisobutylaluminum hydride followed by acetic anhydride according to the method of Dahanukar (i.e., Dahanukar, V. H., et al., *J. Org. Chem.* (1996) 61, 8317). Reaction of a compound of formula 17B with dialkylzinc, $(R_{18})_2Zn$, in dichloromethane according to the method of Rychnovsky (Rychnovsky, S. D., et. al., *J. Org. Chem.* (1997) 62, 6460) provides a compound of formula 17C. Deprotection of a compound of formula 17C using, for example when $P_1$ is a triethylsilyl group, hydrogen fluoride in acetonitrile or tetra-n-butylammonium fluoride in THF provides a compound of formula I (17D) where X is H, $R_{18}$ and $R_1$, $R_2$, $R_3$, $R_4$ and $R_5$ are defined as described above.

The hydroxyl groups of a compound of formula I, such as 1A (where $R_{1-4}$ are methyl and $R_6$ is 2-methyl-4-thiazolyl), can be optionally protected as, for example, triethylsilyl ethers using methods known in the art. A compound of formula 18B where X is halogen, can be prepared from a compound for formula 18A by treatment with certain metal halide salts such as magnesium bromide. A compound of formula 18C can be prepared from a compound of formula 18B by treatment with a metal azide salt such as lithium azide. A compound of formula 18D can be prepared from a compound of formula 18C by Mitsunobu reaction using, for example, triphenylphosphine and a carboxylic acid such as 4-nitrobenzoic acid. A compound of formula 18E can be prepared from a compound of formula 18D by hydrolysis or ammoniolysis of the ester group using, for example, a solution of ammonia in methanol. Optionally, a compound of formula 18E where P1 is an oxygen protecting group such as triethylsilyl can be deprotected using trifluoroacetic acid in dichloromethane, or other methods known in the art. Reduction of the azido group and subsequent cyclization of a compound of formula 18E with a reducing agent such as a triaryl- or trialkylphosphine provides a compound of formula I, such as 18F (where $R_{1-4}$ are methyl and $R_6$ is 2-methyl-4-thiazolyl).

Scheme 17

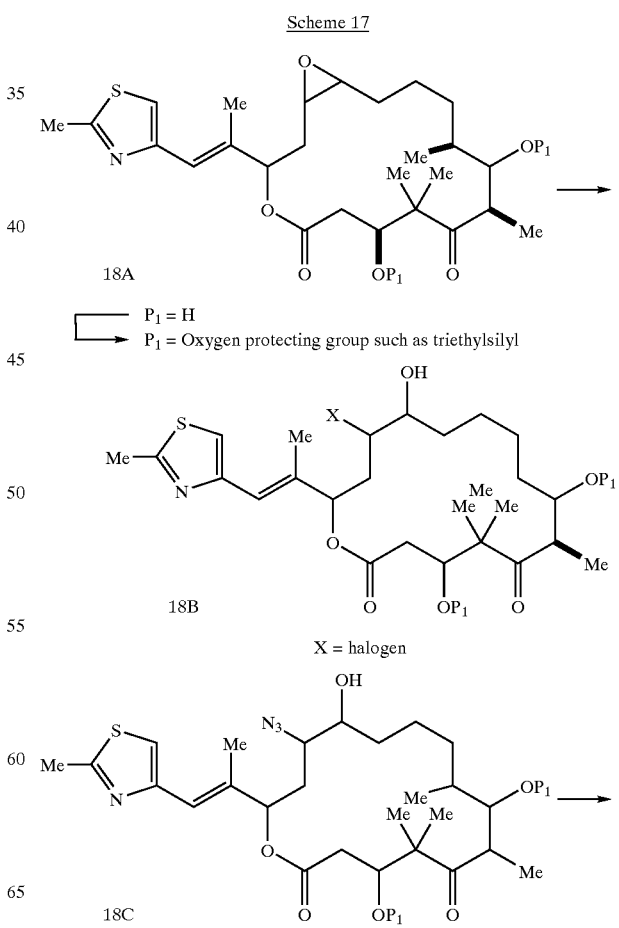

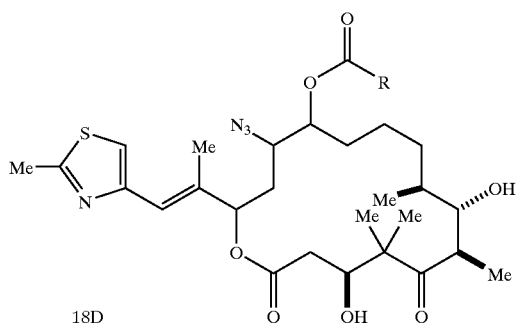

18D

R = 4-nitrophenyl, phenyl and the like

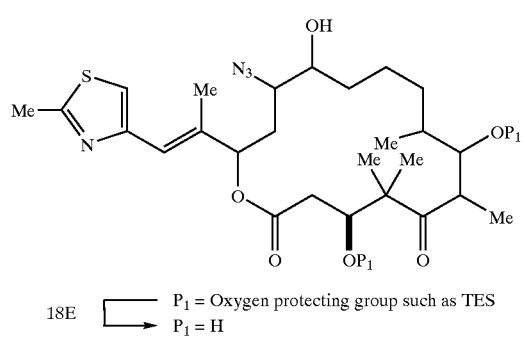

18E ⎡ P₁ = Oxygen protecting group such as TES
   ⎣ → P₁ = H

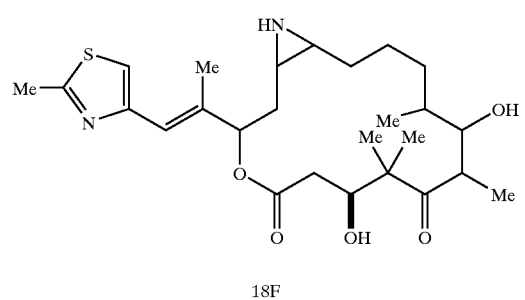

18F

Scheme 18

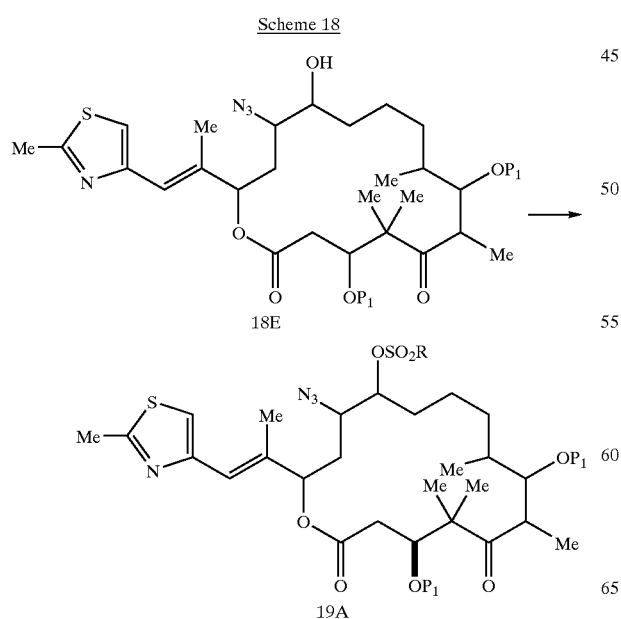

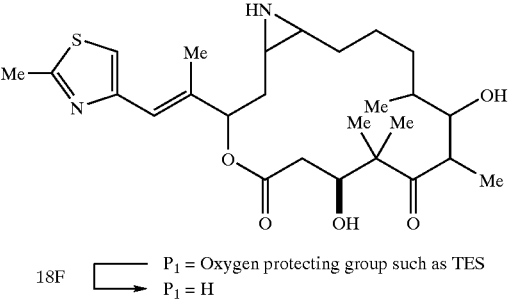

18F ⎡ P₁ = Oxygen protecting group such as TES
   ⎣ → P₁ = H

Alternatively, a compound of formula 18E where P1 is an oxygen protecting group, can be converted to a alkyl or aryl sulfonyl chloride. Reduction of the azido group and subsequent cyclization of a compound of formula 19A using a reducing agent such as a triaryl- or trialkylphosphine or with hydrogen and Lindlar's catalyst (Pd, CaCO₃/Pb) provides a compound of formula I such as 18F (where $R_{1-4}$ are methyl and $R_6$ is 2-methyl-4-thiazolyl).

Scheme 19

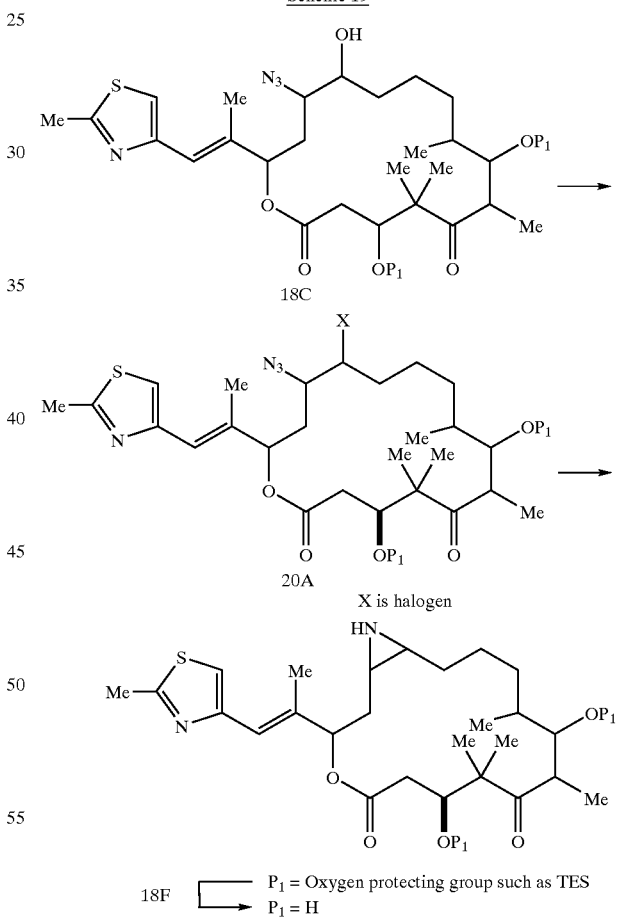

18F ⎡ P₁ = Oxygen protecting group such as TES
   ⎣ → P₁ = H

Alternatively, a compound of formula 18C where P1 is an oxygen protecting group, can be converted to a compound of formula 20A where X is a halogen by treatment with, for example, triphenylphosphine and a carbon tetrahalide. Reduction of the azido group and subsequent cyclization of a compound of formula 20A using a reducing agent such as a triaryl- or trialkylphosphine or with hydrogen and Lindlar's catalyst (Pd, CaCO3/Pb) provides a compound of formula L such as 18F (where $R_{1-4}$ are methyl and $R_6$ is 2-methyl-4-thiazolyl).

N-acyl derivatives of the present invention (such the compound of Example 23) were prepared by reacting compound 18F with the corresponding acid halide (alkyl or aryl carbonyl halide, or acyl halide) in the presence of a base, such as diisopropylethylamine. Acyl halides include, but are not limited to, acetyl chloride, benzoyl chloride and thiophene-2-carbonyl chloride.

N-sulfonyl derivatives (such as the compounds of Example 26) were prepared by reacting compound 18F with the corresponding sulfonyl halide in the presence of a base, such as diisopropylethylamine. Sulfonyl halides include, but are not limited to, propane sulfonyl chloride, 2-thienyl sulfonyl chloride and pyrazolyl sulfonyl chloride.

N-sulfonylureido derivatives (such as the compounds of Examples 17–19) were prepared by reacting compound 18F with the corresponding sulfamoyl halide in the presence of a base, such as diisopropylethylamine. Sulfamoyl halides include, but are not limited to, N-alkyl sulfamoyl halide, N-aryl sulfamoyl halide, N-cycloalkyl sulfamoyl halide and N-heterocyclyl sulfamoyl halide. Sulfamoyl halides include, but are not limited to, N-methylsulfamoyl chloride, N,N-dimethylsulfamoyl chloride, N-phenylsulfamoyl chloride, N-chlorosulfonyl morpholine and N-(2-thienyl)sulfamoyl chloride.

The in vitro assessment of biological activity of the compounds of formula I and formula II are presented in Table 1. Experiments were performed as follows:

In vitro Tubulin Polymerization

Twice cycled (2x) calf brain tubulin was prepared following the procedure of Williams and Lee (see Williams, R. C., Jr., and Lee, J. C. Preparation of tubulin from brain. Methods in Enzymology 85, Pt. D: 376–385, 1982) and stored in liquid nitrogen before use. Quantification of tubulin polymerization potency is accomplished following a modified procedure of Swindell, et al., (see Swindell, C. S., Krauss, N. E., Horwitz, S. B., and Ringel, L. Biologically active taxol analogues with deleted A-ring side chain substituents and variable C-2' configurations. *J. Med. Chem.* 34: 1176–1184, 1991). These modifications, in part, result in the expression of tubulin polymerization potency as an effective concentration for any given compound. For this method, different concentrations of compound in polymerization buffer (0.1M MES, 1 mM EGTA, 0.5 mM $MgCl_2$, pH 6.6) are added to tubulin in polymerization buffer at 37° in microcuvette wells of a Beckman (Beckman Instruments) Model DU 7400 UV spectrophotometer. A final microtubule protein concentration of 1.0 mg/ml and compound concentration of generally 2.5, 5.0, and 10 $\mu$M are used. Initial slopes of OD change measured every 10 seconds were calculated by the program accompanying the instrument after initial and final times of the linear region encompassing at least 3 time points were manually defined. Under these conditions linear variances were generally $<10^{-6}$, slopes ranged from 0.03 to 0.002 absorbance unit/minute, and maximum absorbance was 0.15 absorbance units. Effective concentration ($EC_{0.01}$) is defined as the interpolated concentration capable of inducing an initial slope of 0.01 OD/minute rate and is calculated using the formula: $EC_{0.01}$= concentration/slope. $EC_{0.01}$ values are expressed as the mean with standard deviation obtained from 3 different concentrations. $EC_{0.01}$ values for the compounds in this invention fall in the range 0.01–1000 $\mu$M.

Cytoxicity (In-Vitro)

Cytoxicity was assessed in HCT-116 human colon carcinoma cells by MTS (3-(4,5-dimethylthiazol-2-yl)-5-(3-carboxymethoxyphenyl)-2-(4-sulphenyl)-2H-tetrazolium, inner salt) assay as reported in T. L. Riss, et. al., "Comparison of MTT, XTT, and a novel tetrazolium compound MTS for in vitro proliferation and chemosensitivity assays.," *Mol. Biol. Cell* 3 (Suppl.): 184a, 1992. Cells were plated at 4,000 cell/well in 96 well microtiter plates and 24 hours later drugs were added and serial diluted. The cells were incubated at 37° form 72 hours at which time the tetrazolium dye, MTS at 333 $\mu$g/ml (final concentration), in combination with the electron coupling agent phenazine methosulfate at 25 $\mu$M (final concentration) was added. A dehydrogenase enzyme in live cells reduces the MTS to a form that absorbs light at 492 nM which can be quantitated spectrophotometrically. The greater the absorbance the greater the number of live cells. The results are expressed as an $IC_{50}$, which is the drug concentration required to inhibit cell proliferation (i.e. absorbance at 450 nM) to 50% of that of untreated control cells. The $IC_{50}$ values for compounds of this invention generally fall in the range 0.01–1000 nM.

As preferred compounds there are formula I and II compounds wherein

Q is selected from the group consisting of

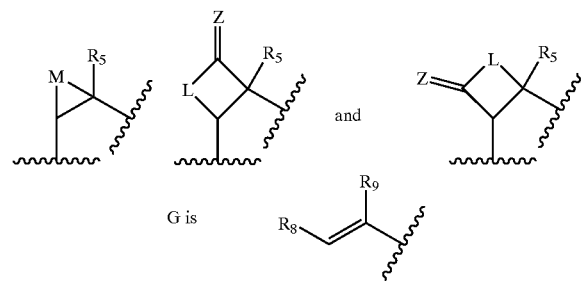

G is

X is O or S
and Y is O.

Most preferred are compounds of formulas I and II wherein:

Q is

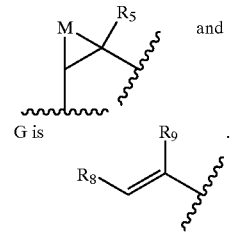

G is

The following examples illustrate the present invention.

EXAMPLE 1

[1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-4-oxa-17-azabicyclo[14.1.0]heptadecane-5,9-dione.

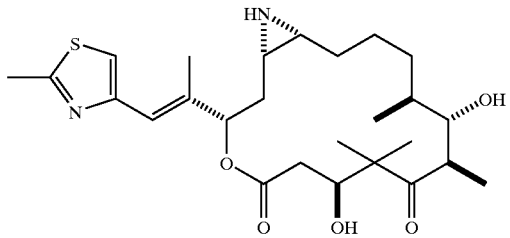

A. [1R-[1R*,3S*(E),7S*,10R*,11S*,12S*,16S*]]-7,11-Dihydroxy-8,8,10,12-tetramethyl-3-[1-methyl-2(2-methyl-4-thiazolyl)ethenyl]-4,17-dioxabicyclo[14.1.0]heptadecane-5,9-dione. [12,13-Epi Epothilone A]

To solution of epothilone C (100 mg, 0.21 mmol) in $CH_3CN$ (2.5 mL) and 0.0004 M $Na_2EDTA$ (1.5 ml) at 0° C. were added excess $CF_3COCH_3$ (1 mL) followed by 2 $KHSO_5 \cdot KHSO_4 \cdot K_2SO_4$ (potassium peroxymonosulfate) (325 mg, 0.53 mmol) and $NaHCO_3$ (75 mg, 0.89 mmol). The reaction mixture was stirred for 35 min then treated with dimethylsulfide (0.50 mL) and water (3.75 mL). The reaction mixture was warmed to room temperature, extracted with EtOAc (4×10 mL), dried over $MgSO_4$, filtered, and concentrated. The residue was chromatographed with 55% EtOAc/hexanes to give epothilone A (59 mg, 57%) and compound A (30 mg, 29%) as a white solid. m/z: 494(M+H)$^+$.

B. [4S-[4R*,7S*,8R*,9R*,13S*,14S*,16R*(E)]]-13-Azido-4,8,14-trihydroxy -5,5,7,9-tetramethyl-16-[1-methyl-2(2-methyl-4-thiazolyl)ethenyl]-1-oxacyclohexadecane-2,6-dione.

To a solution of Compound A (30 mg, 0.06 mmol) in EtOH (2.5 mL) were added $NaN_3$ (24 mg, 0.36 mmol) and $NH_4Cl$ (2 mg, 0.04 mmol). The reaction mixture was heated at 60° C. for 2 days. The reaction was concentrated, and the residue was chromatographed with 60% EtOAc/hexanes to give Compound B (19 mg, 59%) as a colorless oil. m/z:537 (M+H)$^+$.

C. [1S-[1R*,3R*(E),7R*,10S*,11R*,12R*,16S*]]-7,11-Dihydroxy-8,8,10,12-tetramethyl-3-[1-methyl-2(2-methyl-4-thiazolyl)ethenyl]-4-oxa-17-azabicyclo[14.1.0]heptadecane-5,9-dione.

To a solution of Compound B (19 mg, 0.035 mmol) in THF (1.5 mL) was added $PPh_3$ (12 mg, 0.047 mmol), and the reaction mixture was heated at 60° C. for 14 hr. The reaction was concentrated, and the residue was chromatographed with MeOH/EtOAc/Et$_3$N (1:9:0.3) to give the title compound (11 mg, 62%) as a white solid. m/z:493 (M+H)$^+$.

EXAMPLE 2

[1S-[1R*,3R*(E),7R*,10S*,11R*,12R*,16S*]]-17-Formyl-7,11-Dihydroxy-8,8,10,12-tetramethyl-3-[1-methyl-2-(2-methyl-4-thiazolyl)ethenyl]-4-oxa-17-azabicyclo[14.1.0]heptadecane-5,9-dione.

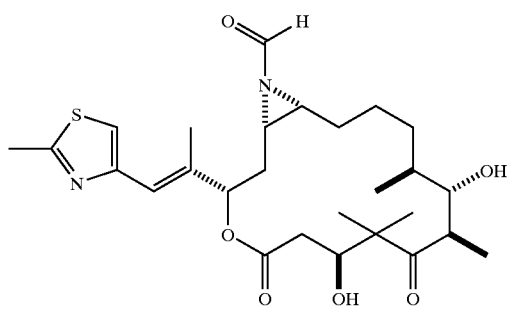

To solution of epothilone 1C (2 mg, 0.004 mmol) in acetone (0.2 mL) at 0° C. was added 4-formyl-2-methyl-1,3,4-thiadiazolin-5-thione (1 mg, 0.006 mmol), and the reaction mixture was stirred for 1 hr (See for example: Yazawa, H.: Goto, S. *Tetrahedron Lett.*, (1985) 26, 3703–3706). The reaction was concentrated, and the residue was chromatographed with 65% EtOAc/hexanes to give the title compound (0.8 mg, 38%) as a white film. m/z: 521 (M+H)$^+$.

EXAMPLE 3

[1S-[1R*,3R*(E),7R*,10S*,11R*,12R*,16S*]]-7,11-dihydroxy-8,8,10,12-tetramethyl-3-{1-methyl-2(2-methyl-4-thiazolyl)ethenyl]-4-oxa-17-thiabicyclo[14.1.0]heptadecane-5,9-dione.

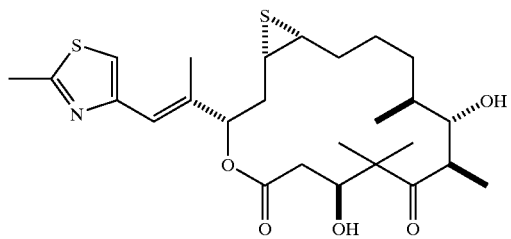

Compound 1A (50 mg, 0.1 mmol) and ammonium thiocycanate (25 mg, 0.33 mmol) were dissolved in acetonitrile (1.5 mL) and heated in a sealed vial to 120° C. for 30 min. The reaction mixture was separated by HPLC (C18, 45% acetonitrile/55% 50 mM ammonium acetate buffer, pH 6.8, with UV detection at 254 nM) to give the title compound (11 mg, 21%). m/z: 553 (M+H)$^+$.

EXAMPLE 4

[1S-[1R*,3R*(E),7R*,10S*,11R*,12R*,16S*]]-17-[Dimethylamino)acetyl]-7,11-dihydroxy-8,8,10,12-tetramethyl-3-[1-methyl-2(2-methyl-4-thiazolyl)ethenyl]-4-oxa-17-azabicyclo[14.1.0]heptadecane-5,9-dione.

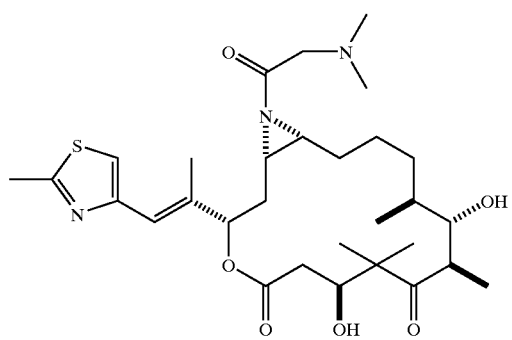

To a solution of compound 1C (10 mg, 0.020 mmol) and N,N-dimethylglycine (2.3 mg, 0.022 mmol) in methylene chloride (0.20 mL) was added a catalytic amount of DMAP followed by the addition of DCC (8.3 mg, 0.040 mmol) at 0° C. The reaction mixture was warmed to room temperature and stirred for 18 h under Ar. The mixture was directly purified by flash chromatography (short $SiO_2$ plug, 0–2% methanol/chloroform gradient elution), and then further purified by reverse phase HPLC (YMC S-5 ODS 10×250 mm column, A-95% water, 5% MeCN, B=95% MeCN, 5% water, 0–100% B/40 minutes/gradient, flow rate=3 mL/min, retention time=29 min) to afford 3 mg of the title compound (26%) as white a lyophilizate along with 4 mg of starting material (40%). FABHRMS m/z 578.3287 ($C_{30}H_{47}N_3O_6S$, requires 577.3186).

EXAMPLE 5

[1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-17-(3-methyl-1-oxobutyl)-4-oxa-17-azabicyclo[14.1.0]heptadecane-5,9-dione.

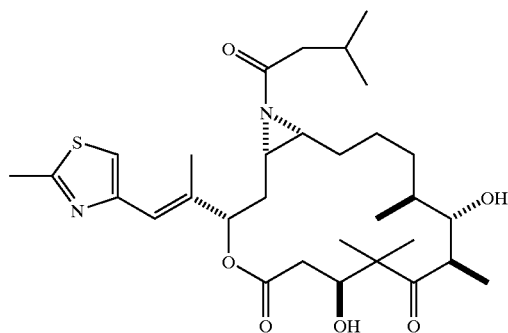

To a solution of compound 1C (10 mg, 0.020 mmol) and triethylamine (10 μL, 0.080 mmol) in methylene chloride (0.20 mL) was added isovaleryl chloride (13.0 μL, 0.024 mmol) at 0° C. The reaction mixture was warmed to room temperature and stirred for 1 h under argon. The mixture was diluted with methylene chloride (5 mL) and was quenched with saturated aqueous sodium bicarbonate (1 mL) at 0° C.

The organic layer was collected, dried over sodium sulfate, and concentrated. The oily residue was purified by flash chromatography ($SiO_2$, 4.5×30 cm, 25–50% EtOAc-hexanes gradient elution) to afford the title compound (6 mg, 51%) as a white solid. FABHRMS m/z 577.3343 ($C_{31}H_{48}N_2O_6S$, requires 576.3233). $^1H$ NMR (400 MHz, $CDCl_3$) δ 6.97 (s, 1 H), 6.57 (s, 1 H), 5.38–5.35 (m, 1 H), 4.15–4.11 (m, 1 H) 3.84–3.80 (m, 2 H), 3.18–3.15 (m, 1 H), 2.70 (s, 3 H), 2.66–2.53 (m, 2 H), 2.52–2.49 (m, 2 H), 2.45–2.11 (m, 6 H), 2.09 (s, 3 H), 1.84–1.72 (m, 3 H), 1.55–1.40 (m, 4 H) 1.36 (s, 3 H), 1.19 (s, 3 H, J=6.8 Hz), 1.14 (s, 3 H), 1.02 (d, 3 H, J=6.9 Hz), 0.95–0.93 (m, 6 H). MS ($ESI^+$): 577.3 $(M+H)^+$.

EXAMPLE 6

[1S-[1R*,3R*(E), 7R*,10S,11R*,12R*,16S*]]-17-N-Methylsulfonyl-7,11-dihydroxy-8,8,10,12-tetramethyl-3-[1-methyl-2-(2-methyl-4-thiazolyl)ethenyl]-4-oxa-17-azabicyclo[14.1.0]heptadecane-5,9-dione.

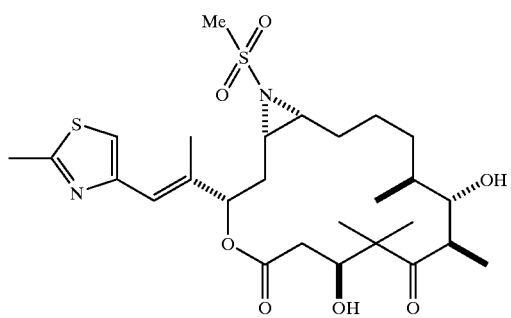

To a solution of compound 1C (10 mg, 0.020 mmol) and pyridine (8 μl, 0.10 mmol) in methylene chloride (0.20 ml) under Ar was added methanesulfonyl chloride (1.6 μl, 0.021 mmol) at −15° C. The reaction mixture was kept at −15° C. and stirred for 30 minutes. The mixture was diluted with methylene chloride (5 mL) and was quenched with saturated aqueous sodium bicarbonate (1 mL) at 0° C. The organic layer was collected, dried over sodium sulfate, and concentrated. The oily residue was purified by flash chromatography ($SiO_2$, 4.5×30 cm, 25–50% EtOAc-hexanes gradient elution) to afford the title compound (6 mg, 52%) as a white solid. $^1H$ NMR (400 MHz, $CDCl_3$) δ 6.98 (s, 1 H), 6.57 (s, 1 H), 5.34 (d, 1 H, J=8.0 Hz), 4.15–4.12 (m, 1 H), 3.84–3.81 (m, 1 H), 3.78–3.75 (m, 1 H), 3.18–3.10 (m, 1 H), 3.04 (s, 3 H), 2.87–2.83 (m, 1 H), 2.75–2.71 (m, 1 H), 2.70 (s, 3 H), 2.62–2.55 (m, 1 H), 2.52 (dd, 1 H, J=14.7, 10.2 Hz), 2.43 (dd, 1 H, J=14.7, 3.0 Hz), 2.32–2.27 (m, 1 H), 2.05 (s, 3 H), 1.93–1.70 (m, 3 H), 1.58–1.42 (m, 5 H), 1.36 (s, 3 H), 1.18 (d, 3 H, J=6.8 1.15 (s, 3 H), 1.01 (d, 3 H, J=6.9 Hz). FAB HRMS m/z ($M^+$+H) calcd for $C_{27}H_{42}N_2O_7S_2$: 571.2512, found: 571.2525.

EXAMPLE 7

1S-[1R*,3R*(E),7R*,10S,11R*,12R*,16S*]]-N-Ethyl-7,11-dihydroxy-8,8,10,12-tetramethyl-3-[1-methyl-2-(2-methyl-4-thiazolyl)ethenyl]-4-oxa-17-azabicyclo[14.1.0]heptadecane-5,9-dione-17-carboxamide.

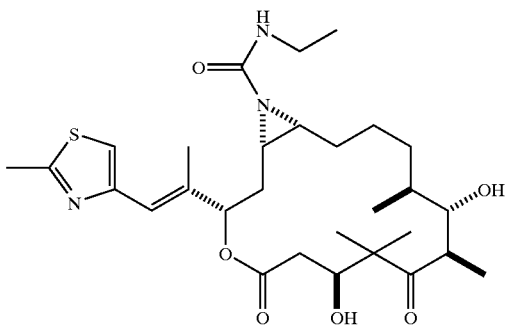

To a solution of compound 1C (10 mg, 0.020 mmol) in EtOAc (0.20 mL) was added ethyl isocyanate (1.9 μL, 0.024 mmol) at 0° C. under Ar. The reaction mixture was warmed to room temperature and stirred for 30 minutes. The mixture was directly purified by flash chromatography (SiO$_2$, 4.5×30 cm, 0–3% methanol-chloroform gradient elution) to provide the title compound (5.5 mg, 66%) as white solid. FAB-HRMS m/z 564.3367 (C$_{29}$H$_{45}$N$_3$O$_6$S, requires 563.3029). $^1$H NMR (400 MHz, CDCl$_3$) δ 6.97 (s, 1 H), 6.60 (s, 1 H), 5.62–5.59 (m, 2 H), 4.51 (br s, 1 H, OH), 4.23–4.18 (m, 1 H), 3.86–3.83 (m, 1 H), 3.23–3.20 (m, 3 H), 2.70 (s, 3 H), 2.53–2.42 (m, 2 H), 2.40–2.36 (m, 2 H), 2.09 (s, 3 H), 1.98–1.92 (m, 2 H), 1.82–1.77 (m, 1 H), 1.61–1.36 (m, 7 H), 1.35 (s, 3 H), 1.15 (d, 3 H, J=7.0 Hz), 1.11 (t, 3 H, J=7.4 Hz), 1.08 (s, 3 H), 0.97 (d, 3 H, J=6.9 Hz); HRMS (ESI$^+$) m/z (M$^+$+H) calcd for C$_{29}$H$_{45}$N$_3$O$_6$S: 564.3107, found: 564.3367.

EXAMPLE 8

[1S-[1R*,3R*(E),7R*,10S*,11R*,12R*,16S*]]-7,11-Dihydroxy-8,8,10,12,17-pentamethyl-3-[1-methyl-2-(2-methyl-4-thiazolyl)ethenyl]-4-oxa-17-azabicyclo[14.1.0]heptadecane-5,9-dione

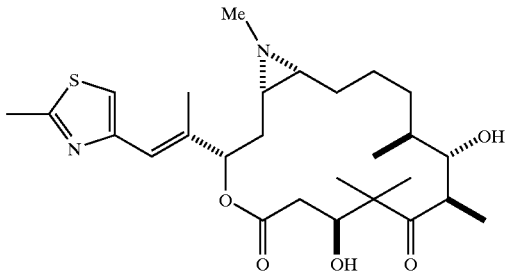

To a solution of compound 1C (10 mg, 0.020 mmol) in THF (0.20 mL) under argon was added proton sponge (0.05 M solution in THF, 4.2 μL, 0.021 mmol) followed by dimethylsulfate (2.8 μL, 0.030 mmol) at −10° C. The reaction mixture was then stirred overnight at 4° C. The mixture was directly purified by flash chromatography (SiO$_2$, 4.5×30 cm, 0–3% methanol-chloroform gradient elution) to afford the title compound (5.0 mg, 40%) as white solid. FAB-HRMS m/z 507.2888 (C$_{27}$H$_{42}$N$_2$O$_5$S, requires 506.2814).

EXAMPLE 9

[1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-5,9-dioxo-4-oxa-17-azabicyclo[14.1.0]heptadecane-17-carboxylic acid, 1,1-dimethylethyl ester.

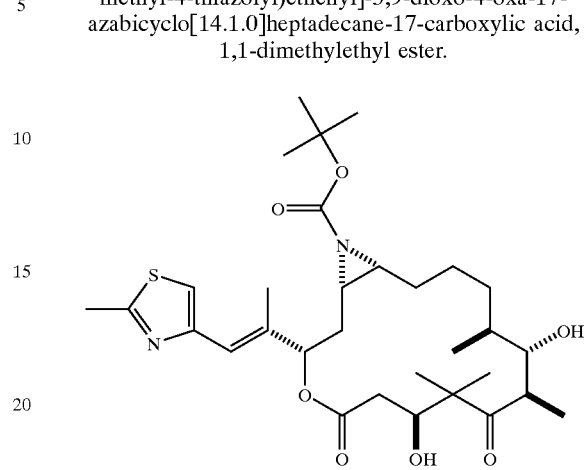

Di-tert-butyl dicarbonate (0.008 mmol, 1.8 mg) was added to Compound 1C (0.004 mmol, 2 mg) and triethylamine (0.0048 mmol, 0.0007 ml) in THF (0.15 mL) at room temperature. After 30 min, the reaction was concentrated and purified by flash chromatography (50% EtOAc/Hexanes) to afford the title compound as a clear oil (1.8 mg). (M+H)$^+$ 593.

EXAMPLE 10

[1S-[1R*,3R*(E),10S*,11R*,12R*,16S*]]-11-Hydroxy-8,8,10,12-tetramethyl-3-[1-methyl-2-(2-methyl-4-thiazolyl)ethenyl]-4,18-dioxabicyclo[14.2.0]octadec-6(E)-ene-5,9-dione

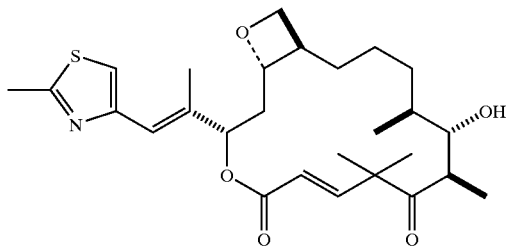

A. [1S-[1R*,3R*(E),10S*,11R*,12R*,16S*]]-11-Hydroxy-8,8,10,12-tetramethyl-3-[1-methyl-2-(2-methyl-4-thiazolyl)ethenyl]-4,17-dioxabicyclo[14.1.0]heptadec-6(E)-ene-5,9-dione.

HCO$_2$H (22.7 mmol, 0.85 mL) was added to a solution of epothilone B (4.5 mmol, 2.3 g), NEt$_3$ (45.3 mmol, 6.3 mL) and N,N-dimethylaminopyridine (10 mmol, 1.2 g) in CH$_2$Cl$_2$ (100 mL) at room temperature. The reaction mixture was cooled to −15° C., and (CH$_3$CO)$_2$O (22.7 mmol, 2.1 mL) was added dropwise. The reaction was maintained at −15° C. for 15 minutes then at room temperature for 30 minutes. The reaction was quenched with pH 7 buffer (100 mL) and extracted with CH$_2$Cl$_2$ (3×100 mL). The combined organic phase was washed with 1N HCl (100 mL), saturated NaHCO$_3$ (100 mL), dried over Na$_2$SO$_4$, and concentrated to give the bis-formate of epothilone B as a white solid, which was taken to next step without further purification. 1,8-Diazabicyclo[5.4.0]undec-7-ene (44.7 mmol, 6.7 mL) was added dropwise to the crude bis-formate in CH$_2$Cl$_2$ (125 mL) at room temperature. The reaction mixture was stirred for 1 hour, quenched with pH 4 buffer (200 mL) and extracted with CH$_2$Cl$_2$ (3×200 mL). The combined organic phase was washed with saturated NaHCO$_3$ (200 mL), dried over Na$_2$SO$_4$ and concentrated to give a viscous oil which was taken up in MeOH (95 mL) and treated with NH$_3$ (2M solution in MeOH, 21.9 mmol, 11 mL). The reaction mixture was maintained at room temperature for 4 hours, concentrated and purified by flash chromatography (60% EtOAc/ Hexanes to neat EtOAc) to afford compound A as a white solid (2.05 g, 92% for 3 steps). (M+H)+ 490.

B. [1S-[1R*,3R*(E),10S*,11R*,12R*,16S*]]-11-Triethylsilyloxy-8,8,10,12-tetramethyl-3-[1-methyl-2-(2-methyl-4-thiazolyl)ethenyl]-4,17-dioxabicyclo[14.1.0] heptadec-6(E)-ene-5,9-dione.

Et$_3$SiCl (10.8 mmol, 1.8 mL) was added to compound A (1.08 mmol, 529 mg), N,N-diisopropylethylamine (16.2 mmol, 2.8 mL), and N,N-dimethylaminopyridine (1.08 mmol, 132 mg) in CH$_2$Cl$_2$ (10 mL) at room temperature. The reaction mixture was then heated at 45° C. for 12 hours, quenched with pH 4 buffer (50 ml), extracted with CH$_2$Cl$_2$ (3×25 mL), dried over Na$_2$SO$_4$, concentrated and purified by flash chromatography (hexanes to 20% EtOAc/hexanes) to afford compound B as a white solid (590 mg). (M+H)$^+$ 604.

C. [7R,8S,9S,14S,16S(E)]-14-Hydroxy-13-hydroxymethyl-8-triethylsilyloxy-5,5,7,9-tetramethyl-16-[1-methyl-2-(2-methyl-4-thiazolyl)ethenyl]-1-oxa-3(E)-cyclohexadecene-2,6-dione.

Diethylaluminum-2,2,6,6-tetramethylpiperidide-[1.5 mL of 0.28M solution in benzene maintained at 0° C., 0.42 mmol; prepared by method of Paquette, L. A. et. al. *J. Org. Chem* 1990, 55, 1589; stepwise addition of n-BuLi (1.1 mmol, or 0.68 mL of 1.6 M solution in hexanes) and diethylaluminumchloride (1.1 mmol, 1.1 mL of 1.0 M solution in hexanes) to 2,2,6,6-tetramethylpiperidine (1.1 mmol, 0.15 mL) in benzene (2.0 ml) at 0° C.] was added dropwise over 20 min to Compound B (0.18 mmol, 109 mg) in benzene (2.0 mL) at 0° C. The reaction mixture was quenched with saturated NH$_4$Cl (8 mL), extracted with CH$_2$Cl$_2$ (3×10 mL), dried over Na$_2$SO$_4$, concentrated and purified by flash chromatography (25% EtOAc/hexanes) to afford 13,14-allylic alcohol as a clear oil (70 mg, 64%). (M+H)$^+$ 604.

BH$_3$.THF (0.35 mmol, 0.35 ml of 1.0 M solution in THF) was added dropwise to the 13,14-allylic alcohol intermediate in THF (4.0 mL) at −78° C. The reaction mixture was stirred at −78° C. for 10 minutes, then transferred to a 0° C. bath. After 4.6 hours, the reaction mixture was stirred at room temperature for 10 minutes, diluted with THF/EtOH (4.0 mL), quenched by stepwise addition of pH 7 phosphate buffer (4.0 mL) and 30% H$_2$O$_2$ aqueous solution (4.0 mL). The resulting reaction mixture was stirred at room temperature for 17 hours, extracted with CH$_2$Cl$_2$ (3×10 mL), dried over Na$_2$SO$_4$, concentrated and purified by flash chromatography (60–75% EtOAc/hexanes) to afford compound C as a clear oil (51.2 mg, 2:1 mixture of 13R/13S diastereomers). (M+H)$^+$ 622.

D. [7R,8S,9S,13R,14S,16S(E)]-14-Hydroxy-13-p-toluenesulfonyloxymethyl-8-triethylsilyloxy-5,5,7,9-tetramethyl-16-[1-methyl-2-(2-methyl-4-thiazolyl)ethenyl]-1-oxa-3(E)-cyclohexadecene-2,6-dione.

p-Toluenesulfonylchloride (0.1 mmol, 19 mg) was added to compound C (31 mg, 2:1 (trans:cis), 0.05 mmol) and pyridine (0.25 mmol, 0.02 mL) in CH$_2$Cl$_2$ (1.0 mL) at room temperature. The reaction mixture was heated at 35° C. for 16 hours, then additional p-toluenesulfonylchloride (0.1 mmol, 19 mg) and pyridine (0.25 mmol, 0.02 mL) were added. After 4 hours, the reaction was quenched with pH 4 buffer (20 mL), extracted with CH$_2$Cl$_2$ (3×10 mL), dried over Na$_2$SO$_4$, concentrated and purified by flash chromatography (30% to 60% EtOAc/hexanes) to afford tosylate, as a clear oil (22.3 mg, 13R/13S=2) and unreacted starting material (3.8 mg). The 13S and 13R (Compound D) isomers were separated by flash chromatography (neat Et$_2$O). (M+H)$^+$ 776 for both isomers.

E. [1S-[1R*,3R*(E),10S*,11R*,12R*,16S*]]-11-Triethylsilyloxy-8,8,10,12-tetramethyl-3-[1-methyl-2-(2-methyl-4-thiazolyl)ethenyl]-4,18-dioxabicyclo[14.2.0] octadec-6(E)-ene-5,9-dione.

NaH (60% in nujol, a pinch, >0.053 mmol) was added to Compound D (41 mg, 0.053 mmol) in DMF (1.0 mL) at room temperature. After 20 minutes, the reaction was quenched with saturated NH$_4$Cl (10 mL), extracted with CH$_2$Cl$_2$ (3×50 mL), dried over Na$_2$SO$_4$, concentrated and purified by flash chromatography (10% to 30% EtOAc/ hexanes) to afford Compound E, as a clear oil (11.3 mg). (M+H)$^+$ 604.

F. [1S-[1R*,3R*(E),10S*,11R*,12R*,16S*]]-11-Hydroxy-8,8,10,12-tetramethyl-3-[1-methyl-2-(2-methyl-4-thiazolyl) ethenyl]-4,18-dioxabicyclo[14.2.0]octadec-6(E)-ene-5,9-dione.

Trifluoroacetic acid (1 mL of 20% solution in CH$_2$Cl$_2$) was added to Compound E (0.011 mmol, 6.5 mg) in CH$_2$Cl$_2$ (1 mL) at −20° C. After 20 minutes, the reaction mixture was quenched with saturated NaHCO$_3$ (1 mL), extracted with CH$_2$Cl$_2$ (3×10 mL), dried over Na$_2$SO$_4$, concentrated and purified by flash chromatography (20% to 60% EtOAc/ hexanes with 1% triethylamine) to afford the title compound, as a white solid (4.3 mg). (M+H)$^+$ 490.

EXAMPLE 11

[5S-[5R*(E),9R*,12S*,13R*,14R*]]-4,9,10,13,14, 15,16,17-Octahydro-9,13-dihydroxy-2,10,10,12,14-pentamethyl-5-[1-methyl-2-(2-methyl-4-4-thiazolyl) ethenyl]-5H-oxacyclohexadecino[5,4-d]thiazole-7,11 (8H, 12H)-dione.

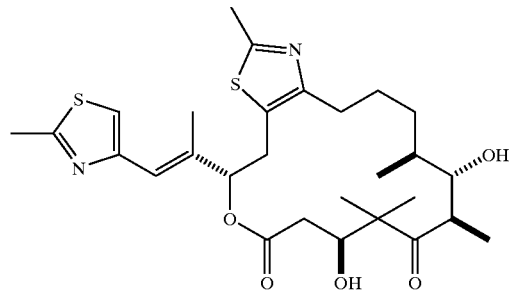

A. [1S-[1R*,3R*(E),7R*,10S*,11R*,12R*,16S*]]-7,11-Bistriethylsilyloxy-8,8,10,12-tetramethyl-3-[1-methyl-2-(2-methyl-4-thiazolyl)ethenyl]-4,17-dioxabicyclo[14.1.0] heptadecane-5,9-dione.

Et$_3$SiCl (4.15 mmol, 0.7 mL) was added to epothilone A (4.2 mmol, 205 mg), N,N-diisopropylethylamine (6.2 mmol, 1.1 mL), and imidazole (2.1 mmol, 141 mg) in DMF (5 mL) at room temperature. The reaction mixture was then heated at 40° C. for 15.5 hours. Additional N,N-diisopropylethylamine (4.2 mmol, 0.720 mL) and Et$_3$SiCl (2.1 mmol, 0.35 mL) were added and the reaction was heated to 60° C. After 48 hours, the reaction mixture was concentrated and purified by flash chromatography (5 to 10% EtOAc/hexanes) to afford Compound A as a clear oil (264 mg). (M+H)+ 722.

B. [4S-[4R*,7S*,8R*,9R*,13S*,14S*,16R*(E)]]-14-Bromo-13-hydroxy-4,8-bistriethylsilyloxy-5,5,7,9-tetramethyl-16-[1-methyl-2-(2-methyl-4-thiazolyl)ethenyl]-1-oxacyclohexadecane-2,6-dione.

MgBr$_2$.OEt$_2$ (9.7 mmol, 2.5 g) was added to Compound A (6.45 mmol, 4.66 g) in CH$_2$Cl$_2$ (80 mL) at −78° C. After 2 hours, the reaction mixture was warmed to 50° C. and additional MgBr$_2$.OEt$_2$ (9.7 mmol, 2.5 g) was added. The reaction mixture was again warmed to −30° C. and maintained for 1 hour; and then warmed to −20° C., where additional MgBr$_2$.OEt$_2$ (6.45 mmol, 1.7 g) was added. After 1 hour, the reaction mixture was quenched with pH 7 phosphate buffer (20 mL), extracted with CH$_2$Cl$_2$ (3×100 mL), ), dried over Na$_2$SO$_4$, concentrated and purified by flash chromatography (30% EtOAc/hexanes) to afford Compound B as a white solid (2.95 g). (M+H)+ 802.

C. [4S-[4R*,7S*,8R*,9R*,13S*,14S*,16R*(E)]]-14-Bromo-4,8-bistriethylsilyloxy-5,5,7,9-tetramethyl-16-[1-methyl-2-(2-methyl-4-thiazolyl)ethenyl]-1-oxacyclohexadecane-2,6,13-trione.

Pyridinium chlorochromate (1.48 mmol, 320 mg) was added to Compound B (0.37 mmol, 300 mg), pyridine (3.7 mmol, 0.3 mL) and small amount of crushed 4A molecular sieves in CH$_2$Cl$_2$ (3 μL). After 5 hours, the reaction mixture was diluted with CH$_2$Cl$_2$ (50 mL), filtered through a short pad of silica gel, concentrated and purified by flash chromatography (5% EtOAc/Hexanes) to afford Compound C as a white solid (273 mg). (M+H)+ 800.

D. [5S-[5R*(E),9R*,12S*,13R*,14R*]]-4,9,10,13,14,15,16,17-Octahydro-9,13-bistriethylsilyloxy-2,10,10,12,14-pentamethyl-5-[1-methyl-2-(2-methyl-4-thiazolyl)ethenyl]-5H-oxacyclohexadecino[5,4-d]thiazole-7,11(8H,12H)-dione.

Thioacetamide (0.03 mmol, 2.3 mg) was added to Compound C (0.015 mmol, 12 mg) and N,N-diisopropylethylamine (0.038 mmol, 0.006 mL) in ethanol (0.3 mL). The reaction mixture was heated at 80° C. for 24 hours. The reaction mixture was concentrated and purified by flash chromatography (50% to 75% EtOAc/Hexanes) to afford a hydroxythiazoline intermediate (4.6 mg, 39%). (M+H)+ 795.

Methanesulfonyl chloride (0.01 mmol, 0.0008 mL) and triethylamine (0.04 mmol, 0.006 mL) were added stepwise to the hydroxythiazoline intermediate (0.005 mmol, 4.2 mg) in CH$_2$Cl$_2$ (0.175 mL) at 0° C. The reaction flask was then removed from the ice bath and stirred at room temperature for 5 hours, concentrated and purified by flash chromatography (18% EtOAc/Hexanes) to afford Compound D (1.2 mg). (M+H)+ 777.

E. [5S-[5R*(E),9R*,12S*,13R*,14R*]]-4,9,10,13,14,15,16,17-Octahydro-9,13-dihydroxy-2,10,10,12,14-pentamethyl-5-[1-methyl-2-(2-methyl-4-thiazolyl)ethenyl]-5H-oxacyclohexadecino[5,4-d]thiazole-7,11(8H,12 H)-dione.

Trifluoroacetic acid (0.150 mL of 40% solution in CH$_2$Cl$_2$) was added to Compound D (0.0036 mmol, 2.8 mg) in CH$_2$Cl$_2$ (0.150 mL) at 0° C. After 20 minutes, the reaction mixture was concentrated and purified by flash chromatography (80% EtOAc/Hexanes) to afford the title compound (1.8 mg). (M+H)+ 549.

EXAMPLE 12

[1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-4-oxa-17-azabicyclo[14.1.0]heptadecane-5,9-dione.

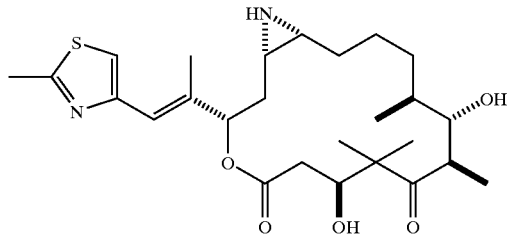

A. [1S-[1R*,3R*(E),7R*,10S*,11S*,12R*,16S*]]-7,11-Bistriethylsilyloxy-8,8,10,12-tetramethyl-3-[1-methyl-2-(2-methyl-4-thiazolyl)ethenyl]-4,17-dioxabicyclo[14.1.0]heptadecane-5,9-dione.

Et$_3$SiCl (25 ml, 149 mmol) was added to epothilone A (10.39 g, 21 mmol), N,N-diisopropylethylamine (55 ml, 315 mmol), and imidazole (7.15 g, 105 mmol,) in DMF (75 mL) at 25° C. The reaction mixture was then heated at 55° C. for 6.5 h and concentrated in vacuo. The residue was then diluted with CH$_2$Cl$_2$ (100 mL) and the organic extracts were washed with NaCHO$_3$ (30 mL), dried over Na$_2$SO$_4$ and concentrated in vacuo. The residue was purified by flash chromatography (SiO$_2$, 5.0×30 cm, hexanes to 15% EtOAc/hexanes gradient elution) to afford Compound A as a white solid [15.1 g, >95%]. MS (ESI+):(M+H)+ 722.

B. [4S-[4R*,7S*,8R*,9R*,13S*,14S*,16R*(E)]-14-Bromo-13-hydroxy-4,8-bistriethylsilyloxy-5,5,7,9-tetramethyl-16-[1-methyl-2-(2-methyl-4-thiazolyl)ethenyl]-1-oxacyclohexadecane-2,6-dione.

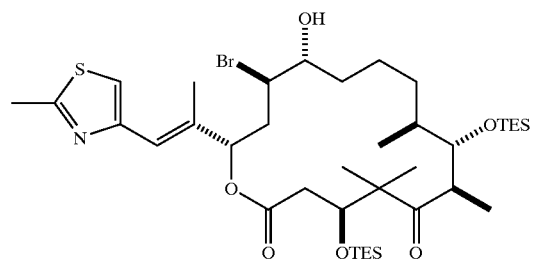

To a solution of bis-TES-epothilone A (2.0 g, 2.8 mmol) in CH$_2$Cl$_2$ (30 mL) at −20° C. under Ar was added MgBr$_2$.OEt$_2$ (3×1.1 g, 12 mmol total) in three portions every two hours while maintaining an internal temperature between −15 and −5° C. After 7 h, the reaction mixture was quenched with pH 7 aqueous phosphate buffer (40 mL) and brine (40 mL), carefully extracted with EtOAc (3×100 mL), dried (Na$_2$SO$_4$), and concentrated in vacuo. The residue was purified by flash chromatography (SiO$_2$, 4.5×25 cm, 10–20% EtOAc/hexanes gradient elution) to afford compound B as a white solid [1.0 g, 45% (67% based on 0.6 g of recovered starting material; <2% of the 13-bromo-14-hydroxy regioisomer was detected]. $^1$H NMR (400 MHz, CDCl$_3$) δ 6.97 (s, 1 H), 6.55 (s, 1 H), 5.48–5.46 (m, 1 H), 4.39–4.38 (m, 1 H), 3.69–3.66 (m, 1 H), 3.01–2.99 (m, 1 H), 2.76–2.74 (m, 1 H), 2.73 (s, 3 H), 2.71–2.56 (m, 3 H), 249–2.47 (m, 1 H), 2.13 (s, 3 H), 1.63–1.61 (m, 4 H), 1.30–1.28 (m, 2 H), 1.23 (s, 3 H), 1.14 (s, 3 H), 0.99–0.93 (m, 26 H), 0.72–0.63 (m, 12 H). MS (ESI+): (M+H)+ 802.

C. [4S-[4R*,7S*,8R*,9R*,13S*,14R*,16R*(E)]]-14-Azido-4,8-bistriethylsilyloxy-13-hydroxy-5,5,7,9-tetramethyl-16-[1-methyl-2-(2-methyl-4-thiazolyl)ethenyl]-1-oxacyclohexadecane-2,6-dione.

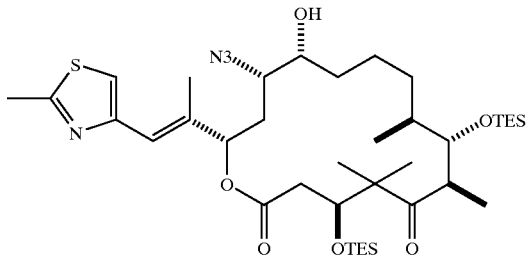

To a solution of compound B (0.17 g, 0.21 mmol) in DMF (2 mL) under Ar was added sodium azide (0.14 g, 2.1 mmol) and the resulting suspension was warmed to 43° C. After 36 h, the solvent was removed in vacuo and the residue was directly purified by flash chromatography (SiO$_2$, 2.5×15 cm, 10–20% EtOAc/hexanes gradient elution) to give compound C (0.14 g, 88%) as a white foam. $^1$H NMR (400 MHz, CDCl$_3$) δ 6.91 (s, 1 H), 6.51 (s, 1 H), 5.26–5.23 (m, 1 H), 3.99–3.92 (m, 1 H), 3.90–3.86 (m, 1 H), 3.81–3.72 (m, 1 H), 3.41–3.37 (m, 1 H), 2.92–2.89 (m, 1 H), 2.82–2.74 (m, 1 H), 2.64 (s, 3 H), 2.57–2.52 (m, 1 H), 2.21–2.18 (m, 1 H), 2.03 (s, 3 H), 1.81–1.42 (m, 5H), 1.37–0.96 (m, 10 H), 0.92–0.75 (m, 24 H), 0.67–0.51 (m, 12 H). MS (ESI$^+$): (M+H)$^+$ 765.

D. [4S-[4R*,7S*,8R*,9R*,13R*,14R*,16R*(E)]-14-Azido-4,8-bistriethylsilyloxy-13-(4-nitrobenzoyloxy)-5,5,7,9-tetramethyl-16-[1-methyl-2-(2-methyl-4-thiazolyl)ethenyl]-1-oxacyclohexadecane-2,6-dione.

To a solution of compound C (0.10 g, 0.13 mmol) in THF under Ar was sequentially added 4-nitrobenzoic acid (55 mg, 0.33 mmol), triphenylphosphine (86 mg, 0.33 mmol), and diethyl azodicarboxylate (52 μL, 0.33 mmol). The reaction mixture was stirred at 25° C. for 1.5 h, concentrated in vacuo and the residue was purified by flash chromatography (SiO$_2$, 2.5×10 cm, 10–20% EtOAc/hexanes gradient elution) to afford the corresponding p-nitrobenzoate (0.10 g, 86%) as a white foam. MS (ESI$^+$): 914.6 (M+H)$^+$.

E. [4S-[4R*,7S*,8R*,9R*,13R*,14R*,16R*(E)]-14-Azido-4,8-bistriethylsilyloxy-13-hydroxy-5,5,7,9-tetramethyl-16-[1-methyl-2-(2-methyl-4-thiazolyl)ethenyl]-1-oxacyclohexadecane-2,6-dione.

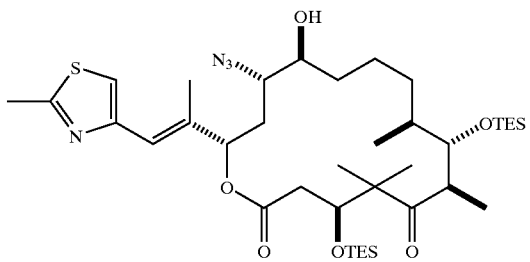

Compound D (0.10 g, 0.11 mmol) was then treated with 2.0 M ammonia in methanol (1 mL) at 25° C. under Ar for 4 h. The solvent was removed in vacuo and the residue was directly purified by flash chromatography (SiO$_2$, 1.5×10 cm, 10–30% EtOAc/hexanes gradient elution) to afford compound E (71 mg, 85%) as a white foam. $^1$H NMR (400 MHz, CDCl$_3$) δ 6.97 (s, 1 H), 6.59 (s, 1 H), 5.55–5.52 (m, 1H), 4.42–4.39 (m, 1H), 3.96–3.94 (m, 1 H), 3.61–3.56 (m, 1 H), 3.05–3.01 (m, 1 H), 2.75–2.74 (m, 1 H), 2.70 (s, 3 H), 2.61–2.56 (m, 1 H), 2.13 (s, 3 H), 2.04–2.02 (m, 1 H), 1.84–1.50 (m, 3 H), 1.18 (s, 3 H), 1.14–1.10 (m, 6 H), 1.07–0.93 (m, 24 H), 0.68–0.57 (m, 12 H). MS (ESI$^+$): 765.5 (M+H)$^+$; MS (ESI$^-$): 763.3 (M–H)$^-$.

F. [4S-[4R*,7S*,8R*,9R*,13R*,14R*,16R*(E)]]-14-Azido-4,8-13-trihydroxy -5,5,7,9-tetramethyl-16-[1-methyl-2-(2-methyl-4-thiazolyl)ethenyl]-1-oxacyclohexadecane-2,6-dione.

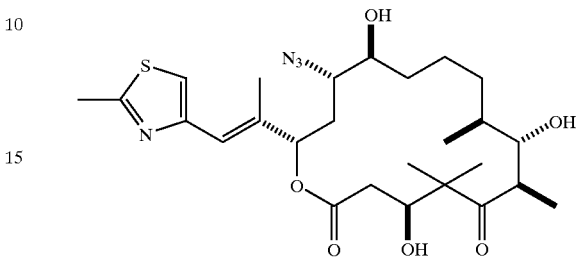

Compound E (15 mg, 0.20 mmol) was treated with 20% trifluoroacetic acid in methylene chloride (0.2 mL) at 0° C. under Ar for 10 min. The reaction mixture was concentrated under a constant stream of nitrogen at 0° C. and the residue was directly purified by flash chromatography (SiO$_2$, 1×5 cm, 0–5% MeOH/CHCl$_3$ gradient elution) to afford Compound F (9 mg, 86%) as a film. MS (ESI)$^+$: 537.3 (M–H)$^-$.

G. [1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-4-oxa-17-azabicyclo[14.1.0]heptadecane-5,9-dione.

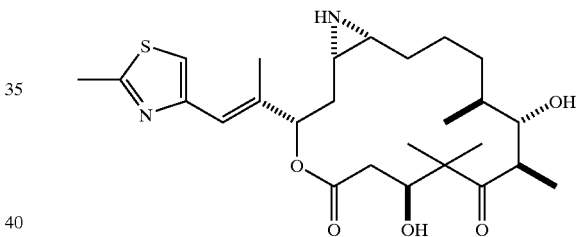

To a solution of Compound F (9 mg, 17 μmol) THF (0.2 mL) under Ar was added triphenylphosphine (18 mg. 67 μmol). The reaction mixture was warmed to 45° C. for 4 h, and the solvent was removed under a constant flow of nitrogen. The residue was purified by radial chromatography (1 mm SiO$_2$, GF rotor, 2–10% MeOH/CHCl$_3$ gradient elution) to afford the title compound (4 mg, 50%) as a film.
(Alternative Procedure)

H. [1S-[1R*,3R*(E),7R*,10S*,11R*,12R*,16S*]]-7,11-Bistriethylsilyloxy-8,8,10,12-tetramethyl-3-[1-methyl-2-(2-methyl-4-thiazolyl)ethenyl]-4-oxa-17-azabicyclo[14.1.0]heptadecane-5,9-dione.

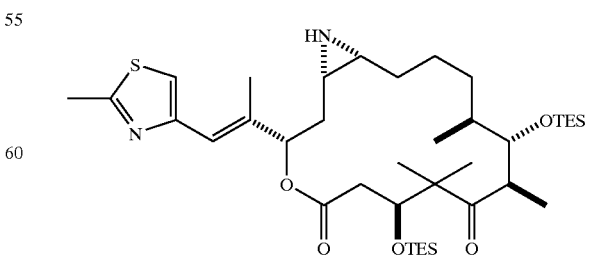

To a solution of compound E (56.5 mg, 67 μmol) in THF-H$_2$O (12:1, 1.2 mL) under Ar was added trimethylphosphine (134 μL, 1.0 M in THF). The reaction mixture was warmed to 45° C. for 10 h, and the solvent was removed under a constant flow of nitrogen. The residue was purified by flash chromatography (SiO$_2$, 1×5 cm, 0–5% MeOH/CHCl$_3$ gradient elution) to afford compound H (41 mg, 85%) as a film. $^1$H NMR (400 MHz, CDCl$_3$) δ 6.94 (s, 1 H), 6.52 (s, 1 H), 5.20–5.18 (m, 1 H), 4.02–4.00 (m, 1 H), 3.91–3.89 (m, 1 H), 2.99–2.96 (m, 1 H), 2.72–2.70 (m, 2 H), 2.66 (s, 3 H), 2.17–2.14 (m, 1 H), 2.10–2.09 (m, 1 H), 2.06 (s, 3 H), 1.95–1.91 (m, 1 H), 1.69–1.27 (m, 5 H), 1.14 (s, 3 H), 1.11 (s, 3 H), 0.98–0.87 (m, 24 H), 0.66–0.54 (m, 12 H), MS (ESI$^+$): 537.3 (M+H)$^+$.

I. [1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-4-oxa-17-azabicyclo[14.1.0]heptadecane-5,9-dione.

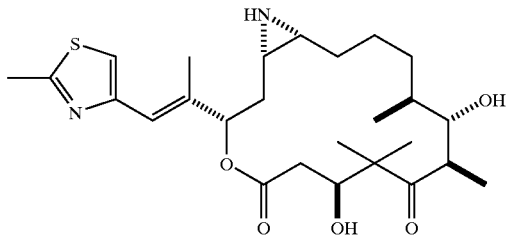

Compound H (17.2 mg, 24 μmol) was treated with 20% trifluoroacetic acid in methylene chloride (0.5 mL) at 0° C. under Ar for 10 min. The reaction mixture was concentrated under a constant stream of nitrogen at 0° C. and the residue was purified by radial chromatography (1 mm SiO$_2$ GF rotor, 2–10% MeOH—CHCl$_3$ gradient elution) to afford the title compound (10.6 mg, 86%) as a white solid; $^1$H NMR (400 MHz, CDCl$_3$) δ 6.84 (s, 1 H), 6.52 (s, 1 H), 5.46–5.44 (m, 1 H), 4.08–4.04 (m, 1 H), 3.69–3.68 (m, 1 H), 3.20–3.17 (m, 1 H), 2.57 (s, 3 H), 2.44–2.38 (m, 1 H), 2.34–2.30 (m, 1 H), 1.95–1.93 (br s, 4 H), 1.82–1.78 (m, 2 H), 1.71–1.53 (m, 2 H), 1.46–1.31 (m, 4 H), 1.27 (s, 3 H), 1.23–1.01 (m, 2 H), 0.99 (d, 3 H, J=6.9 Hz), 0.91 (s, 3 H) 0.8 (d, 3 H, J=6.9 Hz); $^{13}$C NMR (300 MHz, CDCl$_3$) δ 220.3, 171.2, 165.1, 152.4, 136.8, 119.2, 115.9, 76.5, 66.1, 75.4, 52.5, 45.0, 38.1, 34.6, 34.2, 30.1, 29.9, 26.1, 24.9, 22.9, 19.3, 17.6, 16.4, 15.4, 14.3. MS (ESI$^+$): 493.2 (M+H)$^+$.

EXAMPLE 13

[1S-[1R*,3R*(E),7R*,10S*,11R*,12R*,16R*]]-7,11-Dihydroxy-8,8,10,12,16-pentamethyl-3-[1-methyl-2-(2-methyl-4-thiazolyl)ethenyl]-4-azabicyclo[14.1.0]heptadecane-5,9-dione

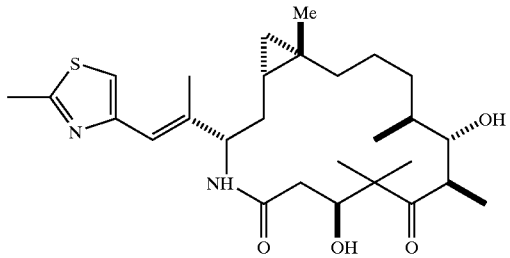

A. [4S-[4R*,7S*,8R*,9R*,16R*(E)]]-4,8-Dihydroxy-5,5,7,9,13-pentamethyl-16-[1-methyl-2-(2-methyl-4-thiazolyl)ethenyl]-1-oxa-13(Z)-cyclohexadecene-2,6-dione. [Epothilone D]

To anhydrous THF (5 ml) at −78° C. under argon was added WCl$_6$ (198 mg, 0.5 mmol) followed by nBuLi (0.625 ml of 1.6 M solution in hexanes, 1.0 mmol). The reaction was allowed to warm to room temperature over a 20 min period. An aliquot (0.50 ml, 0.05 mmol) of the tungsten reagent was removed and added to epothilone B (9.0 mg, 0.018 mmol) under argon and the reaction stirred for 15 min then quenched by the addition of saturated NaHCO$_3$ (1 ml). The reaction was extracted with EtOAc (3×1 ml). The combined extracts dried (Na$_2$SO$_4$), and filtered. The volatiles removed under vacuum. The residue was chromatographed with 35% EtOAc/hexanes to give compound A (7.0 mg, 0.014 mmol) in 80% yield. m/z: 492.3 (M+H)$^+$.

B. [4S-[4R*,7S*,8R*,9R*,16R*(E)]]-4,8-Bistriethylsilyloxy-5,5,7,9,13-pentamethyl-16-[1-methyl-2-(2-methyl-4-thiazolyl)ethenyl]-1-oxa-13(Z)-cyclohexadecene-2,6-dione. [Bis-Triethylsilyl Epothilone D]

To a solution of compound A (30 mg, 0.061 mmol) in anhydrous CH$_2$Cl$_2$ (1.25 mL) under argon were added N,N-diisopropylethylamine (0.16 mL, 0.92 mmol, 15 eq) followed by triethysilylchloride (0.10 mL, 0.61 mL, 10 eq). The reaction mixture was stirred for 18 hrs. The reaction mixture was cooled to 0° C. then 2,6-lutidine (0.021 mL, 0.18 mmol, 3 eq) was added followed by triethylsilyltrifluoromethanesulphonate (0.056 mL, 0.24 mmol, 4 eq). The reaction was stirred for 0.5 hr then poured into a 1:1 mixture of H$_2$O/saturated NaHCO$_3$ (1 mL) and extracted with CH$_2$Cl$_2$ (3×1 mL). The combined organics were dried (Na$_2$SO$_4$), filtered, and the volatiles were removed. The residue was chromatographed with 1% Et$_2$O/CH$_2$Cl$_2$ to give 35 mg of compound B (80% yield) as a clear glass. m/z: 720.5 (M+H)$^+$.

C. [1S-[1R*,3R*(E),7R*,10S*,11R*,12R*,16R*]]-7,11-Dihydroxy-8,8,10,12,16-pentamethyl-3-[1-methyl-2-(2-methyl-4-thiazolyl)ethenyl]-4-oxabicyclo[14.1.0]heptadecane-5,9-dione.

To a solution of diethylzinc (0.24 mL of 1.0 M in heptane, 0.24 mmol, 5 eq) in 1,2-dichloroethane (1.5 mL) at −15° C. under argon was added chloroiodomethane (0.035 mL, 0.48 mmol, 10 eq), and the mixture was stirred for 10 min. A solution of compound B (35 mg, 0.048 mmol) in 1,2-dichloroethane (0.40 mL) was slowly added, and the reaction mixture was stirred for 1.5 hrs. The reaction was quenched by addition of saturated NH$_4$Cl (1.5 mL) and extracted with CH$_2$Cl$_2$ (3×2 mL). The combined organics were dried (Na$_2$SO$_4$), filtered, and the volatiles removed in vacuo. To the residue was added 15% trifluoroacetic acid/CH$_2$Cl$_2$ (0.50 mL) and the reaction stirred for 15 min. The volatiles were removed under a stream of air and the residue was chromatographed with 70% EtOAc/hexanes to give 2.2 mg of compound C (10% yield-two steps) as a white film; m/z: 506.3 (M+H)$^+$.

Alternatively, sodium hydroxide (0.3 ml of 50% solution in H$_2$O) was added to compound 1B (109 mg, 0.15 mmol), PhCH$_2$(CH$_3$CH$_2$)$_3$NCl (0.7 mg, 0.002 mmol), and EtOH (0.03 ml) in CHBr$_3$ (1.0 ml). The resulting mixture was heated at 40° C. for 2 hr. The brown reaction mixture was diluted with H$_2$O (30 ml), extracted with CH$_2$Cl$_2$ (3×30 ml), dried over Na$_2$SO$_4$, concentrated and purified by flash chromatography (stepwise gradient: 5 to 25% Et$_2$O/hexanes) to afford a dibromocyclopropane intermediate as a light brown oil (40 mg, 30% yield). (M+H)$^+$ 892.3

Bu₃SnH (3.4 mmol, 0.91 ml) was added to the dibromocyclopropane intermediate (0.34 mmol, 305 mg) and 2,2-azobisisobutyronitrile (0.034 mmol, 6 mg) in hexanes (7.0 ml). The reaction mixture was heated at 70° C. for 5 hr. The reaction was concentrated and purified by flash chromatography (stepwise gradient: hexanes to 20% Et₂O/hexanes) to afford a reduced cyclopropane intermediate as a clear film (228 mg, 91%). (M+H)⁺ 734.7.

The preceding cyclopropane intermediate(0.31 mmol, 228 mg) was dissolved in CF₃CO₂H/CH₂Cl₂ (20% solution by volume, 10 ml) and stirred at −15° C. for 1.5 hr. The reaction mixture was concentrated and purified by flash chromatography (70% EtoAc/Hexanes) to afford compound C as a clear oil (111 mg, 71%). (M+H)⁺ 506.3. ¹H NMR (CDCl₃, 400 MHz) d 7.04 (s, 1H), 6.64 (s, 1H), 5.16 (dd, J=8.0, 3.4 Hz, 1H), 4.17 (dd, J=9.5, 2.8 Hz, 1H), 3.79–3.83 (m, 1H), 3.23 (dq, J=6.7, 4.5 Hz, 1H), 2.79 (s, 3H), 2.52 (dd, J=15.1, 9.7 Hz, 1H), 2.41 (dd, J=15.2, 2.9 Hz, 1H), 1.98–2.02 (m, 1H), 2.00 (s, 3H), 1.63–1.73 (m, 1H), 1.40–1.58 (m, 5H), 1.36 (s, 3H), 1.20–1.33 (m, 1H), 1.11–1.17 (m, 1H), 1.15 (d, J=6.8 Hz, 3H), 1.08 (s, 3H), 0.96 (d, J=7.0 Hz, 3H), 0.94 (s, 3H), 0.40–0.54 (m, 1H), 0.37 (dd, J=8.8, 4.1 Hz, 1H), −0.14-(−0.10) (m, 1H).

D. [1S-[1R*,3R*(E),7R*,10S*,11R*,12R*,16R*]]-7,11-Dihydroxy-8,8,10,12,16-pentamethyl-3-[1-methyl-2-(2-methyl 4-thiazolyl)ethenyl]-4-azabicyclo[4.1.0]heptadecane-5,9-dione.

A suspension of compound C (26 mg, 51 mmol) and sodium azide (6.7 mg, 0.10 mmol) in a THF-H₂O mixture (2:1, 1.0 mL) was degassed for 15 min with nitrogen. To the mixture was added a catalytic amount (12 mg, 10 mmol) of tetrakis(triphenylphosphine) palladium(0) under Ar. The reaction mixture was warmed to 45° C. for 1 hr and cooled to 25° C. The resulting yellow homogeneous solution was directly treated with a 1.0 M solution of trimethylphosphine in THF (0.11 mL, 0.11 mmol) at 25° C. and the reaction mixture was stirred for 1 hr at ambient temperature.

The amino acid-containing mixture was then diluted with MeCN-DMF (12:1, 1.9 mL), cooled to 0° C. and treated with 1-hydroxybenzotriazole hydrate (7.0 mg, 51 mmol) followed by 1-(3-dimethylaminopropyl)-3-ethylcarbodiimide hydrochloride (25 mg, 0.13 mmol). The reaction mixture was gradually warmed to 25° C., stirred for 3 hr, diluted with H₂O (5 mL) and extracted with EtOAc (3×5 mL). The organic extracts were washed with H₂O (8 mL), saturated aqueous NaHCO₃ (2×8 mL), and saturated aqueous NaCl (8 mL). The organic extracts were dried (Na₂SO₄) and concentrated in vacuo. The residue was purified by radial chromatography (1 mm SiO₂ rotor, 2% MeOH—CHCl₃) to afford the title compound (film, 3.0 mg, 12% overall yield), along with a minor amount of a diastereomer (5:1 ratio by ¹H NMR). (M+H)⁺ 505.4

EXAMPLE 14

[1S-[1R*,3R*(E),7R*,10S*,11R*,12R*,16S*]]-17-Dichloro-7,11-dihydroxy-8,8,10,12,16-pentamethyl-3-[1-methyl-2-(2-methyl-4-thiazolyl)ethenyl]-4-azabicyclo[14.1.0]heptadecane-5,9-dione

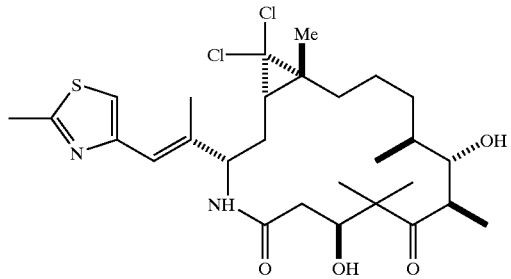

A. [1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione.

A suspension of epothilone B (5.06 g, 9.97 mmol) and sodium azide (0.777 g, 12.0 mmol) in a THF-H₂O mixture (5:1, 96 mL) was degassed for 15–20 min with nitrogen and then treated with a catalytic amount (1.2 g, 0.997 mmol) of tetrakis(triphenylphosphine) palladium (0) under Ar. The reaction mixture was warmed to 45° C. for 20 min and cooled to 25° C.

The resulting bright yellow homogeneous solution was directly treated with a 1.0 M solution of trimethylphosphine in THF (24.9 mL, 24.9 mmol) at 25° C. and the reaction mixture was stirred for 1–2 hr at ambient temperature.

The amino acid-containing mixture was then diluted with MeCN-DMF (20:1, 450 mL), cooled to 0° C. and treated with 1-hydroxybenzotriazole hydrate (1.35 g, 9.97 mmol) followed by 1-(3-dimethylaminopropyl)-3-ethylcarbodimide hydrochloride (4.78 g, 24.9 mmol). The reaction mixture was warmed to 25° C., stirred for 12 hr and extracted with EtOAc (4×200 mL). The organic extracts were washed with H₂O (400 mL), saturated aqueous NaHCO₃ (400 mL), and saturated aqueous NaCl (400 mL). The organic extracts were dried (Na₂SO₄) and concentrated in vacuo. The residue was purified by flash chromatography (SiO₂, 5.0×25 cm, 2% MeOH—CHCl₃) and then HPLC (YMC S-15 ODS 50×500 mm column, 38 to 95% MeCN/H₂O, gradient (40 min), 50 mL/min flow rate). The appropriate fractions were concentrated in vacuo and the residue was lyophilized from aqueous acetonitrile to afford compound A (0.998 g, 20%), as a white lyopholizate. MS (ESI⁺): 507.2 (M+H)⁺; MS(ESI⁻): 505.4 (M−H)⁻.

B. [4S-[4R*,7S*,8R*,9R*,16R*(E)]]-4,8-Dihydroxy-5,5,7,9,13-pentamethyl-16-[1-methyl-2-(2-methyl-4-thiazolyl)ethenyl]-1-aza-13(Z)-cyclohexadecene-2,6-dione.

Tungsten chloride (1.98 g, 5.00 mmol) was added in one portion to pre-cooled THF (50 ml) at −78° C., and the resulting mixture was stirred for 5 min. n-BuLi (1.6 M in hexanes, 6.25 ml, 10.0 mmol) was added to the suspension which was kept at −78° C. for 10 min, then warmed to room temperature over 30 min. After 30 additional min at room temperature, the reaction mixture was added to compound A (0.351 g, 0.690 mmol) via syringe. After 15 min, the reaction mixture was cooled to 0° C., diluted with ethyl acetate (10 ml), and quenched with saturated sodium bicarbonate (15 ml). The reaction mixture was extracted with ethyl acetate (5×20 ml), dried over sodium sulfate, concentrated and purified by reverse phase HPLC (solvent A=5:95, acetonitrile:H$_2$O, solvent B=95:5, acetonitrile:H$_2$O; gradient: 40–100% solvent B over 40 minutes; Flow rate: 40 ml/min, 50×500 mm YMC ODS S-15 column) to afford compound B (0.164 g, 36%) as a white solid. (M+H)$^+$ 491.3

C. [4S-[4R*,7S*,8R*,9R*,16R*(E)]]-4,8-Bis(t-butyldimethylsilyloxy)-5,5,7,9,13-pentamethyl-16-[1-methyl-2-(2-methyl-4-thiazolyl)ethenyl]-1-aza-13(Z)-cyclohexadecene-2,6-dione.

To a solution of compound B (19 mg, 0.039 mmol) in CH$_2$Cl$_2$ (1.5 ml) at 0° C. was added lutidine (0.023 mL, 0.20 mmol). This was followed by addition of tert-butyldimethylsilyl trifluoromethanesulfonate (0.045 mL, 0.20 mmol) over 2 hr. The reaction mixture was poured into saturated NaHCO$_3$ (2 ml) and extracted with CH$_2$Cl$_2$ (3×2 ml). The combined organic extracts were dried (Na$_2$SO$_4$), filtered and concentrated. The residue was chromatographed with 20% EtOAc/hexanes to give compound C (19 mg, 68%) as a white solid. (M+H)$^+$719

D. 1S-[1R*,3R*(E),7R*,10S*,11R*,12R*,16S*]]-17-Dichloro-7,11-bis(t-butyldimethylsilyloxy)-8,8,10,12,16-pentamethyl-3-[1-methyl-2-(2-methyl-4-thiazolyl)ethenyl]-4-azabicyclo[14.1.0]heptadecane-5,9-dione.

To a solution of compound C (9.6 mg, 0.013 mmol) in CHCl$_3$ (0.10 ml) was added benzyltriethylammonium chloride (0.00026 mmol, <1 mg), EtOH (0.002 ml), and 50% NaOH(aq) (0.015 ml, 0.29 mmol). The reaction mixture was vigorously stirred for 2 hr and then directly chromatographed (15% EtOAc/hexanes) to give compound D (2.4 mg, 22%) as a clear oil. (M+H)$^+$801

E. 1S-[1R*,3R*(E),7R*,10S*,11R*,12R*,16S*]]-17-Dichloro-7,11-dihydroxy-8,8,10,12,16-pentamethyl-3-[1-methyl-2-(2-methyl-4-thiazolyl)ethenyl]-4-azabicyclo [14.1.0]heptadecane-5,9-dione.

To compound D (2.2 mg, 0.0027 mmol) at −15° C. was added 20% trifluoroacetic acid/CH$_2$Cl$_2$ (0.20 ml). The reaction mixture was warmed to 0° C. and stirred for 2 hr. The volatiles were removed under a stream of air and the residue was chromatographed with 60% EtOAc/hexanes to afford the title compound (1.2 mg, 75%) as a white solid, (M+H)$^+$ 573.

EXAMPLE 15

[1S-[1R*,3R*(E),7R*,10S,11R*,12R*,16S*]]-17-Benzyl-7,11-dihydroxy-8,8,10,12-tetramethyl-3-[1-methyl-2-(2-methyl-4-thiazolyl)ethenyl]-4-oxa-17-azabicyclo[14.1.0]heptadecane-5,9-dione.

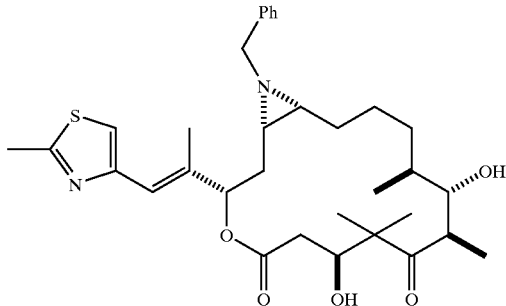

(Prepared by the method of example 8, using benzyl bromide and potassium carbonate/18-crown-6.) $^1$H NMR (400 MHz, CDCl$_3$) δ 7.31 (s, 5 H), 6.99 (s, 1 H), 6.67 (s, 1 H), 5.50–5.47 (m, 1 H), 4.09–4.00 (m, 1 H), 3.78–3.73 (m, 2 H), 3.37–3.33 (m, 1 H), 3.20–3.17 (m, 1 H), 2.73 (s, 3 H), 2.54 (dd, 1 H, J=13.8, 10.2 Hz), 2.46 (dd, 1 H, J=13.8, 3.0 Hz), 2.08 (s, 3 H), 1.98–1.84 (m, 4 H), 1.58–1.48 (m, 3 H), 1.42–1.37 (m, 4 H), 1.36 (s, 3 H), 1.28–1.22 (m, 2 H), 1.16 (d, 3 H, J=6.8 Hz), 1.11 (s, 3 H), 0.95 (d, 3 H, J=6.9 Hz); LRMS (ESI$^+$): 583.4 (M+H)$^+$.

EXAMPLE 16

[1S-[1R*,3R*(E),7R*,10S,11R*,12R*,16S*]]-17-Sulfonylurea-7,11-dihydroxy-8,8,10,12-tetramethyl-3-[1-methyl-2-(2-methyl-4-thiazolyl)ethenyl]-4-oxa-17-azabicyclo[14.1.0]heptadecane-5,9-dione.

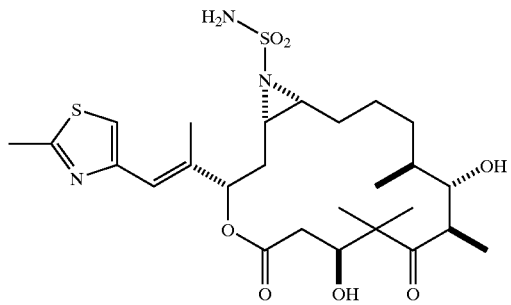

Prepared with sulfamoyl chloride in the presence of diisopropylethylamine.

$^1$H NMR (400 MHz, CDCl$_3$) δ 6.89 (s, 1 H), 6.64 (s, 1 H), 5.39 (dd, 1 H, J=6.9, 2.3 Hz), 5.20 (br s, 2 H, NH$_2$), 4.15–4.09 (m, 1 H), 3.82–3.77 (m, 2 H), 3.18–3.10 (m, 1 H), 2.65–2.62 (m, 1 H), 2.62 (s, 3 H), 2.51 (dd, 1 H, J=14.6, 10.4 Hz), 2.48–2.43 (m, 1 H), 2.40 (dd, 1 H, J=14.6, 3.1 Hz), 2.34–2.29 (m, 1 H), 2.06–2.03 (m, 1 H), 1.95 (s, 3 H), 1.93–1.86 (m, 2 H), 1.74–1.64 (m, 1 H), 1.63–1.34 (m, 5 H), 1.33 (s, 3 H), 1.08 (d, 3 H, J=6.9 Hz), 1.03 (s, 3H), 0.91 (d, 3 H, J=7.0 Hz); LRMS (ESI$^+$): 572.4 (M+H)$^+$.

EXAMPLE 17

[1S-[1R*,3R*(E),7R*,10S,11R*,12R*,16S*]]-17-N-Methylsulfonylurea-7,11-dihydroxy-8,8,10,12-tetramethyl-3-[1-methyl-2-(2-methyl-4-thiazolyl) ethenyl]-4-oxa-17-azabicyclo[14.1.0]heptadecane-5,9-dione.

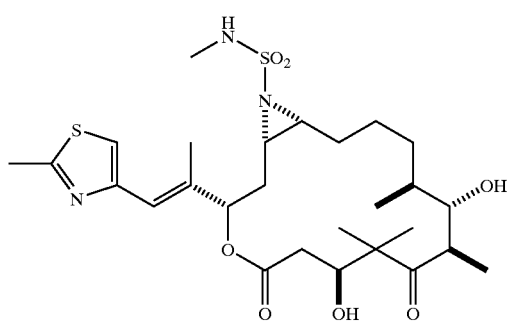

Via N-methylsulfamoyl chloride in the presence of diisopropylethylamine.

$^1$H NMR (400 MHz, CDCl$_3$) δ 6.99 (s, 1 H), 6.61 (s, 1 H), 5.37 (dd, 1 H, J=9.5, 2.3 Hz), 4.65 (dd, 1 H, J=10.3, 5.0 Hz), 4.16–4.11 (m, 1 H), 3.83 (dd, 1 H, J=8.7, 4.4 Hz), 3.75 (d,

1 H, J=6.5 Hz), 3.20–3.18 (m, 1 H), 2.89 (d, 3 H, J=5.2 Hz), 2.74–2.70 (m, 1 H), 2.71 (s, 3 H), 2.64–2.55 (m, 1 H), 2.56 (dd, 1 H, J=14.8, 10.2 Hz), 2.46 (dd, 1 H, J=14.8, 3.2 Hz), 2.29–2.18 (m, 1 H), 2.08 (s, 3 H), 1.92–1.84 (m, 1 H), 1.83–1.75 (m, 2 H), 1.57–1.39 (m, 6 H), 1.38 (s, 3 H), 1.19 (d, 3 H, J=6.7 Hz) 1.15 (s, 3 H), 1.02 (d, 3 H, J=7.0 Hz); HRMS (ESI$^+$) m/z (M$^+$+H) calcd for $C_{27}H_{43}N_3O_7S_2$: 586.2621, found: 586.2635.

EXAMPLE 18

[1S-[1R*,3R*(E),7R*,10S*,11R*,12R*,16S*]]-7,11-Dihydroxy-N,N,8,8,10,12-hexamethyl-3-[1-methyl-2-(2-methyl-4-thiazolyl)ethenyl]-5,9-dioxo-4-oxa-17-azabicyclo[14.1.0]heptadecane-17-sulfonamide.

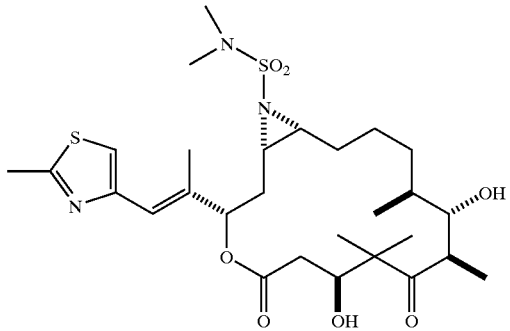

Via N,N-dimethylsulfamoyl chloride in the presence of diisopropylethylamine.
$^1$H NMR (400 MHz, CDCl$_3$) δ 6.99 (s, 1 H), 6.57 (s, 1 H), 5.32 (dd, 1 H, J=10.2, 2.1 Hz), 4.15–4.12 (m, 1 H), 3.83–3.81 (m, 1 H), 3.65–3.62 (m, 1 H), 3.19–3.16 (m, 1 H), 2.88 (s, 6 H), 2.73–2.69 (m, 1 H), 2.71 (s, 3 H), 2.62–2.55 (m, 1 H), 2.54–2.50 (m, 1 H), 2.52 (dd, 1 H, J=15.0, 10.0 Hz), 2.45 (dd, 1 H, J=15.0, 3.0 Hz), 2.29–2.25 (m, 1H), 2.07 (s, 3 H), 1.86–1.79 (m, 2 H), 1.79–1.75 (m, 1 H), 1.56–1.40 (m, 5 H), 1.37 (s, 3 H), 1.21 (d, 3 H, J=6.9 Hz), 1.17 (s, 3 H), 1.03 (d, 3 H, J=6.9 Hz); HRMS (ESI$^+$) m/z (M$^+$+H) calcd for $C_{28}H_{45}N_3O_7S_2$: 600.2777, found: 600.2761.

EXAMPLE 19

[1S-[1R*,3R*(E),7R*,10S*,11R*,12R*,16S*]]-17-Morpholinosulfonyl-7,11-dihydroxy-8,8,10,12-tetramethyl-3-[1-methyl-2-(2-methyl-4-thiazolyl)ethenyl]-4-oxa-17-azabicyclo[14.1.0]heptadecane-5,9-dione.

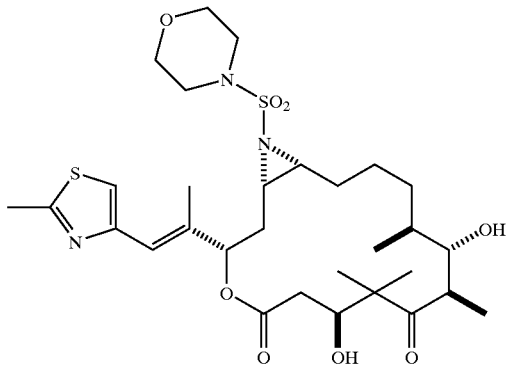

Via N-chlorosulfonyl morpholine in the presence of diisopropylethylamine.

$^1$H NMR (400 MHz, CDCl$_3$) δ 6.92 (s, 1 H), 6.50 (s, 1 H), 5.23 (d, 1 H, J=9.3 Hz), 4.06–4.04 (m, 1 H), 3.73–3.72 (m, 1 H), 3.70–3.58 (m, 4 H), 3.20–3.17 (m, 4 H), 3.10–3.08 (m, 1 H), 2.66–2.63 (m, 1 H), 2.64 (s, 3 H), 2.64–2.62 (m, 1 H), 2.61–2.57 (m, 1 H), 2.56 (dd, 1 H, J=14.8, 10.2 Hz), 2.46 (dd, 1 H, J=14.8, 3.2 Hz), 2.19–2.14 (m, 1 H), 2.02 (s, 3 H), 1.80–1.72 (m, 1 H), 1.72–1.32 (m, 8 H), 1.29 (s, 3 H), 1.12 (d, 3 H, J=6.7 Hz), 1.08 (s, 3 H), 0.95 (d, 3 H, J=6.9 Hz); LRMS (ESI$^+$): 642.4 (M+H)$^+$.

EXAMPLE 20

[1S-[1R*,3R*(E),7R*,10S,11R*,12R*,16S*]]-7,11-dihydroxy-8,8,10,12-tetramethyl-3-[1-methyl-2-(2-methyl-4-thiazolyl)ethenyl]-4-oxa-17-azabicyclo[14.1.0]heptadecane-5,9-dione-17-carboxylic acid phenyl ester.

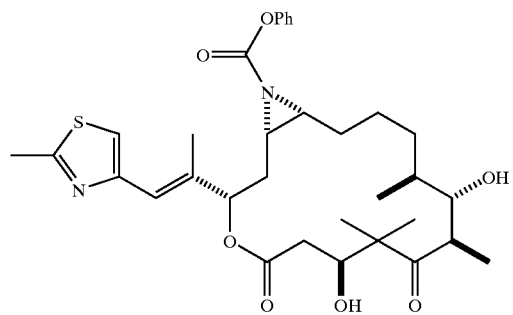

(Via phenyl chloroformate in the presence of diisopropylethylamine.): $^1$H NMR (400 MHz, CDCl$_3$) δ 7.39–7.34 (m, 2 H), 7.24–7.20 (m, 1 H), 7.11–7.08 (m, 2 H), 6.93 (s, 1 H), 6.61 (s, 1 H), 5.44 (d, 1 H, J=8.6 Hz), 4.19–4.12 (m, 1 H), 3.87–3.83 (m, 2 H), 3.21–3.18 (m, 1 H), 2.75–2.62 (m, 1 H), 2.67 (s, 3 H), 2.62–2.56 (m, 1 H), 2.55 (dd, 1 H, J=14.4, 10.2 Hz), 2.47 (dd, 1 H, J=14.4, 3.3 Hz), 2.32–2.27 (m, 1 H), 2.04 (s, 3 H), 1.92–1.84 (m, 4 H), 1.81–1.44 (m, 5 H), 1.37 (s, 3 H), 1.17 (d, 3 H, J=6.8 Hz), 1.13 (s, 3 H), 1.01 (d, 3 H, J=6.9 Hz); HRMS (ESI$^+$) m/z (M$^+$+H) calcd for $C_{33}H_{44}N_2O_7S$: 613.2948, found: 613.2958.

EXAMPLE 21

[1S-[1R*,3R*(E),7R*,10S,11R*,12R*,16S*]]-17-Acetyl-7,11-dihydroxy-8,8,10,12-tetramethyl-3-[1-methyl-2-(2-methyl-4-thiazolyl)ethenyl]-4-oxa-17-azabicyclo[14.1.0]heptadecane-5,9-dione.

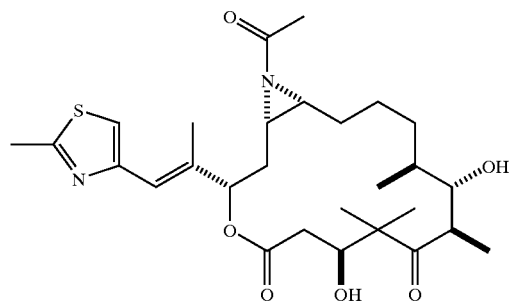

(Via acetyl chloride in the presence of diisopropylethylamine.): $^1$H NMR (400 MHz, CDCl$_3$) δ 6.99 (s, 1 H), 6.58 (s, 1 H), 5.39–5.37 (m, 1 H), 3.86–3.83 (m, 1 H), 3.75–3.73 (m, 1 H), 3.20–3.18 (m, 1 H), 2.71 (s, 3 H), 2.57–2.46 (m, 3 H), 2.42–2.38 (m, 1 H), 2.29–2.25 (m, 1 H), 2.14 (s, 3 H) 2.11 (s, 3 H), 1.87–1.74 (m, 4 H), 1.56–1.41 (m, 4 H), 1.37 (s, 3 H), 1.20 (d, 3 H, J=6.8 Hz), 1.16 (s, 3 H), 1.03 (d, 3 H, J=6.9 Hz). MS (ESI$^+$): 535.3 (M+H)$^+$.

EXAMPLE 22

1S-[1R*,3R*(E),7R*,10S,11R*,12R*,16S*]]-17-Phenylcarbonyl-7,11-dihydroxy-8,8,10,12-tetramethyl-3-[1-methyl-2-(2-methyl-4-thiazolyl)ethenyl]-4-oxa-17-azabicyclo[14.1.0]heptadecane-5,9-dione.

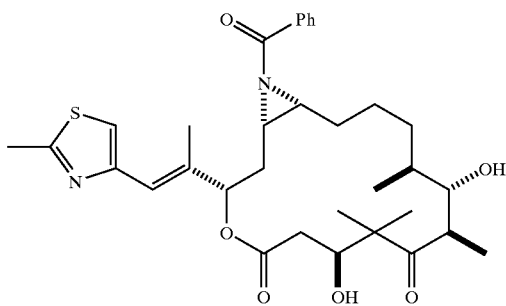

(Via benzoyl chloride in the presence of diisopropylethylamine.): $^1$H NMR (400 $^1$H NMR (400 MHz, CDCl$_3$) δ 7.96–7.93 (m, 2 H), 7.60–7.56 (m, 1 H), 7.49–7.45 (m, 2 H), 7.00 (s, 1 H), 6.59 (s, 1 H), 5.37 (d, 1 H, J=8.1 Hz), 3.85–3.83 (m, 1 H), 3.72 (br s, 1 H), 3.21–3.18 (m, 1 H), 2.72 (s, 3 H), 2.69–2.43 (m, 6 H), 2.06 (s, 3 H), 2.06–1.93 (m, 4 H), 1.79–1.71 (m, 2 H), 1.64–1.45 (m, 3 H), 1.39 (s, 3 H), 1.21 (d, 3 H), J=6.8 Hz), 1.17 (s, 3 H), 1.05 (d, 3 H, J=6.9 Hz). MS (ESI$^+$) 597.3 (M$^+$+H).

EXAMPLE 23

[1S-[1R*,3R*(E),7R*,10S,11R*,12R*,16S*]]-17-(2-Thienyl)carbonyl-7,11-dihydroxy-8,8,10,12-tetramethyl-3-[1-methyl-2-(2-methyl-4-thiazolyl)ethenyl]-4-oxa-17-azabicyclo[14.1.0]heptadecane-5,9-dione.

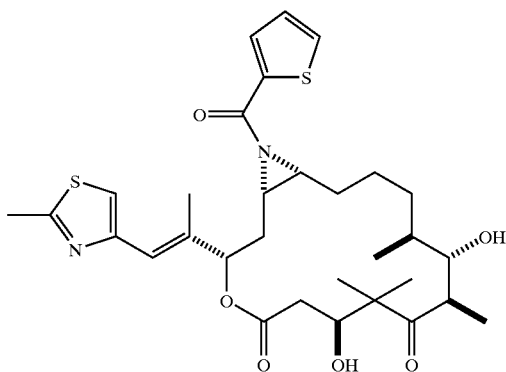

Via thiophene-2-carbonyl chloride in the presence of diisopropylethylamine.

$^1$H NMR (400 MHz, CDCl$_3$) δ 7.76 (d, 1 H, J=3.9 Hz), 7.58 (d, 1 H, J=4.6 Hz), 7.14 (dd, 1 H, J=4.3, 3.9 Hz), 7.00 (s, 1 H), 6.59 (s, 1 H), 5.40–5.37 (m, 1 H), 3.85–3.84 (m, 1 H), 3.73–3.70 (m, 1 H), 3.21–3.18 (m, 1 H), 2.77–2.76 (m, 1 H), 2.72 (s, 3 H), 2.60–2.41 (m, 4 H), 2.13 (s, 3 H), 2.03–1.99 (m, 1 H), 1.76–1.74 (m, 1 H), 1.57–1.43 (m, 6 H), 1.38 (s, 3 H), 1.21 (d, 3 H, J=6.8 Hz), 1.17 (s, 3 H), 1.05 (d, 3 H, J=6.9 Hz). MS (ESI$^+$): 603.3 (M+H)$^+$.

EXAMPLE 24

[1S-[1R*,3R*(E),7R*,10S,11R*,12R*,16S*]]-17-N-Ethylcarbamoyl-7,11-dihydroxy-8,8,10,12-tetramethyl-3-[1-methyl-2-(2-methyl-4-thiazolyl)ethenyl]-4-oxa-17-azabicyclo[14.1.0]heptadecane-5,9-dione.

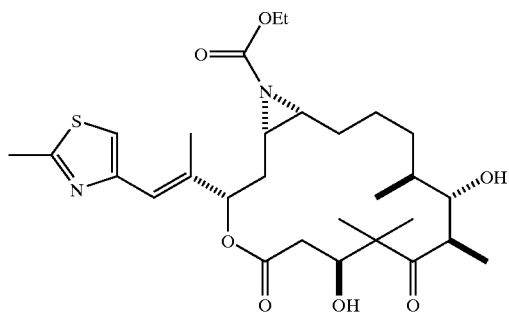

(Via ethyl chloroformate in the presence of diisopropylethylamine.): $^1$H NMR (400 MHz, CDCl$_3$) δ 6.98 (s, 1 H), 6.63 (s, 1 H), 5.44–5.32 (m, 1 H), 4.19–4.11 (m, 3 H), 3.91 (br s, 1 H), 3.86 (br s, 1 H), 3.22–3.18 (m, 1 H), 2.71 (s, 3 H), 2.58–2.39 (m, 4 H), 2.24–2.20 (m, 1 H), 2.11 (s, 3 H), 1.90–1.76 (m, 3 H), 1.55–1.41 (m, 3 H), 1.37 (s, 3 H), 1.30–1.27 (m, 3 H), 1.18 (d, 3 H, J=6.8 Hz), 1.13 (s, 3 H), 1.01 (d, 3 H, J=6.9 Hz). MS (ESI$^+$): 565.3 (M+H)$^+$.

EXAMPLE 25

[1S-[1R*,3R*(E),7R*,10S,11R*,12R*,16S*]]-17-N-n-Propylsulfonyl-7,11-dihydroxy-8,8,10,12-tetramethyl-3-[1-methyl-2-(2-methyl-4-thiazolyl)ethenyl]-4-oxa-17-azabicyclo[14.1.0]heptadecane-5,9-dione.

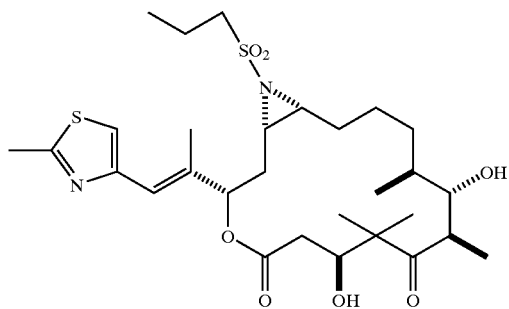

(Via propanesulfonyl chloride in the presence of diisopropylethylamine.): $^1$H NMR (400 MHz, CDCl$_3$) δ 6.99 (s, 1 H), 6.57 (s, 1 H), 5.34 (d, 1 H, J=8.0 Hz), 3.83–3.82 (m, 1 H), 3.63–3.62 (m, 1 H), 3.18–3.15 (m, 1 H), 3.11–3.07 (m, 2 H), 2.70 (s, 3 H), 2.67–2.51 (m, 1 H), 2.47–2.43 (m, 1 H), 2.29–2.25 (m, 1 H), 2.32–2.27 (m, 1 H), 2.10 (s, 3 H), 2.02–1.70 (m, 5 H), 1.55–1.46 (m, 3 H), 1.37 (s, 3 H), 1.21–1.08 (m, 12 H), 1.03 (d, 3 H, J=6.9 Hz). MS (ESI$^+$) 599.3 (M$^+$+H).

EXAMPLE 26

[1S-[1R*,3R*(E),7R*,10S*,11R*,12R*,16S*]]-17-(2-thienyl)sulfonyl-7,11-dihydroxy-8,8,10,12-tetramethyl-3-[1-methyl-2-(2-methyl-4-thiazolyl)ethenyl]-4-oxa-17-azabicyclo[14.1.0]heptadecane-5,9-dione.

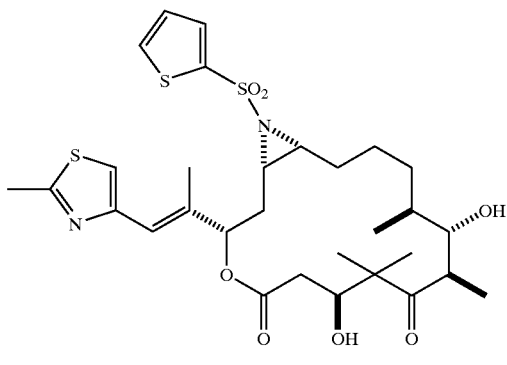

Via 2-thienylsulfonyl chloride in the presence of diisopropylethylamine.

$^1$H NMR (400 MHz, CDCl$_3$) δ 7.70 (m, 2 H), 7.15 (dd, 1 H, J=4.3, 3.9 Hz), 6.99 (s, 1 H), 6.58 (s, 1 H), 5.36–5.34 (m, 1 H), 3.83–3.80 (m, 1 H), 3.70–3.69 (m, 1 H), 3.18–3.16 (m, 1 H), 2.88–2.83 (m, 1 H), 2.76–2.73 (m, 1 H), 2.71 (s, 3 H), 2.59–2.53 (m, 2 H), 2.46–2.41 (m, 1 H), 2.19–2.07 (m, 1 H), 2.06 (s, 3 H), 1.92–1.89 (m, 1 H), 1.87–1.70 (m, 3 H), 1.49–1.29 (m, 3 H), 1.27 (s, 3 H), 1.18 (d, 3H, J=6.8 Hz), 1.16 (s, 3 H), 1.00 (d, 3 H, J=6.9 Hz). MS (ESI$^+$): 639.2 (M+H)$^+$.

The following compounds were prepared in similar fashion:

EXAMPLE 27

[1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-5,9-dioxo-4-oxa-17-azabicyclo[14.1.0]heptadecane-17-carboxylic acid phenylmethyl ester.

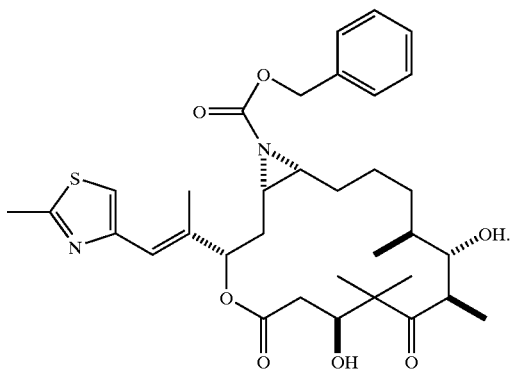

(M + H)$^+$ 627

EXAMPLE 28

[1S-[1R*,3R*(E),7R*,10S*,11R*,12R*,16S*]]-7,11-Dihydroxy-8,8,10,12-tetramethyl-17-[(1-methyl-1H-imidazol-4-yl)sulfonyl]-3-[1-methyl-2-(2-methyl-4-thiazolyl)ethenyl]-4-oxa-17-azabicyclo[14.1.0]heptadecane-5,9-dione.

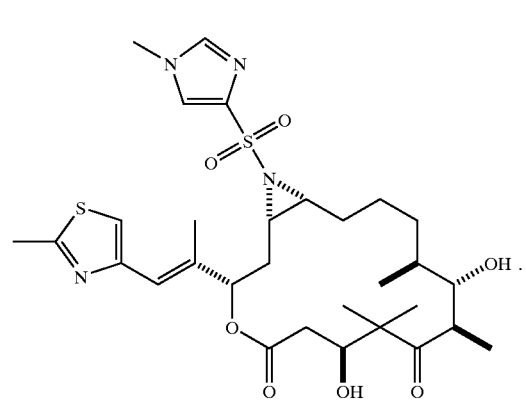

(M + H)$^+$ 637

EXAMPLE 29

[1S-[1R*,3R*(E),7R*,10S*,11R*,12R*,16S*]]-7,11-Dihydroxy-17-(methoxyacetyl)-8,8,10,12-tetramethyl-3-[1-methyl-2-(2-methyl-4-thiazolyl)ethenyl]-4-oxa-17-azabicyclo[14.1.0]heptadecane-5,9-dione.

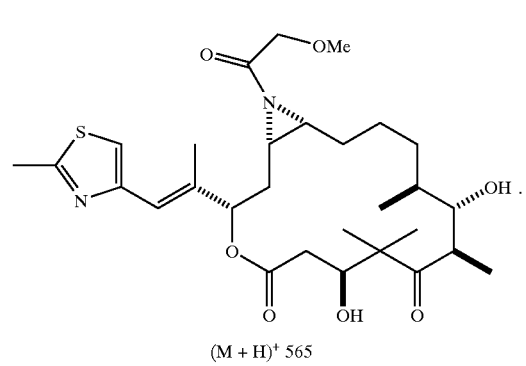

(M + H)$^+$ 565

EXAMPLE 30

[1S-[1R*,3R*(E),7R*,10S*,11R*,12R*,16S*]]-17-
(2-Oxopropanoyl)-7,11-dihydroxy-8,8,10,12-
tetramethyl-3-[1-methyl-2-(2-methyl-4-thiazolyl)
ethenyl]-4-oxa-17-azabicyclo[14.1.0]heptadecane-5,
9-dione.

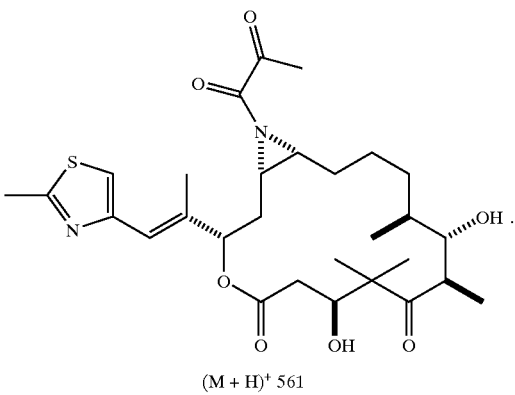

(M + H)$^+$ 561

Further compounds prepared according to the methods described above include the following:

[1S[1R*,3R*(E),7R*,10S*,11R*,12R*,16R*]]-7,11-Dihydroxy-8,8,10,12,16-pentamethyl-3-[1-methyl-2-(2-methyl-4-thiazolyl)ethenyl]-4-oxabicyclo[14.1.0]heptadecane-5,9-dione;

[1S-[1R*,3R*(E),7R*,10S*,11R*,12R*,16S*]]-17-Dichloro-7,11-dihydroxy-8,8,10,12,16-pentamethyl-3-[1-methyl-2-(2-methyl-4-thiazolyl)ethenyl]-4-oxabicyclo[14.1.0]heptadecane-5,9-dione;

[1S-[1R*,3R*(E),7R*,10S*,11R*,12R*,16S*]]-17-Dibromo-7,11-dihydroxy-8,8,10,12,16-pentamethyl-3-[1-methyl-2-(2-methyl-4-thiazolyl)ethenyl]-4-oxabicyclo[14.1.0]heptadecane-5,9-dione;

[1S-[1R*,3R*(E),7R*,10S*,11R*,12R*,16R*]]-7,11-Dihydroxy-8,8,10,12-tetramethyl-3-[1-methyl-2-(2-methyl-4-thiazolyl)ethenyl]-4-oxabicyclo[14.1.0]heptadecane-5,9-dione;

[1S-[1R*,3R*(E),7R*,10S*,11R*,12R*,16S*]] 17-Dichloro-7,11-dihydroxy-8,8,10,12,16-pentamethyl-3-[1-methyl-2-(2-methyl-3-oxo-4-thiazolyl)ethenyl]-4-oxabicyclo[14.1.0]heptadecane-5,9-dione;

[1S-[1R*,3R*(E),7R*,10S*,11R*,12R*,16R*]]-7,11-Dihydroxy-8,8,10,12,16-pentamethyl-3-[1-methyl-2-(2-methyl-3-oxo-4-thiazolyl)ethenyl]-4-oxabicyclo[14.1.0]heptadecane-5,9-dione;

[1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-5,9-dioxo-4-oxa-17-azabicyclo[14.1.0]heptadecane-17-carboxylic acid, 1,1-dimethylethyl ester;

[1S-[1R*,3R*(E),10S*,11R*,12R*,16S*]]-11-Hydroxy-8,8,10,12-tetramethyl-3-[1-methyl-2-(2-methyl-4-thiazolyl)ethenyl]-4,18-dioxabicyclo[14.2.0]octadec-6(E)-ene-5,9-dione;

[1S-[11R*,3R*(E),7R*,10S*,11R*,12R*,16R*]]-7,11-Dihydroxy-8,8,10,12,16-pentamethyl-3-[1-methyl-2-(2-methyl-4-thiazolyl)ethenyl]-4-azabicyclo[14.1.0]heptadecane-5,9-dione;

[1S-[1R*,3R*(E),7R*,10S*,11R*,12R*,16S*]]-17-Dichloro-7,11-dihydroxy-8,8,10,12,16-pentamethyl-3-[1-methyl-2-(2-methyl-4-thiazolyl)ethenyl]-4-azabicyclo[14.1.0]heptadecane-5,9-dione;

[1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-5,9-dioxo-4-oxa-17-azabicyclo[14.1.0]heptadecane-17-carboxylic acid phenyl ester, (M+H)$^+$ 613;

[1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-5,9-dioxo-4-oxa-17-azabicyclo[14.1.0]heptadecane-17-carboxylic acid phenylmethyl ester, (M+H)$^+$ 627;

[1S-[1R*,3R*(E),7R*,10S*,11R*,12R*,16S*]]-7,11-Dihydroxy-N,N,8,8,10,12-hexamethyl-3-[1-methyl-2-(2-methyl-4-thiazolyl)ethenyl]-5,9-dioxo-4-oxa-17-azabicyclo[14.1.0]heptadecane-17-sulfonamide, (M+H)+ 600;

[1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-17-(2-thienylsulfonyl)-4-oxa-17-azabicyclo[14.1.0]heptadecane-5,9-dione, (M+H)$^+$639;

[1S-[1R*,3R*(E),7R*,10S*,11R*,12R*,16S*]]-7,11-Dihydroxy-8,8,10,12-tetramethyl-17-[(1-methyl-1H-imidazol-4-yl)sulfonyl]-3-[1-methyl-2-(2-methyl-4-thiazolyl)ethenyl]-4-oxa-17-azabicyclo[14.1.0]heptadecane-5,9-dione, (M+H)$^+$ 637;

[1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-17-(propylsulfonyl)-4-oxa-17-azabicyclo[14.1.0]heptadecane-5,9-dione, (M+H)$^+$ 599;

[1S-[1R*,3R*(E),7R*,10S*,11R*,12R*,16S*]]-17-Acetyl-7,11-dihydroxy-8,8,10,12-tetramethyl-3-[1-methyl-2-(2-methyl-4-thiazolyl)ethenyl]-4-oxa-17-azabicyclo[14.1.0]heptadecane-5,9-dione, (M+H)$^+$ 535;

[1S-[1R*,3R*(E),7R*,10S*,11R*,12R*,16S*]]-17-Benzoyl-7,11-dihydroxy-8,8,10,12-tetramethyl-3-[1-methyl-2-(2-methyl-4-thiazolyl)ethenyl]-4-oxa-17-azabicyclo[14.1.0]heptadecane-5,9-dione, (M+H)$^+$ 597;

[1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-17-(2-thienylcarbonyl)-4-oxa-17-azabicyclo[14.1.0]heptadecane-5,9-dione, (M+H)$^+$ 603;

[1S-[1R*,3R*(E),7R*,10S*,11R*,12R*,16S*]]-7,11-Dihydroxy-17-(methoxyacetyl)-8,8,10,12-tetramethyl-3-[1-methyl-2-(2-methyl-4-thiazolyl)ethenyl]-4-oxa-17-azabicyclo[14.1.0]heptadecane-5,9-dione, (M+H)$^+$ 565;

[1S-[1R*,3R*(E),7R*,10S*,11R*,12R*,16S*]]-17-(2-Oxopropanoyl)-7,11-dihydroxy-8,8,10,12-tetramethyl-3-[1-methyl-2-(2-methyl-4-thiazolyl)ethenyl]-4-oxa-17-azabicyclo[14.1.0]heptadecane-5,9-dione, (M+H)$^+$ 561; and

[1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-5,9-dioxo-4-oxa-17-azabicyclo[14.1.0]heptadecane-17-carboxylic acid ethyl ester, (M+H)+ 565.

The following are further compounds of the present invention:

[1S-[1R*,3R*(E),7R*,10S*,11R*,12R*,16S*]]-17-(2-Thienyl)carbonyl -7,11-dihydroxy-8,8,10,12-tetramethyl-3-[1-methyl-2-(2-methyl-4-thiazolyl)ethenyl]-4-oxa-17-azabicyclo[14.1.0]heptadecane-5,9-dione;

[1S-[1R*,3R*(E),7R*,10S*,11R*,12R*,16S*]]-17-(2-Thienyl)sulfonyl-7,11-dihydroxy-8,8,10,12-tetramethyl-3-[1-methyl-2-(2-methyl-4-thiazolyl)ethenyl]-4-oxa-17-azabicyclo[14.1.0]heptadecane-5,9-dione;

[1S-[1R*,3R*(E),7R*,10S*,11R*,12R*,16S*]]-17-Sulfonylurea-7,11-dihydroxy-8,8,10,12-tetramethyl-3-[1-methyl-2-(2-methyl-4-thiazolyl)ethenyl]-4-oxa-17-azabicyclo[14.1.0]heptadecane-5,9-dione;

[1S-[1R*,3R*(E),7R*,10S*,11R*,12R*,16S*]]-17-N-Methylsulfonylurea-7,11-dihydroxy-8,8,10,12-tetramethyl-3-[1-methyl-2-(2-methyl-4-thiazolyl)ethenyl]-4-oxa-17-azabicyclo[14.1.0]heptadecane-5,9-dione;

[1S-[1R*,3R*(E),7R*,10S*,11R*,12R*,16S*]]-17-Morpholinosulfonyl-7,11-dihydroxy-8,8,10,12-tetramethyl-3-[1-methyl-2-(2-methyl-4-thiazolyl)ethenyl]-4-oxa-17-azabicyclo[14.1.0]heptadecane-5,9-dione;

[1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-5,9-dioxo-4-oxa-17-azabicyclo[14.1.0]heptadecane-17-carboxylic acid phenylmethyl ester;

[1S-[1R*,3R*(E),7R*,10S*,11R*,12R*,16S*]]-7,11-Dihydroxy-8,8,10,12-tetramethyl-17-[(1-methyl-1H-imidazol-4-yl)sulfonyl]-3-[1-methyl-2-(2-methyl-4-thiazolyl)ethenyl]-4-oxa-17-azabicyclo[14.1.0]heptadecane-5,9-dione;

[1S-[1R*,3R*(E),7R*,10S*,11R*,12R*,16S*]]-7,11-Dihydroxy-17-(methoxyacetyl)-8,8,10,12-tetramethyl-3-[1-methyl-2-(2-methyl-4-thiazolyl)ethenyl]-4-oxa-17-azabicyclo[14.1.0]heptadecane-5,9-dione; and

[1S-[1R*,3R*(E),7R*,10S*,11R*,12R*,16S*]]-17-(2-Oxopropanoyl)-7,11-dihydroxy-8,8,10,12-tetramethyl-3-[1-methyl-2-(2-methyl-4-thiazolyl)ethenyl]-4-oxa-17-azabicyclo[14.1.0]heptadecane-5,9-dione.

The following compounds may also be prepared by the methods described above:

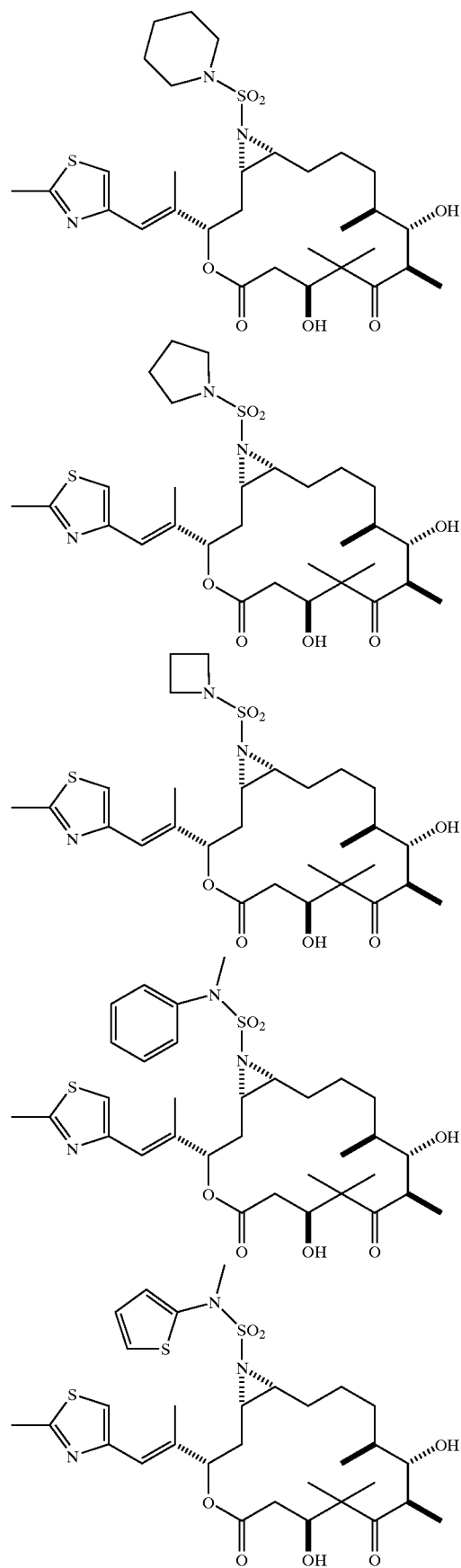

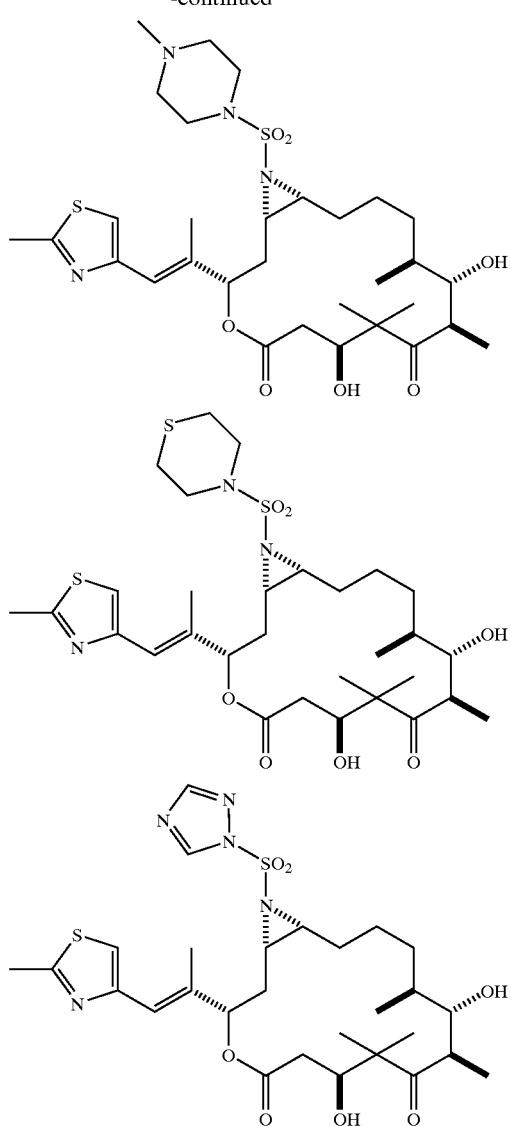

TABLE 1

In vitro data for aziridine analogues

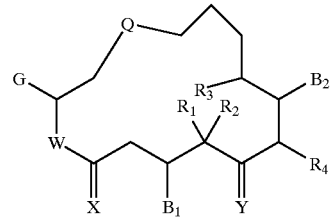

| Example Nos. | X | R | Tubulin assay EC$_{0.01}$ (uM) | HTC-116 assay IC$_{50}$ (nM) |
|---|---|---|---|---|
| Epothilone A | O | H | 2.0 | 4.4 |
| Epothilone B | O | Me | 1.8 | 0.8 |
| 1 | NH | H | 14 | 2.7 |
| 8 | NCH$_3$ | H | 2.6 | 0.13 |

TABLE 1-continued

In vitro data for aziridine analogues

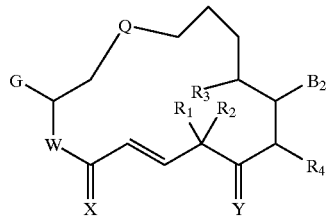

| Example Nos. | X | R | Tubulin assay EC$_{0.01}$ (uM) | HTC-116 assay IC$_{50}$ (nM) |
|---|---|---|---|---|
| 15 | NCH$_2$C$_6$H$_6$ | H | 35 | 23 |
| 5 | NCOCH$_2$CH(CH$_3$)$_2$ | H | 3.5 | 41 |
| 4 | NCOCH$_2$N(CH$_3$)$_2$ | H | >1000 | — |
| 21 | NCOCH$_3$ | H | 1.2 | 0.9 |
| 22 | NCOC$_6$H$_6$ | H | 1.4 | 3.0 |
| 23 | NCO-(2-thiophene) | H | 1.2 | 1.6 |
| 24 | NCOOCH$_2$CH$_3$ | H | 1.2 | 7.7 |
| 20 | NCOOC$_6$H$_6$ | H | 1.1 | 1.8 |
| 6 | NSO$_2$CH$_3$ | H | 14 | 2.1 |
| 25 | NSO$_2$CH$_2$CH$_3$ | H | 9.4 | 94 |
| 26 | NSO$_2$-(2-thiophene) | H | 4.0 | 30 |
| 16 | NSO$_2$NH$_2$ | H | 28 | 36 |
| 17 | NSO$_2$NHCH$_3$ | H | 2.3 | 7.8 |
| 18 | NSO$_2$N(CH$_3$)$_2$ | H | 1.0 | 0.2 |
| 19 | NSO$_2$N(CH$_2$CH$_2$)$_2$O | H | 460 | 160 |
| 7 | NCONHCH$_2$CH$_3$ | H | >1000 | — |

What is claimed is:

1. A compound of formula I or formula II:

[Formula I and Formula II structures]

wherein Q is

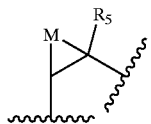

G is selected from the group consisting of heterocyclo, substituted heterocyclo,

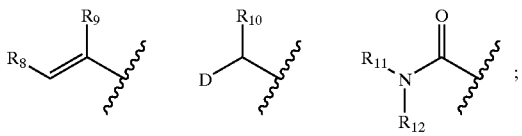

W is O or NR₁₆;

X is O, S, CHR₁₇ or H, R₁₈;

Y is selected from the group consisting of O; H, H; H, OR₂₂; OR₂₃, OR₂₃; NOR₂₄; H, NOR₂₅; H, NR₂₆R₂₇; NNR₂₈R₂₉; H, NHNR₃₀R₃₁; and CHR₃₂; where when Y is OR₂₃, OR₂₃, both R₂₃ can be taken toaether to form a cyclic ketal;

B₁ and B₂ are selected from the group consisting of H, OR₃₃, OCOR₃₄, OCONR₃₅R₃₆, NR₃₇R₃₈ and NR₃₉CONR₄₀R₄₁;

D is NR₄₂R₄₃, heterocyclo or substituted heterocyclo;

M is NR₄₄;

R₁, R₂, R₃, and R₄, are selected from H and lower alkyl;

R₅, R₉, and R₁₀ are selected from the group consisting of H, alkyl, substituted alkyl, aryl, substituted aryl, cycloalkyl, heterocyclo and substituted heterocyclo;

R₈ and R₁₁ are selected from heterocyclo and substituted heterocyclo;

R₁₇; R₁₈, R₂₂ and R₂₃ are selected from the group consisting of H, alkyl, and substituted alkyl;

R₂₄, R₂₅, R₂₆, R₂₈, R₃₀, R₃₂, R₃₃, R₃₄, R₃₅, R₃₆, R₃₇, R₃₉, R₄₀, R₄₁, R₄₂, R₅₂, R₅₃, R₆₁, R₆₂, and R₆₄, are selected from the group of H, alkyl, substituted alkyl, aryl, substituted aryl; heterocyclo and substituted heterocyclo;

R₆₃ is H, alkyl substituted alkyl, aryl, substituted aryl; heterocyclo or substituted heterocyclo;

or R₆₂ and R₆₃, together with the nitrogen atom to which they are attached, form a heterocycle or substituted heterocycle;

R₅₁ and R₅₁ₐ are independently heterocyclo or substituted heterocyclo;

R₁₂, R₁₆, R₂₇, R₂₉, R₃₁, and R₃₈, are selected from the group consisting of H alkyl, substituted alkyl, substituted aryl, cycloalkyl, heterocyclo, R₅₁C(=O)—, R₅₂OC(=O)—, R₅₃S(O)₂—, HO—, alkyl-O—, and substituted alkyl-O—; provided that when X is O then R₁₆ is not R₅₁C=O, R₅₂OC=O or R₅₃SO₂; and provided further, wherein when X is O and R₄₄ is amino, then R₁₆ is not R₆₁R₆₄NC=O;

R₄₃ is heterocyclo or substituted heterocyclo;

R₄₄ is R₅₁C(=O)—, R₅₁ₐS(O)₂— or R₆₂R₆₃NS(O)₂—;

and any salts, solvates or hydrates thereof, with the proviso that when the compound is of formula I wherein W is O, and R₁, R₂, R₃, and R₄ are each simultaneously methyl, then R₅₁ and R₅₁ₐ are not 2-thienyl; R₆₂ and R₆₃ are not both simultaneously methyl, and R₅₁ₐ is not 1-methyl-1H-imidazol-4-yl.

2. The compound of claim 1, or a salt, solvate, or hydrate thereof, wherein

G is 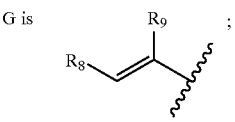;

X is O or S;

and Y is O.

3. A compound selected from the group consisting of:

[1S-[1R*,3R*(E),7R*,10S,11R*,12R*, 16S*]]-17-Sulfonylurea-7,11-dihydroxy-8,8,10,12-tetramethyl-3-[1-methyl-2-(2-methyl-4-thiazolyl)ethenyl]-4-oxa-17-azabicyclo[14.1.0]heptadecane-5,9-dione;

[1S-[1R*,3R*(E),7R*,10S,11R*,12R*, 16S*]]-17-N-Methylsulfonylurea-7,11-dihydroxy-8,8,10,12-tetramethyl-3-[1-methyl-2-(2-methyl-4-thiazolyl)ethenyl]-4-oxa-17-azabicyclo[14.1.0]heptadecane-5,9-dione;

[1S-[1R*,3R*(E),7R*,10S,11R*,12R*,16S*]]-17-Morpholinosulfonyl-7,11-dihydroxy-8,8,10,12-tetramethyl-3-[1-methyl-2-(2-methyl-4-thiazolyl)ethenyl]-4-oxa-17-azabicyclo[14.1.0]heptadecane-5,9-dione, and pharmaceutically-acceptable salts of each of the foregoing compounds.

4. A pharmaceutical composition comprising a compound of claim 1 and a pharmaceutically acceptable carrier.

5. A pharmaceutical composition comprising a compound of claim 1 in combination with a pharmaceutically acceptable carrier and an anti-cancer agent.

6. A method for modulating apoptosis which comprises administering to a mammal in need thereof an effective apoptosis modulating amount of a compound of claim 1.

7. A method for treating cancer which comprises administering to a mammal in need thereof a therapeutically effective amount of the composition of claim 4.

8. A method for treating cancer which comprises administering to a mammal in need thereof a therapeutically effective amount of the composition of claim 5.

9. A compound selected from the group consisting of:

[1S-[1R*,3R*(E),7R*,10S*,11R*,12R*,16S*]]-17-Benzyl-7,11-dihydroxy-8,8,10,12-tetramethyl-3-[1-methyl-2-(2-methyl-4-thiazolyl)ethenyl]-4-oxa-17-azabicyclo[14.1.0]heptadecane-5,9-dione; and

[1S-[1R*,3R*(E),7R*,10S*,11R*,12R*,16S*]]-17-(2-Oxopropanoyl)-7,11-dihodroxy-8,8,10,12-tetramethyl-3-[1-methyl-2-(2-methyl-4-thiazolyl)ethenyl]-4-oxa-17-azabicyclo[14.1.0]heptadecane-5,9-dione, and pharmaceutically-acceptable salts thereof.

10. A compound of claim 1, or a salt, solvate, or hydrate thereof, wherein W is O.

11. A compound of claim 1, or a salt, solvate, or hydrate thereof, wherein W is NR₁₆.

12. A compound of claim 1, or a salt, solvate, or hydrate thereof, having the formula (I),

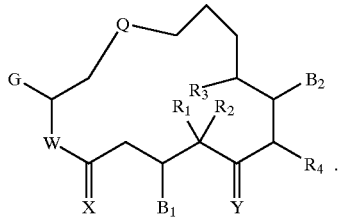
(I)

13. A compound of claim 12, or a salt, solvate, or hydrate thereof, wherein G is

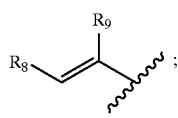

X is O;

Y is O;

$B_1$ and $B_2$ are both OH;

$R_1$, $R_2$, $R_3$, and $R_4$, are each methyl; and $R_9$ is H, lower alkyl, or substituted lower alkyl.

14. A compound of claim 1, or a salt, solvate, or hydrate thereof, having the formula (II),

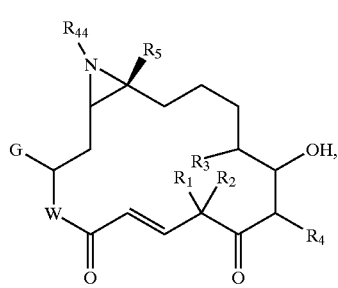
(II)

15. A compound of claim 14, or a salt, solvate, or hydrate thereof, wherein, G is

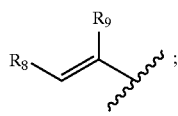

X is O;

Y is O;

$B_1$ and $B_2$ are both OH;

$R_1$, $R_2$, $R_3$, and $R_4$, are each methyl; and $R_9$ is H, lower alkyl, or substituted lower alkyl.

16. A compound having the formula (I) or (II),

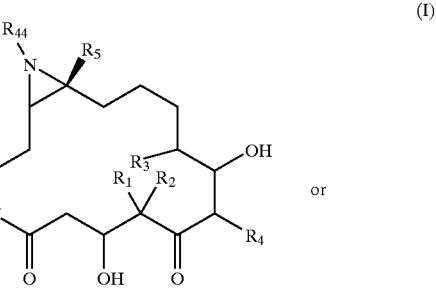

wherein,

G is

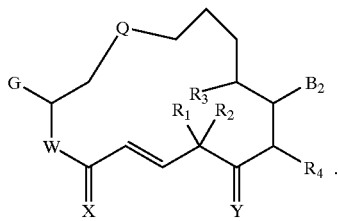

W is O or $NR_{16}$;

$R_1$, $R_2$, $R_3$, and $R_4$ are selected from H and lower alkyl;

$R_5$ and $R_9$ are selected from the group consisting of H, alkyl, substituted alkyl, aryl, substituted aryl, cycloalkyl, heterocyclo and substituted heterocyclo;

$R_8$ is selected from heterocyclo and substituted heterocyclo;

$R_{16}$ is H, alkyl, substituted alkyl, substituted aryl, cycloalkyl, heterocyclo, HO—, alkyl-O—, or substituted alkyl-O—;

$R_{44}$ is $R_{62}R_{63}NS(O)_2$—;

$R_{62}$ is H, alkyl, substituted alkyl, aryl, substituted aryl, heterocyclo or substituted heterocyclo, and $R_{63}$ is H, alkyl or substituted alkyl of 2 to 20 carbon atoms, aryl, substituted aryl, heterocyclo or substituted heterocyclo;

or $R_{62}$ and $R_{63}$, together with the nitrogen atom to which they are attached, form a heterocyclo or substituted heterocyclo;

and any salts, solvates or hydrates thereof.

17. A compound of claim 16, or a salt, solvate, or hydrate thereof, wherein W is O.

18. A compound of claim 16, or a salt, solvate, or hydrate thereof, wherein W is NH.

19. A compound of claim 16, having the formula,

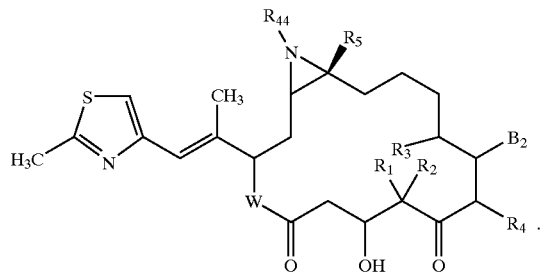

(Ia)

20. A compound of claim 16, wherein $R_{62}$ and $R_{63}$ together with the nitrogen atom to which they are attached form a heterocyclo selected from azetidinyl, pyrrolidinyl, piperidinyl, piperazinyl, morpholinyl, and triazolyl, or $R_{62}$ is H or lower alkyl and $R_{63}$ is phenyl, or thienyl, wherein each of said azetidinyl, pyrrolidinyl, piperidinyl, piperazinyl, morpholinyl, triazolyl, phenyl, or thienyl is optionally substituted with one to two lower alkyl.

* * * * *